US008173630B2

(12) United States Patent
Lindsey et al.

(10) Patent No.: US 8,173,630 B2
(45) Date of Patent: May 8, 2012

(54) MULTIPODAL TETHERS FOR HIGH-DENSITY ATTACHMENT OF REDOX-ACTIVE MOIETIES TO SUBSTRATES

(75) Inventors: Jonathan S. Lindsey, Raleigh, NC (US); David F. Bocian, Riverside, CA (US); Robert Loewe, Highlands Ranch, CO (US); Ignacio Sanchez, Glendale, CO (US); Werner G. Kuhr, Denver, CO (US); Kisari Padmaja, Raleigh, NC (US); Lingyun Wei, Englewood, CO (US)

(73) Assignees: The Regents of the University of California, Oakland, CA (US); The North Carolina State University, Raleigh, NC (US); Zettacore, Inc., Englewood, CO (US)

( * ) Notice: Subject to any disclaimer, the term of this patent is extended or adjusted under 35 U.S.C. 154(b) by 1371 days.

(21) Appl. No.: 11/446,586

(22) Filed: Jun. 1, 2006

(65) Prior Publication Data
US 2007/0108438 A1 May 17, 2007

Related U.S. Application Data

(60) Provisional application No. 60/687,762, filed on Jun. 3, 2005, provisional application No. 60/687,464, filed on Jun. 3, 2005.

(51) Int. Cl.
*A01N 55/02* (2006.01)
*C07B 47/00* (2006.01)
*C07D 487/22* (2006.01)

(52) U.S. Cl. ........................ 514/185; 540/145
(58) Field of Classification Search .............. 540/140, 540/145; 514/185
See application file for complete search history.

(56) References Cited

U.S. PATENT DOCUMENTS

| | | |
|---|---|---|
| 4,035,376 A | 7/1977 | Janssen et al. |
| 5,424,974 A | 6/1995 | Liu et al. |
| 6,272,038 B1 | 8/2001 | Clausen et al. |
| 2002/0154535 A1 | 10/2002 | Bocian et al. |
| 2002/0180446 A1 | 12/2002 | Kuhr |
| 2003/0075216 A1 | 4/2003 | Loewe et al. |
| 2003/0081463 A1 | 5/2003 | Bocian |
| 2003/0082444 A1 | 5/2003 | Kuhr |
| 2003/0092896 A1 | 5/2003 | Lindsey et al. |
| 2003/0096978 A1 | 5/2003 | Lindsey et al. |
| 2003/0096989 A1 | 5/2003 | Lindsey et al. |
| 2003/0104229 A1 | 6/2003 | Li |
| 2003/0111108 A1 | 6/2003 | Lindsey et al. |
| 2003/0111670 A1 | 6/2003 | Misra |
| 2003/0169618 A1 | 9/2003 | Lindsey |
| 2004/0120180 A1 | 6/2004 | Rotenberg |
| 2004/0241584 A1 | 12/2004 | Lindsey et al. |
| 2004/0254383 A1 | 12/2004 | Yu |
| 2005/0019500 A1 | 1/2005 | Bocian |
| 2005/0041494 A1 | 2/2005 | Bocian |
| 2005/0048691 A1 | 3/2005 | Bocian |
| 2005/0062097 A1 | 3/2005 | Misra |
| 2005/0096465 A1* | 5/2005 | Lindsey et al. ............... 540/145 |
| 2005/0185447 A1 | 8/2005 | Kuhr |
| 2005/0207208 A1 | 9/2005 | Bocian |
| 2005/0217559 A1 | 10/2005 | Bocian |
| 2005/0232000 A1 | 10/2005 | Lindsey et al. |
| 2006/0009638 A1 | 1/2006 | Lindsey et al. |
| 2006/0081950 A1 | 4/2006 | Kuhr |
| 2006/0142562 A1 | 6/2006 | Lindsey et al. |
| 2006/0209587 A1 | 9/2006 | Bocian |
| 2007/0027311 A1 | 2/2007 | Lindsey |
| 2007/0027312 A1 | 2/2007 | Lindsey |
| 2007/0055060 A1 | 3/2007 | Lindsey et al. |
| 2007/0108438 A1 | 5/2007 | Lindsey et al. |
| 2007/0123618 A1 | 5/2007 | Bocian |
| 2007/0191600 A1 | 8/2007 | Yu |
| 2007/0212897 A1 | 9/2007 | Bocian |
| 2008/0027232 A1 | 1/2008 | Lindsey et al. |
| 2008/0071093 A1 | 3/2008 | Lindsey et al. |
| 2008/0194839 A1 | 8/2008 | Lindsey et al. |
| 2008/0221319 A1 | 9/2008 | Kiper et al. |
| 2008/0269501 A1 | 10/2008 | Lindsey et al. |
| 2008/0280047 A1 | 11/2008 | Bocian |

FOREIGN PATENT DOCUMENTS

WO   WO2007053192   5/2007

OTHER PUBLICATIONS

PCT International Search Report dated Feb. 11, 2008 issued in PCTUS2006021516 (WO2007053192).
PCT Preliminary Examination Report dated Mar. 10, 2009 issued in PCTUS2006021516 (WO2007053192).
PCT International Written Opinion dated Feb. 11, 2008 issued in PCTUS2006021516 (WO2007053192).
Balakumar, Arumugham et al. (2004) "Diverse Redox-Active Molecules Bearing 0-, S-, or Se-Terminated Tethers for Attachment to Silicon in Studies of Molecular Information Storage," *Jrnl of Org. Chem.*, 69, No. 5; Mar. 5, 2004, pp. 1435-1443.
Buriak, Julian M. (1999) "Organometallic Chemistry on Silicon Surfaces: Formation of Functional Monolayers Bound Through Si-C Bonds", *Jrnl Chem. Soc., Chemical Communications*, 1999, pp. 1051-1060.
Buriak, Julian M., (2002) "Organometallic Chemistry on Silicon and Germanium Surfaces," *Chemical Reviews*, vol. 102, No. 5, May 2002, pp. 271-1308.
Chiellini et al. (1978) "One-step dialkylation of phenylacetonitrile in the Presence of Tertiary Amines," *Jrnl Organic Chem.*, vol. 43, No. 12, pp. 2550-2551.
Lin, Shou-Yuan et al. (1997) "A Facile Synthesis of 4-(Trialkylmethyl) Anilines by the Reaction of 4-(Triflouromethyl) Aniline With Grignard Reagents," *Synth. Comm.*, vol. 27(11), pp. 1975-1980.
Liu et al. (2004) "Synthesis of Porphyrins Bearing Hydrocarbon Tethers and Facile Covalent Attachment to Si(100)," *Jrnl Org. Chem.*, vol. 69, pp. 5568-5577.

(Continued)

*Primary Examiner* — Paul V. Ward
(74) *Attorney, Agent, or Firm* — Weaver Austin Villeneuve & Sampson LLP; Tom Hunter

(57) ABSTRACT

This invention provides redox-active molecules attached to polypodal (e.g., bipodal, tripodal, quadrapodal, pentapodal, etc.) tethers that can be used for attachment of the redox-active molecules to a substrate (e.g., an electrode). The tethered redox-active molecules are useful for the fabrication of memory devices.

108 Claims, 28 Drawing Sheets

OTHER PUBLICATIONS

Loewe et al. (2004) "Porphyrins Bearing Mono or Tripodal Benzylphosphonic Acid Tethers for Attachment to Oxide Surfaces," *Jrnl Org. Chem.*, No. 69, pp. 1453-1460.

Martinez et al. (2002), "General Route from Simple Methyl, Alkyl, and Cycloalkyl Arenes to Polycyclic Cyclopentenyl Aryl Derivatives. The CpFe+ Group as an Activator and Tag," *Org. Lett.*, Jan. 19, 2002, vol. 4, No. 4, pp. 651-653.

Muthukumaran et al. (2004) "Porphyrins Bearing Arylphosphonic Acid Tethers for Attachment to Oxide Surfaces," *Jrnl Org. Chem.*, vol. 69, pp. 1444-1452.

Roth et al. (2003) "Measurements of Electron-Transfer Rates of Charge-Storage Molecular Monolayers on Si(100). Toward Hybrid Molecular/Semiconductor Information Storage Devices," *Jrnl Am. Chem. Soc.*, Dec. 7, 2002, vol. 125, pp. 505-517.

Sartor et al. (2000) "Activation of aryl ethers and aryl sulfides by the Fe($\eta^5$-$C_5H_5$)+ group for the synthesis of phenol dendrons and arene-centered poly-olefin dendrimers," *New Jrnl Chem.*, 2004, vol. 24, pp. 351-370.

Wei, Lingyun et al. (2004) "Diverse Redox-Active Molecules Bearing Identical Thiol-Terminated Tripodal Tethers for Studies of molecular Information Storage," *Jrnl Org. Chem.*, 2004, vol. 69, pp. 1461-1469.

Wei, Lingyun et al. (2005) "Structural and Electron-Transfer Characteristics of Carbon-Tethered Porphyrin Monolayers on Si(100)," *J. Phys. Chem. B.*, 2005, vol. 109, pp. 6323-6330.

Yamada et al. (2005) "Reaction of Octafluorocyclopentene with Various Carbon Nucleophiles," *Jrnl of Flurine Chem*. vol. 126, Issue 1, Jan. 2005, Abstract.

Yasseri et al. (2004) "Characterization of Self-Assembled Monolayers of Porphyrins Bearing Multiple Thiol-Derivatized Rigid-Rod Tethers," *Jrnl Am. Chem. Soc.*, vol. 126, pp. 15603-15612.

Yasseri et al. (2004) "Structural and Electron-Transfer Characteristics of O-, S-, and Se-Tethered Porphyrin Monolayers on Si(100)," *Jrnl Am. Chem. Soc.*, vol. 126, pp. 11944-11953.

Yu and Lindsey (2001) "Investigation of two rational routes for preparing ρ-phenylene-linked porphyrin trimers," *Tetrahedron* 57: 9285-9298.

PCT International Preliminary Report on Patentability and Written Opinion dated Feb. 11, 2008 issued in PCT/US2006/021516 (WO 2007/053192).

Yasseri et al. (2004) "Characterization of Self-Assembled Monolayers of Porphyrins Bearing Multiple Thiol-Derivatized Rigid-Rod Tethers", *J. Am. Chem. Soc.*, 126:11944-11953.

Yasseri et al. (2004) "Structural and Electron-Transfer Characteristics of O-, S-, and Se-Tethered Porphyrin Monolayers on Si(100)", *J. Am. Chem. Soc.*, 126:15603-15612.

\* cited by examiner

| | R |
|---|---|
| 3a: | -H |
| 3b: | -CH$_3$ |
| 3c: | -NH$_2$ |
| 3d: | -OH |
| 3e: | -OCH$_3$ |
| 3f: | -SCH$_3$ |
| 3g: | -SCH$_2$CH$_3$ |

Scheme 1

C = carbon
Ha = heteroatom or carbon
⌇⌇⌇ = single or double bond
···Q··· = together with –C~~Ha~~C– form independently selected 5 or 6 membered rings, optionally substituted with 1, 2, or 3 $R^2$ groups, such that the compound is electronically conjugated.
n = 0 or 1
X = independently selected from
—CHR'—  —CRR—CR=
=CR—  —CR—CRR—
—CR=  =CR—CR=
—N=  —CR=CR—
—N—  —(CRR)$_p$—
—NR—

Scheme 6

Scheme 7

*Scheme 8*

Scheme 9

MULTIPODAL TETHERS FOR HIGH-DENSITY ATTACHMENT OF REDOX-ACTIVE MOIETIES TO SUBSTRATES

CROSS-REFERENCE TO RELATED APPLICATIONS

This application claims benefit of and priority to U.S. Ser. No. 60/687,762, filed on Jun. 3, 2005 and to U.S. Ser. No. 60/687,464, filed on Jun. 3, 2005, both of which are incorporated herein by reference in their entirety for all purposes.

STATEMENT AS TO RIGHTS TO INVENTIONS MADE UNDER FEDERALLY SPONSORED RESEARCH AND DEVELOPMENT

This work was supported in part by the Center for Nanoscience Innovation for Defense and DARPA/DMEA (award number H94003-04-2-0404). The Government of the United States of America has certain rights in this invention.

FIELD OF THE INVENTION

This invention pertains to the field of molecular electronics, in particular to molecular memory elements. Polypodal tethers are provided for the attachment of redox-active molecules to substrates (e.g., electrodes) resulting in increased charge/storage density.

BACKGROUND OF THE INVENTION

An increasing problem facing the semiconductor industry is that devices which rely on bulk properties of semiconductors will fail to retain their characteristic properties as feature sizes reach nanoscale dimension. The field of molecular electronics has grown significantly in the past few years in response to this reality. There has been much interest in developing molecule-based electronic materials for use in memory devices and as circuit elements. One approach has focused on memory applications wherein molecules attached to an electroactive surface serve as the active medium. The ability to store charge in the discrete redox states of molecules in effect mimics the function of semiconductor capacitors, such as those found in dynamic random access memory (DRAM) cells (which is comprised of a transistor-capacitor pair). This hybrid approach proceeds through transition-technologies wherein molecular materials are first integrated with semiconductors, thereby capitalizing on the vast infrastructure of the semiconductor industry.

Among several candidate redox-active molecules, we have found that porphyrinic macrocycles (e.g., porphyrins) are effective as the active memory element in molecular-based capacitors/storage cells. Porphyrins generally form robust, well-defined self-assembled monolayers (SAMs) on a variety of electroactive surfaces, display two (or three) stable cationic redox states of modest potential (0.5 V-1.2 V vs Ag/Ag$^+$), readily participate in facile electron-transfer reactions, and display thermal stability, which is important as many chip processing steps require high temperatures. Several parameters are available for alteration. Specifically, we have examined the nature of the central metal, spacer group, surface-attachment group, and the non-linking meso-substituents. Alterations to one or more of these parameters can affect the redox-potentials, the number of redox-states, surface coverages, charge-injection rates, and charge-retention times of the resulting porphyrin SAMs.

Accordingly, due to the interest in molecular memory systems, improved methods of attachment and the compositions for such attachments are desirable.

SUMMARY OF THE INVENTION

One approach to increase the charge storage density is to employ redox-active molecules that possess a multipodal (e.g., bipodal, tripodal, quadrapodal, pentapodal, etc.) tether that can be used for attachment of the redox-active molecules to a substrate. Such systems are anticipated to yield redox-active molecule layers in which the redox-active components of the molecules are oriented in a manner that provides a higher charge density. Without being bound to a particular theory it is believed that the use of multipodal tethers dramatically increases surface coverage, and likely increases the stability of the molecules comprising the latter since fewer native surface atoms remain unbound, thus limiting substrate and/or redox-active molecule degradation pathways.

This invention pertains to the use of redox-active molecules attached to various multipodal tethers. Thus, in one embodiment, this invention provides a composition comprising an array of electrodes, where a plurality of the electrodes each comprise a redox-active molecule attached to an electrode via a polypodal tether, e.g., as described herein. In certain embodiments the polypodal tether is a 2-podal, 3-podal, 4-podal, or 5-podal tether. In certain embodiments the legs of the tether do not contain a phenyl moiety (e.g. a phenylene) and/or each leg of the tether contains at least one carbon and not more than 10 carbons. In certain embodiments the composition comprises a tripod tether as described herein. In various embodiments the plurality of electrodes each comprising a redox-active molecule attached to the electrode is disposed such that the oxidation state of the redox-active molecules can be independently set or read in at least $10^4$, preferably at least $10^6$, more preferably at least $10^9$ different locations in the array. The plurality of electrodes can, optionally, be encapsulated. In certain embodiments the plurality of electrodes are disposed within an electrolyte.

This invention also provides a composition comprising a redox-active molecule attached to a polypodal tether as described herein. In certain embodiments the legs of said tether do not contain a phenyl moiety (e.g., a phenylene) and/or each leg of said tether contains at least one carbon and not more than 10 carbons. In certain embodiments the composition comprises a tripod tether as described herein. In various embodiments the multi-podal tether is attached to an electrode through at least one leg, preferably through at least two legs, more preferably, where present, through at least 3 legs of the tether. In certain embodiments the tether is attached to a substrate comprising a material selected from the group consisting of a Group IV element, a Group V element, a Group VI element, and a metal. In certain embodiments the tether is attached to a substrate comprising a material selected from the group consisting of silicon, germanium, silver, gold, copper, titanium, tantalum, tungsten, a doped silicon, a doped germanium, a silicon oxide, a germanium oxide, a silver oxide, a copper oxide, a titanium oxide, a tantalum oxide, a tungsten oxide, a silicon nitride, a germanium nitride, a silver nitride, a copper nitride, a titanium nitride, a tantalum nitride, and a tungsten nitride. In certain embodiments the tether is attached to a substrate comprising Si(100).

Also provided is an apparatus comprising a fixed electrode electrically coupled to a storage medium comprising a redox-active molecule attached to a polypodal tether as described herein, wherein the storage medium has at least two different and distinguishable non-zero oxidation states. In certain embodiments the storage medium comprises redox-active molecules covalently linked to the electrode. In certain embodiments the storage medium comprises redox-active molecules electrically coupled to the electrode through a bipod or tripod tether. In certain embodiments the storage medium is electrically coupled to said electrode through a dielectric. In certain embodiments the storage medium is juxtaposed in the proximity of said electrode such that electrons can pass from said storage medium to said electrode. In various embodiments the storage medium is juxtaposed to a dielectric material imbedded with counterions. The storage medium and the electrode can optionally be fully encapsulated in an integrated circuit. In certain embodiments the storage medium is electronically coupled to a second fixed electrode that is a reference electrode. In various embodiments the storage medium is present on a single plane in the apparatus and/or on multiple planes in the apparatus. In various embodiments the storage locations are present on a single plane in said apparatus and/or the apparatus comprises multiple planes and said storage locations are present on multiple planes of said apparatus. In various embodiments the apparatus comprises more than about 1024 different storage locations, preferably more than about $10^6$ different storage locations, more preferably more than about $10^9$ different storage locations. In certain embodiments each location is addressed by two electrodes. One or more electrodes can be connected to a voltage source (e.g., the output of an integrated circuit). One or more electrodes can be connected to a device (e.g., a voltammetric device, an amperometric device, a potentiometric device, etc.) to read the oxidation state of the storage medium. In various embodiments the device is an impedance spectrometer or a sinusoidal voltammeter. In certain embodiments the device can, optionally provide a Fourier transform of the output signal from the electrode(s). In certain embodiments the device refreshes the oxidation state of the storage medium after reading the oxidation state. In certain embodiments the different and distinguishable oxidation states of said storage medium can be set by a voltage difference no greater than about 2 volts.

Also provided is a memory device comprising a substrate, where the substrate comprises a plurality of storage cells, each storage cell comprising. a fixed electrode electrically coupled to a storage medium comprising a redox-active molecule attached to a polypodal tether as described herein where the composition has at least two different and distinguishable, preferably non-zero, oxidation states. In certain embodiments the memory device comprises at least 1024 different storage cells, more preferably at least $10^6$ storage cells, most preferably at least $10^9$ different storage cells. In certain embodiments the device is present in an article of manufacture (e.g., a computer, a cell phone, a PDA, a video game controller, a digital video recorder, a digital music player, a digital video player, a telephone, an optical drive, a removable storage medium, and the like). In various embodiments each storage cell location is addressed by at least one or two electrodes.

This invention also provides methods of storing information. The methods typically involve a) providing a substrate comprising: i) a plurality of storage locations each comprising a redox-active molecule attached to a polypodal tether as described herein;
ii) at least one working electrode; and iii) at least one reference electrode; and b) applying a potential to said electrodes to set the oxidation state of said composition in at least a first storage location and a second storage location. In certain embodiments the substrate further comprises an electrolyte layer. In certain embodiments the potential is 2 volts or less. In various embodiments the potential is the output of an integrated circuit and/or a logic gate. In various embodiments the method further involves detecting the oxidation state of the composition in at least a first location and thereby reading out the data stored therein. In certain embodiments detecting the oxidation state of the composition further comprises refreshing the oxidation state of the composition. In various embodiments the detecting comprises analyzing a readout signal in the time domain and/or the frequency domain.

In certain embodiments this invention provides a computer system comprising a memory device as described herein. In various embodiments this invention provides a computer system comprising a central processing unit, a display, a selector device, and a memory device as described herein. Also provided is a cell phone comprising a memory device as described herein.

In certain embodiments this invention expressly excludes tethers where one or more legs of the tether comprises a benzene and/or tripodal tethers as illustrated in the compounds of FIG. 2.

DEFINITIONS

The term "chemisorbed species" refers to a molecule chemically, or otherwise, bonded/attached to a substrate. In certain embodiments all or some of the chemisorbed species can be covalently bonded covalently bonded to a substrate.

The term "oxidation" refers to the loss of one or more electrons in an element, compound, or chemical substituent/subunit. In an oxidation reaction, electrons are lost by atoms of the element(s) involved in the reaction. The charge on these atoms must then become more positive. The electrons are lost from the species undergoing oxidation and so electrons appear as products in an oxidation reaction. An oxidation is taking place in the reaction $Fe^{2+}(aq) \rightarrow Fe^{3+}(aq)+e^-$ because electrons are lost from the species being oxidized, $Fe^{2+}(aq)$, despite the apparent production of electrons as "free" entities in oxidation reactions. Conversely the term reduction refers to the gain of one or more electrons by an element, compound, or chemical substituent/subunit.

An "oxidation state" refers to the electrically neutral state or to the state produced by the gain or loss of electrons to an element, compound, or chemical substituent/subunit. In a preferred embodiment, the term "oxidation state" refers to states including the neutral state and any state other than a neutral state caused by the gain or loss of electrons (reduction or oxidation).

The term "multiple oxidation states" means more than one oxidation state. In certain embodiments, the oxidation states may reflect the gain of one or more electrons (reduction) or the loss of one or more electrons (oxidation).

The terms "different and distinguishable" when referring to two or more oxidation states means that the net charge on the entity (atom, molecule, aggregate, subunit, etc.) can exist in two or more different states. The states are said to be "distinguishable" when the difference between the states is greater than thermal energy at room temperature (e.g., 0° C. to about 40° C.). In certain embodiments, the states are distinguishable when a difference can be detected under the conditions of the assay.

The term "electrode" refers to any material or medium capable of transporting charge (e.g., electrons) to and/or from a location (e.g., a storage molecule). In an electrochemical context, the term "electrode" refers to a part(s) of an electrochemical cell that allows electrons to be transferred to and/or from reactants (e.g., redox-active molecules such as storage molecules) in the electrochemical cell. In certain embodiments preferred electrodes include metals and/or metal oxides, nitrides, and the like, and/or semiconductors, and/or conductive organic molecules. For some electrodes (e.g., W, Ti, Ta, Si, etc.), there may be a layer of native oxide or intentionally grown oxide on the surface of the electrode. This oxide can still permit electrons to be transferred to and/or from reactants in the electrochemical cell (e.g., via tunneling or because of pinholes in the oxide). The electrodes can be manufactured to virtually any 2-dimensional or 3-dimensional shape (e.g. discrete lines, pads, planes, spheres, cylinders, etc.). In other contexts, an electrode refers to a conductor used to make electrical contact with part of a circuit.

The term "fixed electrode" is intended to reflect the fact that the electrode is essentially stable and unmovable with respect to the storage medium and/or a substrate on which the electrode may reside. That is, the electrode and storage medium are arranged in an essentially fixed geometric relationship with each other. It is of course recognized that the relationship alters somewhat due to expansion and contraction of the medium with thermal changes or due to changes in conformation of the molecules comprising the electrode and/or the storage medium. Nevertheless, the overall spatial arrangement remains essentially invariant. In a preferred embodiment this term is intended to exclude systems in which the electrode is a movable "probe" (e.g., a writing or recording "head", an atomic force microscope (AFM) tip, a scanning tunneling microscope (STM) tip, etc.).

The term "working electrode" is used to refer to one or more electrodes that are used to set or read the state of a storage medium and/or storage molecule (e.g., redox-active molecule).

The term "reference electrode" is used to refer to one or more electrodes that provide a reference (e.g., a particular reference voltage) for measurements recorded from the working electrode. In preferred embodiments, the reference electrodes in a memory device of this invention are at the same potential although in some embodiments this need not be the case.

The term "electrically coupled" when used with reference to a storage molecule (redox-active molecule) and/or storage medium and electrode refers to an association between that storage medium or molecule and the electrode such that electrons move from the storage medium/molecule to the electrode or from the electrode to the storage medium/molecule and thereby alter the oxidation state of the storage medium/molecule. Electrical coupling can include direct covalent linkage between the storage medium/molecule and the electrode, indirect covalent coupling (e.g., via a linker), direct or indirect ionic bonding between the storage medium/molecule and the electrode, or other bonding (e.g., hydrophobic bonding). In addition, no actual bonding may be required and the storage medium/molecule may simply be contacted with the electrode surface. There also need not necessarily be any contact between the electrode and the storage medium/molecule where the electrode is sufficiently close to the storage medium/molecule to permit electron tunneling between the medium/molecule and the electrode.

The terms "redox-active molecule (ReAM) refer to a molecule or component of a molecule that is capable of being oxidized or reduced, e.g., by the application of a suitable voltage. As described below, ReAMs can include, but are not limited to macrocycles including porphyrin and porphyrin derivatives, as well as non-macrocyclic compounds, and includes sandwich compounds, e.g. as described herein. In certain embodiments, ReAMs can comprise multiple subunits, for example, in the case of dyads or triads.

The term "subunit", as used herein, refers to a redox-active component of a molecule.

The terms "storage molecule" or "memory molecule" refer to a molecule having one or more oxidation states (i.e., a redox-active molecule) that can be used for the storage of information (e.g., a molecule comprising one or more redox-active subunits). In certain embodiments redox-active molecules for use in this invention have at least two, preferably at least 3, more preferably at least 4, 8, or 16, or more different and distinguishable non-neutral oxidation states.

The term "storage medium" refers to a composition comprising two or more storage molecules (redox-active molecules). The storage medium can contain only one species of storage molecule or it can contain two or more different species of storage molecule. In certain embodiments the storage media comprise a multiplicity (at least 2) of different and distinguishable (preferably non-neutral) oxidation states. The multiplicity of different and distinguishable oxidation states can be produced by the combination of different species of storage molecules, each species contributing to said multiplicity of different oxidation states and each species having a single non-neutral oxidation state. Alternatively or in addition, the storage medium can comprise one or more species of storage molecule having a multiplicity of non-neutral oxidation states. The storage medium can contain predominantly one species of storage molecule or it can contain a number of different storage molecules. The storage media can also include molecules other than storage molecules (e.g., to provide chemical stability, to provide suitable mechanical properties, to prevent charge leakage, etc.).

The term "electrochemical cell" consists minimally of a reference electrode, a working electrode, a redox-active medium (e.g., a storage medium), and, if necessary, some means (e.g., a dielectric) for providing electrical conductivity between the electrodes and/or between the electrodes and the medium. In some embodiments, the dielectric is a component of the storage medium.

The terms "memory element", "memory cell", or "storage cell" refer to an electrochemical cell that can be used for the storage of information. Preferred "storage cells" are discrete regions of storage medium addressed by at least one and preferably by two electrodes (e.g., a working electrode and a reference electrode). The storage cells can be individually addressed (e.g., a unique electrode is associated with each memory element) or, particularly where the oxidation states of different memory elements are distinguishable, multiple memory elements can be addressed by a single electrode. The memory element can optionally include a dielectric (e.g., a dielectric impregnated with counterions).

The term "storage location" refers to a discrete domain or area in which a storage medium is disposed. When addressed with one or more electrodes, the storage location may form a storage cell. However if two storage locations contain the same storage media so that they have essentially the same oxidation states, and both storage locations are commonly addressed, they may form one functional storage cell.

Addressing a particular element refers to associating (e.g., electrically coupling) that memory element with an electrode such that the electrode can be used to specifically set and/or determine the oxidation state(s) of that memory element.

The term "storage density" refers to the number of bits per volume and/or bits per molecule that can be stored. When the storage medium is said to have a storage density greater than one bit per molecule, this refers to the fact that a storage medium preferably comprises molecules wherein a single molecule is capable of storing at least one bit of information.

The terms "read" or "interrogate" refer to the determination of the oxidation state(s) of one or more molecules (e.g., molecules comprising a storage medium).

The term "refresh" when used in reference to a storage molecule or to a storage medium refers to the application of a voltage to the storage molecule or storage medium to re-set the oxidation state of that storage molecule or storage medium to a predetermined state (e.g., an oxidation state the storage molecule or storage medium was in immediately prior to a read).

The term "$E_{1/2}$" refers to the practical definition of the formal potential ($E°$) of a redox process as defined by $E=E°+(RT/nF)\ln(D_{ox}/D_{red})$ where R is the gas constant, T is temperature in K (Kelvin), n is the number of electrons involved in the process, F is the Faraday constant (96,485 Coulomb/mole), $D_{ox}$ is the diffusion coefficient of the oxidized species and $D_{red}$ is the diffusion coefficient of the reduced species.

A voltage source is any source (e.g., molecule, device, circuit, etc.) capable of applying a voltage to a target (e.g., an electrode).

The term "present on a single plane", when used in reference to a memory device of this invention refers to the fact that the component(s) (e.g., storage medium, electrode(s), etc.) in question are present on the same physical plane in the device (e.g., are present on a single lamina). Components that are on the same plane can typically be fabricated at the same time, e.g., in a single operation. Thus, for example, all of the electrodes on a single plane can typically be applied in a single (e.g., sputtering) step (assuming they are all of the same material).

The phrase "output of an integrated circuit" refers to a voltage or signal produced by one or more integrated circuit(s) and/or one or more components of an integrated circuit.

A "voltammetric device" is a device capable of measuring the current produced in an electrochemical cell as a result of the application of a voltage or change in voltage.

An "amperometric device" is a device capable of measuring the current produced in an electrochemical cell as a result of the application of a specific potential ("voltage").

A "potentiometric device" is a device capable of measuring potential across an interface that results from a difference in the equilibrium concentrations of redox molecules in an electrochemical cell.

A "coulometric device" is a device capable of the net charge produced during the application of a potential field ("voltage") to an electrochemical cell.

An "impedance spectrometer" is a device capable of determining the overall impedance of an electrochemical cell.

A "sinusoidal voltammeter" is a voltammetric device capable of determining the frequency domain properties of an electrochemical cell.

The terms "proligand" or "macrocyclic proligand" refer to a cyclic compound that contain donor atoms (sometimes referred to herein as "coordination atoms") oriented so that they can encircle and bind to a metal ion. In general, the donor atoms are heteroatoms including, but not limited to, nitrogen, oxygen and sulfur, with the former being especially preferred. As will be appreciated by those in the art, different metal ions bind preferentially to different heteroatoms, and thus the heteroatoms used can depend on the desired metal ion. In addition, in some embodiments, a single macrocycle can contain heteroatoms of different types. FIG. 11 depicts a broad macrocyclic ligand (e.g. the proligand (when q is 0) or the complex (when q is 1).

The term "porphyrinic macrocycle" refers to a porphyrin or porphyrin derivative. Such derivatives include porphyrins with extra rings ortho-fused, or ortho-perifused, to the porphyrin nucleus, porphyrins having a replacement of one or more carbon atoms of the porphyrin ring by an atom of another element (skeletal replacement), derivatives having a replacement of a nitrogen atom of the porphyrin ring by an atom of another element (skeletal replacement of nitrogen), derivatives having substituents other than hydrogen located at the peripheral (meso-, β-) or core atoms of the porphyrin, derivatives with saturation of one or more bonds of the porphyrin (hydroporphyrins, e.g., chlorins, bacteriochlorins, isobacteriochlorins, decahydroporphyrins, corphins, pyrrocorphins, etc.), derivatives obtained by coordination of one or more metals to one or more porphyrin atoms (metalloporphyrins), derivatives having one or more atoms, including pyrrolic and pyrromethenyl units, inserted in the porphyrin ring (expanded porphyrins), derivatives having one or more groups removed from the porphyrin ring (contracted porphyrins, e.g., corrin, corrole) and combinations of the foregoing derivatives (e.g., phthalocyanines, sub-phthalocyanines, and porphyrin isomers). Preferred porphyrinic macrocycles comprise at least one 5-membered ring.

The term "ReAM polymer" refers to a discrete number of two or more covalently-linked ReAMs (e.g., porphyrinic macrocycles). The ReAM polymers can be linear, cyclic, or branched.

The terms "sandwich coordination compound" or "sandwich coordination complex" refer to a compound of the formula $L_nM^{n-1}$, where each L is a heterocyclic ligand (as described below), each M is a metal, n is 2 or more, most preferably 2 or 3, and each metal is positioned between a pair of ligands and bonded to one or more hetero atom (and typically a plurality of hetero atoms, e.g., 2, 3, 4, 5) in each ligand. The ligands in the sandwich coordination compound are generally arranged in a stacked orientation, i.e., they are generally cofacially oriented and axially aligned with one another, although they may or may not be rotated about that axis with respect to one another (see, e.g., Ng and Jiang (1997) *Chem. Soc. Rev.*, 26: 433-442).

The term "double-decker sandwich coordination compound" refers to a sandwich coordination compound as described above where n is 2, thus having the formula $L^1$-M-$L^2$, wherein each of $L^1$ and $L^2$ may be the same or different (see, e.g., Jiang et al. (1999) *J. Porphyrins Phthalocyanines* 3: 322-328 and U.S. Pat. Nos. 6,212,093; 6,451,942; 6,777,516, and the like. Polymerization of these molecules is described in U.S. Ser. No. 10/800,147, filed on Mar. 11, 2004, entitled Procedure for Preparing Redox-Active Polymers on Surfaces, and PCT Publication WO 2005/08682 all of which are incorporated herein by reference).

The term "triple-decker sandwich coordination compound" refers to a sandwich coordination compound as described above where n is 3, thus having the formula $L^1$-M-$L^2$-$M^2$-$L^3$, wherein each of $L^1$, $L^2$ and $L^3$ may be the same or different, and $M^1$ and $M^2$ may be the same or different (see, e.g., Arnold et al. (1999) *Chem. Lett.* 483-484), and U.S. Pat. Nos. 6,212,093; 6,451,942; 6,777,516. Polymerization of these molecules is described in U.S. Ser. No. 10/800,147, filed on Mar. 11, 2004, entitled Procedure for Preparing Redox-Active Polymers on Surfaces, and PCT Publication WO 2005/08682 which are incorporated herein by reference.

A "linker" is a molecular entity used to couple two or more different molecules, two or more subunits of a molecule, or one or more molecules to a substrate. Linkers are more fully described below.

In the context of molecular attachment, a "substrate" is a, preferably solid, semisolid, or gelatinous material suitable for the attachment of one or more redox-active molecules. Substrates can be formed of materials including, but not limited to glass, plastic, carbon, silicon, germanium, minerals (e.g., quartz), semiconducting materials (e.g., doped silicon, silicon oxides, doped germanium, etc.), ceramics, metals, metal oxides or nitrides, etc. In other contexts, a substrate refers to: (a) a silicon wafer or (b) the body or base layer of an integrated circuit, onto which other layers are deposited, e.g., a silicon substrate or a sapphire substrate. In certain embodiments an electrode can be a substrate or a component of a substrate.

"Alkyl" by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Also included within the definition of an alkyl group are cycloalkyl groups such as C5 and C6 rings, and heterocyclic rings with nitrogen, oxygen, sulfur or phosphorus (heterocycloalkyl). Alkyl also includes heteroalkyl, with heteroatoms of sulfur, oxygen, nitrogen, and silicon being preferred.

The term "alkyl" is specifically intended to include groups having any degree or level of saturation, i.e., groups having exclusively carbon-carbon single bonds, groups having one or more carbon-carbon double bonds, groups having one or more carbon-carbon triple bonds and groups having mixtures of single, double and triple carbon-carbon bonds. Where a specific level of saturation is intended, the expressions "alkanyl," "alkenyl," and "alkynyl" are used. Preferably, an alkyl group comprises from 1 to 20 carbon atoms, more preferably, from 1 to 10 carbon atoms, most preferably, from 1 to 6 carbon atoms.

"Alkanyl" by itself or as part of another substituent, refers to a saturated branched, straight-chain or cyclic alkyl radical derived by the removal of one hydrogen atom from a single carbon atom of a parent alkane.

"Alkenyl" by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s).

"Alkynyl" by itself or as part of another substituent, refers to an unsaturated branched, straight-chain or cyclic alkyl radical having at least one carbon-carbon triple bond derived by the removal of one hydrogen atom from a single carbon atom of a parent alkyne.

Also included within the definition of "alkyl" is "substituted alkyl". "Substituted" particularly designated by S or S" where n is an integer, or as $R_1$ or $R_2$ or R or R' in the formulas, refers to a group in which one or more hydrogen atoms are independently replaced with the same or different substituent(s). Typical substituents include, but are not limited to, halogen (e.g., F, Cl, Br, I, At), —R, —O$^-$, =O, —OR, —SR, —S$^-$, =S, —NRR', =NR, —CF$_3$, —CN, —OCN, —SCN, —NO, —NO$_2$, =N$_2$, —N$_3$, —S(O)$_2$O—, —S(O)$_2$OH, —S(O)$_2$R, —OS(O)$_2$O$^-$, —OS(O)$_2$R, —P(O)(O$^-$)$_2$, —P(O)(OR)(O$^-$), —OP(O)(OR)(OR), —C(O)R, —C(S)R, —C(O)OR, —C(O)NRR', —C(O)O$^-$, —C(S)OR, —NRC(O)NRR', —NRC(S)NRR', —NRC(NR)NRR' and —C(NR)NRR' where R, and R' are independently hydrogen, alkyl (including substituted alkyl (alkylthio, alkylamino, etc.), cycloalkyl, substituted cycloalkyl, cycloheteroalkyl, and substituted cycloheteroalkyl, alkoxy (including substituted alkoxy), aryl (including substituted aryl, heteroaryl or substituted heteroaryl), carbonyl, alcohol, alkoxy, carbonyl, aryl, amino, amido, nitro, ethers, esters, aldehydes, sulfonyl, sulfoxyl, carbamoyl, acyl, cyano, thiocyanato, silicon moieties, halogens, sulfur containing moieties, phosphorus containing moieties, etc. or optionally R and R' together with the atoms to which they are bonded form a cycloalkyl or aryl. In some embodiments, R groups on adjacent atoms, together with the atoms to which they are joined, can form cycloalkyl (including cycloheteroalkyl) and cycloaryl (including cycloheteroaryl), which can also be further substituted as desired. In the structures depicted herein, R is hydrogen when the position is unsubstituted. It should be noted that some positions may allow two or three substitution groups, R and R', in which case the R and R' groups may be either the same or different. For example, alkyl includes "perfluoroalkyl", referring to an alkyl group where every hydrogen atom is replaced with a fluorine atom. In the context of attachment moieties, (e.g. the "Z" groups depicted herein) certain preferred alkyl substitution groups include alkenyl groups, particularly allyl and vinyl, hydroxyl, and carboxy groups.

In some embodiments, the R groups (subunits) are used to adjust the redox potential(s) of the subject compound. Thus, as is more fully described below, an R group such as a redox active subunit can be added to a macrocycle, particularly a porphyrinic macrocycle to alter it's redox potential. Certain preferred substituents include, but are not limited to, 4-chlorophenyl, 3-acetamidophenyl, 2,4-dichloro-4-trifluoromethyl). When the substituents are used for altering redox potentials, preferred substituents provide a redox potential range of less than about 5 volts, preferably less than about 2 volts, more preferably less than about 1 volt.

In certain embodiments, the R groups are as defined and depicted in the figures and the text from U.S. 60/687,464 which is incorporated herein by reference. A number of suitable proligands and complexes, as well as suitable substituents, are outlined in U.S. Pat. Nos. 6,212,093; 6,728,129; 6,451,942; 6,777,516; 6,381,169; 6,208,553; 6,657,884; 6,272,038; 6,484,394; and U.S. Ser. Nos. 10/040,059; 10/682,868; 10/445,977; 10/834,630; 10/135,220; 10/723,315; 10/456,321; 10/376,865; all of which are expressly incorporated by reference, in particular for the structures and descriptions thereof depicted therein, hereby expressly incorporated as substituent embodiments, both for the particular macrocycle the substituents are depicted within and for further substituted derivatives.

By "aryl" or grammatical equivalents herein is meant an aromatic monocyclic or polycyclic hydrocarbon moiety generally containing 5 to 14 carbon atoms (although larger polycyclic rings structures may be made) and any carbocyclic ketone or thioketone derivative thereof, wherein the carbon atom with the free valence is a member of an aromatic ring. Aromatic groups include arylene groups and aromatic groups with more than two atoms removed. For the purposes of this application aryl includes heteroaryl. "Heteroaryl" means an aromatic group wherein 1 to 5 of the indicated carbon atoms are replaced by a heteroatom chosen from nitrogen, oxygen, sulfur, phosphorus, boron and silicon wherein the atom with the free valence is a member of an aromatic ring, and any heterocyclic ketone and thioketone derivative thereof. Thus, heterocycle includes both single ring and multiple ring systems, e.g. thienyl, furyl, pyrrolyl, pyrimidinyl, indolyl, purinyl, quinolyl, isoquinolyl, thiazolyl, imidazolyl, naphthalene, phenanthroline, etc. Also included within the definition of aryl is substituted aryl, with one or more substitution groups "R" as defined herein and outlined above and herein. For example, "perfluoroaryl" is included and refers to an aryl group where every hydrogen atom is replaced with a fluorine atom. Also included is oxalyl.

The term "halogen" refers to one of the electronegative elements of group VIIA of the periodic table (fluorine, chlorine, bromine, iodine, astatine).

The term "nitro" refers to the NO₂ group.

By "amino groups" or grammatical equivalents herein is meant —NH₂, —NHR and —NRR' groups, with R and R' independently being as defined herein.

The term "pyridyl" refers to an aryl group where one CH unit is replaced with a nitrogen atom.

The term "cyano" refers to the —CN group.

The term "thiocyanato" refers to the —SCN group.

The term "sulfoxyl" refers to a group of composition RS(O)— where R is some substitution group as defined herein, including alkyl, (cycloalkyl, perfluoroalkyl, etc.), or aryl (e.g., perfluoroaryl group). Examples include, but are not limited to methylsulfoxyl, phenylsulfoxyl, etc.

The term "sulfonyl" refers to a group of composition RSO₂— where R is a substituent group, as defined herein, with alkyl, aryl, (including cycloalkyl, perfluoroalkyl, or perfluoroaryl groups). Examples include, but are not limited to methylsulfonyl, phenylsulfonyl, p-toluenesulfonyl, etc.

The term "carbamoyl" refers to the group of composition R(R')NC(O)— where R and R' are as defined herein, examples include, but are not limited to N-ethylcarbamoyl, N,N-dimethylcarbamoyl, etc.

The term "amido" refers to the group of composition R¹CON(R²)— where R¹ and R² are substituents as defined herein. Examples include, but are not limited to acetamido, N-ethylbenzamido, etc.

The term "acyl" refers to an organic acid group in which the OH of the carboxyl group is replaced by some other substituent (RCO—). Examples include, but are not limited to acetyl, benzoyl, etc.

In certain embodiments, when a metal is designated, e.g., by "M" or "M'"', where n is an integer, it is recognized that the metal can be associated with a counterion.

The phrase "provide a redox potential range of less than about X volts" refers to the fact that when a substituent providing such a redox potential range is incorporated into a compound, the compound into which it is incorporated has an oxidation potential less than or equal to X volts, where X is a numeric value.

BRIEF DESCRIPTION OF THE DRAWINGS

FIG. 13A depicts a ReAM comprising two redox active subunits, a porphyrin and a ferrocene. FIG. 13B is similar yet depicts certain possible substituents. FIG. 13C depicts a polymer of the structure in FIG. 13B, wherein h is an integer of at least two.

In FIG. 14B, a 12 membered ring, A, B, C and D can be independently selected from single and double bonds. In FIG. 14C, the cyclen has a "bridge" between two of the heteroatoms, with each A-B being independently selected from the group consisting of R₂C—CR₂, RC=CR, R₂C₂CR₂CR₂, CR=CRCR₂, CR₂CR=CR; CR₂—NR—CR₂—, —CR=N—CR₂— and —CR₂—N=CR—. FIGS. 14D-14G depict a variety of particular structures with available substituent positions. FIG. 14H depicts the "loss" of one of the "arms" of the cyclen derivative; as will be appreciated by the teachings herein. A variety of additional cyclen based derivatives may also alter the valency of the bonds and remove R groups. FIG. 14I is a macrocyclic proligand with 5 donor heteroatoms. In some instances, larger rings are used and result in polynucleate complexes. —Y— is independently selected from —(CR₂)₂—, —(CR₂)₃—, —CR=CR—, =CR—CR=, =CR—CR₂—, —CR₂—CR=, —(CR₂)₃—, =CR—CR₂CR₂—, —CR₂—CR₂—CR=, =CR—CR=CR—, —CR=CR—CR=, —CR₂—NR—CR₂—, =CR—NR—CR₂—, =CR—NR—CR=, —CR=N—CR₂—, —CR=N—CR=, —CR₂—N=CR₂—. In various embodiments R₁ and/or R₂ include, but are not limited to R₁ and/or R₂ as deficed above.

FIG. 15A depicts Z-dimension linear polymers of independently selected ReAMs 500 with independently selected linkers 510 on an electrode 505. n is an integer of 0 or more, with from 1 to 8 being preferred, and the attachment moieties are not depicted. FIG. 15B depicts Z-dimension linear polymers as in 15A with crosslinking 515. As described below, branched Z-dimension polymers are also contemplated, with 1 or multiple branch points. FIG. 15C depicts X-Y dimension linear ReAM polymers with multiple attachment moieties 520; also contemplated are surfaces comprising different linear polymers of ReAMs, again, with either homopolymers or heteropolymers being useful. Branched ReAM polymers, with optional crosslinking, are also contemplated.

FIG. 27A graphically illustrates a computer system embodying the memory devices described herein. Typically the memory device will be fabricated as a sealed "chip". Ancillary circuitry on the chip and/or in the computer permits writing bits into the memory and retrieving the written information as desired. FIG. 27B illustrates memory devices of this invention integrated into a standard computer architecture or computer system 200.

DETAILED DESCRIPTION

Figure 1:
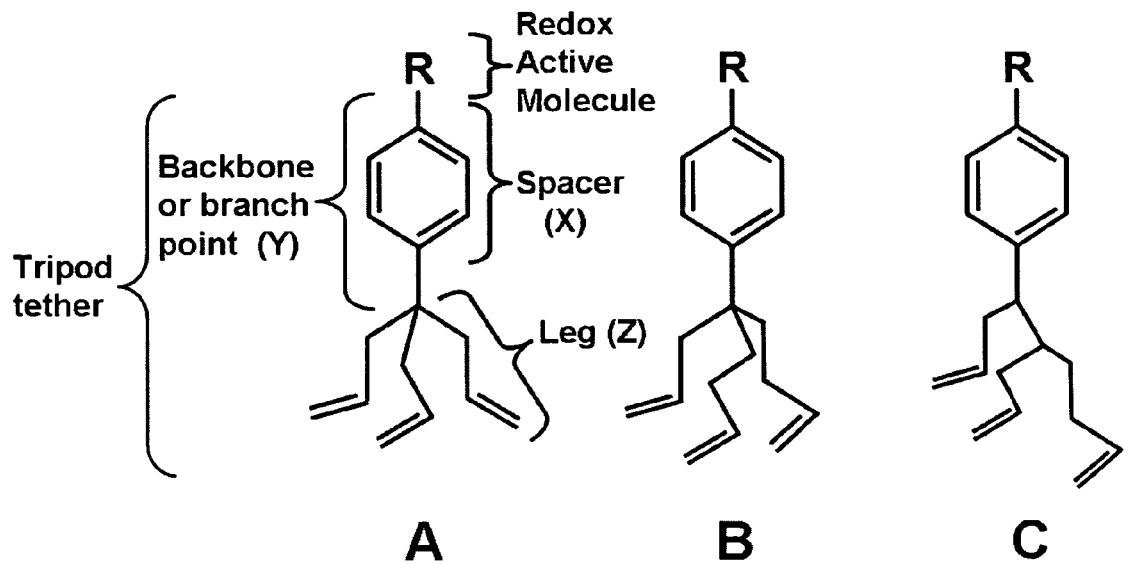
FIG. 1, panels A-C, illustrates a moiety (R) attached to three different tripodal tethers. Panel A: Tripod tether where all legs are the same length. Panel B: Tripod tethers where the legs are different lengths. Panel C: Tripod tethers where the legs attach at different points.
Figure 2:
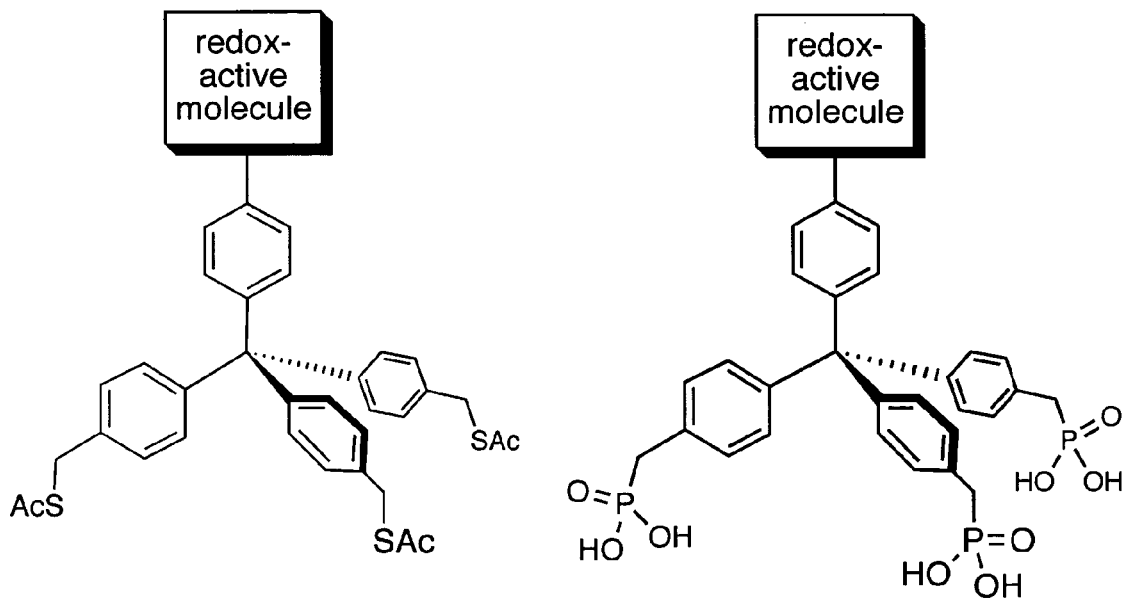
FIG. 2 illustrates tripodal tethers attached to a redox-active molecule.

I. The Use of Polypodal Tethers to Couple Redox-Active Molecules to Substrates.

The design and synthesis of redox-active molecules that are functionalized for surface attachment provides the foundation for the fabrication of information storage devices that function on the basis of stored charge (see, e.g., Roth et al. (2000) *J. Vac. Sci. Technol. B*, 18: 2359-2364; Liu et al. (2003) *Science,* 302: 1543-1545; U.S. Pat. Nos. 6,777,516, 6,728,129, 6,674,121, 6,657,884, 6,451,942, 6,381,169, 6,324,091, 6,272,038, 6,212,093, 6,208,553; PCT Publications WO 02/077633, WO 03/052835, WO 03/038886, etc.). A key feature for the commercialization of redox-based molecular information storage is that each memory cell must store sufficient charge for reliable readout. A requisite for achieving high charge densities is a relatively densely packed monolayer of redox-active molecules. Our previous studies of porphyrinic molecules tethered to both metal and semiconductor surfaces have shown that the maximum achievable surface coverages are in the mid to high $10^{-11}$ mol·cm$^{-2}$ range, which corresponds to a molecular footprint of 200-300 Å$^2$ (Roth et al. (2000) *J. Vac. Sci. Technol. B*, 18: 2359-2364; Liu et al. (2003) *Science,* 302: 1543-1545; Roth et al. (2002) *J. Phys. Chem. B*, 106: 8639-8648; Roth et al. (2003) *J. Am. Chem. Soc.*, 125: 505-517; Yasseri et al. (2004) *J. Am. Chem. Soc.*, 126: 119144-11953; Yasseri et al. (2004) *J. Am. Chem. Soc.*, 126: 15603-15612; Wei et al. (2005) *J. Phys. Chem. B*, 109: 6323-6330). This footprint is considerably larger than the 50 Å$^2$ value we have observed for porphyrins in Langmuir-Blodgett films (Schick et al. (1989) *J. Am. Chem. Soc.* 111: 1344-1350). If the molecular footprint of the redox-active molecules on the electroactive surface could be reduced to the value observed for the molecules in Langmuir-Blodgett films, the charge-storage capacity of a memory cell could be increased 4-6 fold.

This invention pertains to the discovery that the use of multipodal tethers (e.g., bipodal tethers, tripodal tethers, quadrapodal tethers, pentapodal tethers, etc.) can be used to effectively couple redox-active molecules (e.g., porphyrins, metallocenes, etc.) to a substrate (e.g., an electroactive substrate such as an electrode, an electrode on a substrate, a conductive substrate, a semiconductive substrate, etc.). Without being bound to a particular theory, it is believed that such systems yield chemisorbed species and/or SAMs in which the redox-active molecules are oriented at an angle to the substrate. Such an arrangement presumably increases surface coverage (charge density), and likely increases the stability of the chemisorbed species since fewer native surface atoms remain unbound, thus limiting substrate and/or redox-active molecule degradation pathways. In addition, multipodal tethers give a more robust attachment to the substrate.

A "polypodal tether" or "multipodal tether" (see, e.g., FIG. 1) refers to a structure comprising a "backbone" or "branch point" (see, e.g., Y in FIG. 1) to which are attached two or more "legs" (see, e.g., the "Z" moieties in FIG. 1), e.g. alkyl or arylalkyl groups (e.g., hydrocarbon chains) where the legs can each bear "feet", i.e. attachment groups to facilitate attachment of the legs to a substrate. The tether backbone can optionally comprise a spacer (see, e.g., "X", as depicted in FIG. 1) and sometimes referred to as a "linker").

"Molecules bearing an attachment group" (e.g., "feet") include molecules wherein the attachment group is an intrinsic component of the molecule, molecules derivatized to add an attachment group, and molecules derivatized so they bear a linker comprising an attachment group. Generally, suitable attachment moieties include, but are not limited to, carboxylic acids, carboxylic esters, alcohols, thiols (including S-acetylthiols) selenols, tellurols, phosphonic acids, phosphonothioates, amines, amides, trimethylsilylarenes, nitriles, aryl and alkyl groups, including substituted aryl and alkyl groups such as iodoaryl and bromomethyl, and vinyl, vinylalkyl, ethynyl and ethynylalkyl. U.S. patent application Ser. No. 10/800,147, entitled "Procedure for Preparing Redox-Active Polymers on Surfaces," by Bocian, Liu and Lindsey, assigned to the Regents of the University of California, incorporated by reference herein for this purpose, provides an extensive list of suitable attachment moieties and linkers (both independently and as "L-Z" groups), see, e.g., paragraphs 107 to 113.

As illustrated in FIG. 1, which shows a tripod tether comprising a spacer, which, in turn, is attached to a redox-active molecule (R), the tether can comprise "symmetrical" legs where each leg is the same length (see e.g., FIG. 1, panel A) or unsymmetrical legs where one or more legs are of different lengths (see, e.g., FIG. 1, panel B). While in certain embodiments, all of the legs of the tether attach at the same point (e.g., at a central carbon or heteroatom), it is also contemplated that in certain embodiments, various legs of the tether are attached at different points of, e.g., a hydrocarbon backbone (e.g., a linear hydrocarbon, a cyclic hydrocarbon, a branched hydrocarbon, etc.). Thus, for example, FIG. 1, panel C, illustrates a tripodal tether where two of the legs attach at different points. In this regard, it is noted that where the attachment is represented, e.g., by a Y, where the Y is an atom or a hydrocarbon backbone (e.g., an alkyl), when the Y is an atom, the legs are attached at a single molecule, but where the Y is a backbone comprising a plurality of molecules, the legs can be attached at a single molecule (e.g., a single carbon) or two or more of the legs can be attached at different atoms.

As illustrated in FIG. 1, the multipodal tethers of this invention can, optionally, comprise a linker. Linkers are used in a variety of configurations in the present invention, including to link attachment moieties (e.g., multipodal tethers) to one or more redox-active molecules (ReAMs) of the invention, for linking together redox active subunits of ReAMs, and in polymerization of ReAMs. Linkers are used in order to achieve fast writing and/or erasing at low voltages and a small cell size. The scaling of the linkers for use in the present invention can be optimized. Optimum linker size can be calculated theoretically (see, e.g., U.S. Ser. No. 60/473,782, hereby expressly incorporated by reference). Alternatively linkers (and in fact, the suitability of ReAMs as well) can be evaluated empirically simply by coupling the ReAM to the surface as described herein and in the cited references, and performing voltammetry to evaluate the electrochemical properties of the attached polymer.

While polypodal tethers having essentially any number of "legs" (e.g., 5, 6, 7, 8, 9, 10, 20, 25, 30, 50, or more, etc.) are contemplated within the scope of this invention, it is expected that tethers providing a smaller "footprint" permit the formation of surface coverages having a higher charge density. Thus, in certain embodiments, the use of bipodal, tripodal, quadrapodal, and/or pentapodal tethers is contemplated.

It is also noted that, in certain embodiments, not all of the "legs" of the polypodal tether need be coupled to a substrate. The mere presence of one or more uncoupled "legs" can still act to facilitate orientation of the redox-active molecules (ReAMs) to provide better surface attachment and/or a higher charge density. Thus for example, in certain embodiments a tripodal tether may be coupled to a substrate by one or two of the "legs" of the tether. In certain embodiments the tripodal tether can be coupled to a substrate by all three "legs".

When a polypodal tether is coupled to a substrate (e.g., ionically coupled, covalently coupled, etc.) the attachment can be through a single reactive group ("foot") on the "leg" (a substrate attachment group) or through a plurality of such reactive groups on the "leg". In certain embodiments the attachment is through a single reactive group on the leg forming, e.g., a covalent linkage to the substrate.

A wide variety of polypodal tethers are contemplated for use in the present invention. Thus, for example, in certain embodiments the polypodal tether is a 2-podal, 3-podal, 4-podal, or 5-podal tether. In various embodiments the legs of the tether do not contain a benzene and, in various embodiments, each leg of the tether contains at least one carbon and not more than 10 carbons.

In certain embodiments the tether is a tripod tether where the redox-active molecule attached to the tripod tether can be represented by Formula I:

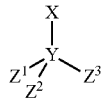

I where X is a redox-active molecule/moiety (ReAM) as described herein, e.g., a macrocycle such as a porphyrinic macrocycle, a sandwich compound of porphyrinic macrocycles, a metallocene, etc.; Y includes, but is not limited to a heteroatom, a carbon, a straight chain substituted or unsubstituted hydrocarbon, a branched hydrocarbon, a cyclic hydrocarbon, a heterocyclic compound, an aryl compound, a heteroaryl compound, a non-hydrocarbon, and the like; $Z^1$, $Z^2$, and $Z^3$ are independently selected and include, but are not limited to alkyl, aryl, heterocycle, vinylalkyl, allylalkyl, ethynylalkyl, hydroxyalkyl, carboxyalkyl, carboxy, cyanoalkyl, aminoalkyl, formylalkyl, bromoalkyl, iodoalkyl, chloroalkyl, mercaptoalkyl, selenylalkyl, tellurylalkyl, phosphonoalkyl, and the like; and when Y is a hydrocarbon, at least two of $Z^1$, $Z^2$, and $Z^3$ are attached to different carbons. In various embodiments Y is a two carbon hydrocarbon (e.g., alkyl, hydroxyalkyl, etc.), a 3 carbon hydrocarbon, a 4 carbon hydrocarbon, etc. In various embodiments Y is carbon or a heteroatom.

In certain embodiments, at least one, at least two, or at least 3 of the legs of the tripod tether are selected from the group consisting of an alcohol, a hydroxyalkyl, an alkyl, an allyl, an allyl-terminated hydrocarbon, an alkyne, an alkyne-terminated hydrocarbon, and an ethyleneoxy unit (—CH$_2$CH$_2$—O—). In various embodiments at least two of the legs are identical, and in certain embodiments at least three of the legs are identical. In various embodiments the alkyl leg(s) comprise a substituted alkyl (e.g., an alkylallyl). In certain embodiments the redox-active molecule attached to the tripod tether can be represented by Formula II:

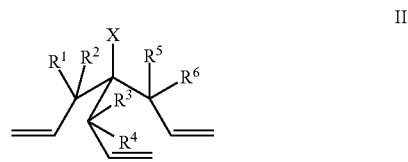

II where $R^1$, $R^2$, $R^3$, $R^4$, $R^5$, and $R^6$ can be a variety of independently selected substituents, e.g., H, OH, alkyl, methyl, and the like. In certain embodiments $R^1$, $R^2$, $R^3$, $R^4$, $R^5$, and $R^6$ are all H.

In various embodiments one or more of the legs of the tripod are a hydroxyalkyl. Where all three legs are hydroxyl, certain embodiments, can be represented by Formula III:

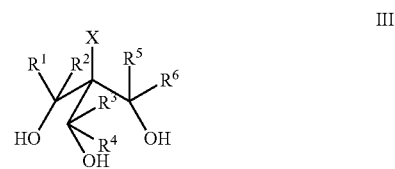

III where $R^1$, $R^2$, $R^3$, $R^4$, $R^5$, and $R^6$ can be a variety of independently selected substituents, e.g., H, alkyl (e.g. methyl, etc.), and the like. In certain embodiments $R^1$, $R^2$, $R^3$, $R^4$, $R^5$, and $R^6$ are all H.

In various embodiments at least one of the legs of said tripod tether is an aryl (e.g., a substituted aryl). Suitable substituted aryls include, but are not limited to, a substituent such as S-acetylthioalkyl, phosphonoalkyl, vinyl, allyl, ethynyl, propargyl, hydroxy, carboxy, cyano, amino, formyl, bromo, iodo, chloro, mercapto, selenyl, telluryl, phosphono, S-acetylthio, Se-acetylseleno, Te-acetyltelluro, and the like.

In various embodiments the redox-active molecule attached to a tripodal tether can be represented by Formula IV:

IV where $L^1$, $L^2$, and $L^3$ are independently selected and include, but are not limited to a C, a hydrocarbon (e.g., a substituted or unsubstituted alkyl, etc.), preferably a hydrocarbon consisting of no more than 2, 3, 4, 5, 8, 10, or 20 carbons; and $A^1$, $A^2$, and $A^3$ are independently selected surface attachment groups, e.g., bromo, iodo, hydroxy, hydroxymethyl, formyl, bromomethyl, vinyl, allyl, thiol, selenyl, S-acetylthio, S-acetylthio, mercapto, mercaptomethyl, ethyne, and the like. It is noted that the legs of the multipodal tethers designated as $Z^1$, $Z^2$, and $Z^3$ in Formula I include legs (L) and surface attachment groups (A) as shown in Formula IV.

In certain embodiments the redox-active molecule attached to a tripodal tether can be represented by Formula V:

V

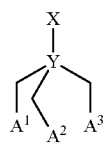

where Y and $A^1$, $A^2$, and $A^3$ are as described above.

In certain embodiments the redox-active molecule attached to a tripodal tether can be represented by Formula VI or Formula VII:

VI

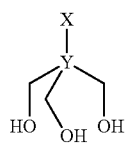

VII

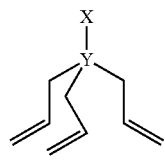

where Y is an atom or a tether backbone as described herein and X is a redox-active molecule as described herein, e.g., a porphyrinic macrocycle, a sandwich compound of porphyrinic macrocycles, a metallocene, etc.

In certain embodiments the polypodal tether is a biopodal tether. In various embodiments the redox-active molecule is attached to a bipodal tether and the redox-active molecule attached to a bipodal tether can be represented by Formula VIII:

VIII

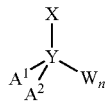

where X is a redox-active molecule as described herein, e.g., a porphyrinic macrocycle, a sandwich compound of porphyrinic macrocycles, a metallocene, etc., Y is an atom or a tether backbone as described herein, Z is a carbon or a heteroatom; and $A^1$ and $A^2$ are independently selected substrate binding groups. W is present or absent (i.e., n is 0 or 1) and when present can be an activating or directing group, e.g., to facilitate synthesis, or it can also be H or alkyl or aryl or other substituent. In various embodiments W includes, but is not limited to cyano, alkyl, sulfonyl, acyl, carboxyl, carboxyalkyl, carboxyaryl, arylsulfonyl, aldehyde, H, alkyl, aryl and the like.

W can be present, or absent, or removed. Thus, in certain embodiments the redox-active molecule attached to a bipod tether can be represented by Formula IX:

IX

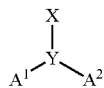

where Y is an atom or a tether backbone as described herein (e.g., N, P, B, As, CH, C-alkyl, C-aryl, and C-heterocyclic, etc.). $A^1$ and $A^2$ are independently selected substrate binding groups, e.g., bromo, iodo, hydroxy, hydroxymethyl, formyl, bromomethyl, vinyl, allyl, thiol, selenyl, S-acetylthio, S-acetylthio, mercapto, mercaptomethyl, ethyne, and the like. It will be appreciated that when substrate binding groups are shown and comprise, for example a leaving group, the compound even though described coupled to a surface may still be represented with the leaving group present recognizing that the leaving group may be absent when the composition is so coupled.

Y can, optionally comprise a spacer. When present, in certain embodiments the spacer is selected to provide some rigidity and to facilitate support of the redox-active molecule above an underlying substrate. Suitable spacers Y include, but are not limited to an aromatic group, a heterocycle, an aryl, an alkyl, a linear aliphatic, a branched aliphatic, a cyclic aliphatic, a coordination compound, a heteroaromatic group, and the like.

Certain illustrative redox-active molecules attached to various multipodal linkers are shown by Formulas X through XIII:

X

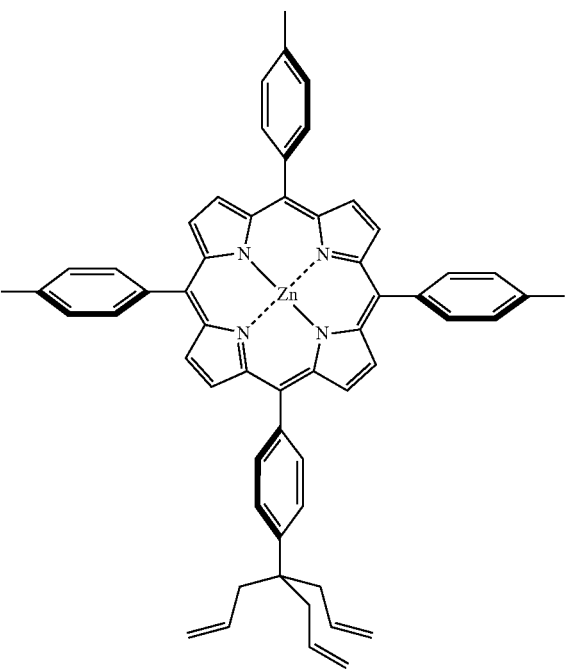

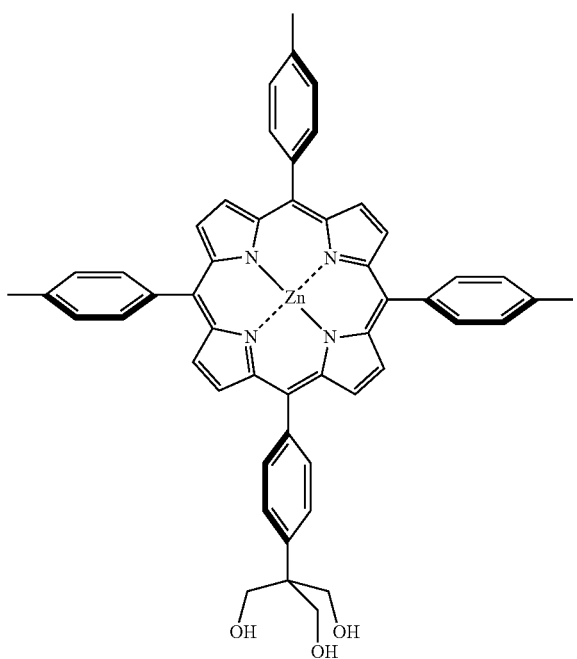

XI

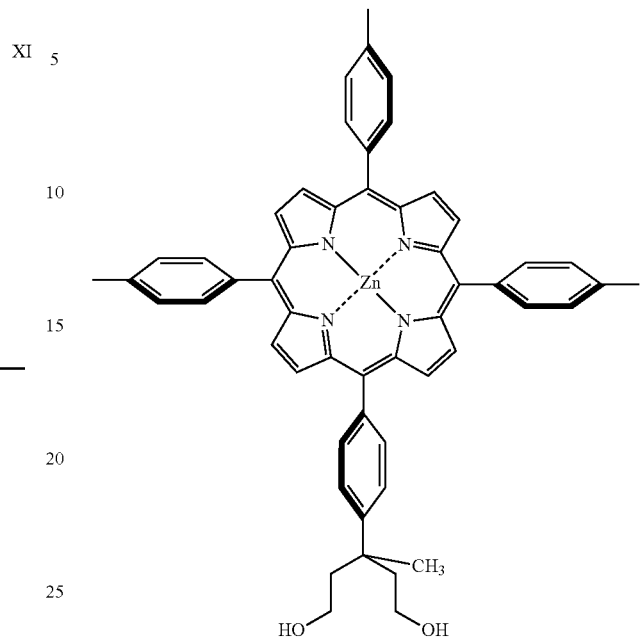

XIII

Other suitable tripodal tethers are listed in Table I.

Table 1. Compact tripod tethers for attachment of redox-active molecules. Each entity listed in Table 1 is a tether, which consists of feet, the branching site, and optionally, a linker. For example, the second item in Table 1, 4-(3-vinylpenta-1,4-dien-3-yl)phenyl consists of three terminal vinyl groups attached to a tetrahedral carbon; the tetrahedral carbon is attached to the phenyl group. The vinyl groups are the feet, the tetrahedral carbon is the branch site, and the phenyl group is the linker. The first item in Table 1 is 3-vinylpenta-1,4-dien-3-yl, which consists of three terminal vinyl groups attached to a tetrahedral carbon.

Alkene Surface Attachment Groups (2, 3, 4 Carbons):
3-vinylpenta-1,4-dien-3-yl
4-(3-vinylpenta-1,4-dien-3-yl)phenyl
4-(3-vinylpenta-1,4-dien-3-yl)biphen-4'-yl
4-allylhepta-1,6-dien-4-yl
4-(4-allylhepta-1,6-dien-4-yl)phenyl
4-(4-allylhepta-1,6-dien-4-yl)biphen-4'-yl
5-(1-buten-4-yl)nona-1,8-dien-5-yl
4-[5-(1-buten-4-yl)nona-1,8-dien-5-yl]phenyl
4-[5-(1-buten-4-yl)nona-1,8-dien-5-yl]biphen-4'-yl Alkyne Surface Attachment Groups (2, 3, 4 Carbons):
3-ethynylpenta-1,4-diyn-3-yl
4-(3-ethynylpenta-1,4-diyn-3-yl)phenyl
4-(3-ethynylpenta-1,4-diyn-3-yl)biphen-4'-yl
4-propargylhepta-1,6-diyn-4-yl
4-(4-propargylhepta-1,6-diyn-4-yl)phenyl
4-(4-propargylhepta-1,6-diyn-4-yl)biphen-4'-yl
5-(1-butyn-4-yl)nona-1,8-diyn-5-yl
4-[5-(1-butyn-4-yl)nona-1,8-diyn-5-yl]phenyl
4-[5-(1-butyn-4-yl)nona-1,8-diyn-5-yl]biphen-4'-yl Alcohol Surface Attachment Groups (1, 2, 3 Carbons):
2-(hydroxymethyl)-1,3-dihydroxyprop-2-yl
4-[2-(hydroxymethyl)-1,3-dihydroxyprop-2-yl]phenyl
4-[2-(hydroxymethyl)-1,3-dihydroxyprop-2-yl]biphen-4'-yl
3-(2-hydroxyethyl)-1,5-dihydroxypent-3-yl
4-[3-(2-hydroxyethyl)-1,5-dihydroxypent-3-yl]phenyl
4-[3-(2-hydroxyethyl)-1,5-dihydroxypent-3-yl]biphen-4'-yl 4-(3-hydroxypropyl)-1,7-dihydroxyhept-4-yl
4-[4-(3-hydroxypropyl)-1,7-dihydroxyhept-4-yl]phenyl
4-[4-(3-hydroxypropyl)-1,7-dihydroxyhept-4-yl]biphen-4'-yl
Thiol Surface Attachment Groups (1, 2, 3 Carbons):
2-(mercaptomethyl)-1,3-dimercaptoprop-2-yl
4-[2-(mercaptomethyl)-1,3-dimercaptoprop-2-yl]phenyl,
4-[2-(mercaptomethyl)-1,3-dimercaptoprop-2-yl]biphen-4'-yl
3-(2-mercaptoethyl)-1,5-dimercaptopent-3-yl
4-[3-(2-mercaptoethyl)-1,5-dimercaptopent-3-yl]phenyl
4-[3-(2-mercaptoethyl)-1,5-dimercaptopent-3-yl]biphen-4'-yl
4-(3-mercaptopropyl)-1,7-dimercaptohept-4-yl
4-[4-(3-mercaptopropyl)-1,7-dimercaptohept-4-yl]phenyl
4-[4-(3-mercaptopropyl)-1,7-dimercaptohept-4-yl]biphen-4'-yl
Selenyl Surface Attachment Groups (1, 2, 3 Carbons):
2-(selenylmethyl)-1,3-diselenylprop-2-yl
4-[2-(selenylmethyl)-1,3-diselenylprop-2-yl]phenyl
4-[2-(mercaptomethyl)-1,3-dimercaptoprop-2-yl]biphen-4'-yl
3-(2-selenylethyl)-1,5-diselenylpent-3-yl
4-[3-(2-selenylethyl)-1,5-diselenylpent-3-yl]phenyl
4-[3-(2-selenylethyl)-1,5-diselenylpent-3-yl]biphen-4'-yl
4-(3-selenylpropyl)-1,7-diselenylhept-4-yl
4-[4-(3-selenylpropyl)-1,7-diselenylhept-4-yl]phenyl
4-[4-(3-selenylpropyl)-1,7-diselenylhept-4-yl]biphen-4'-yl
Phosphono Surface Attachment Groups (1, 2, 3 Carbons):
2-(phosphonomethyl)-1,3-diphosphonoprop-2-yl
4-[2-(phosphonomethyl)-1,3-diphosphonoprop-2-yl]phenyl
4-[2-(phosphonomethyl)-1,3-diphosphonoprop-2-yl]biphen-4'-yl
3-(2-phosphonoethyl)-1,5-diphosphonopent-3-yl
4-[3-(2-phosphonoethyl)-1,5-diphosphonopent-3-yl]phenyl
4-[3-(2-phosphonoethyl)-1,5-diphosphonopent-3-yl]biphen-4'-yl
4-(3-phosphonopropyl)-1,7-diphosphonohept-4-yl
4-[4-(3-phosphonopropyl)-1,7-diphosphonohept-4-yl]phenyl
4-[4-(3-phosphonopropyl)-1,7-diphosphonohept-4-yl]biphen-4'-yl
Carboxylic Acid Surface Attachment Groups (1, 2, 3 Carbons):
2-(carboxymethyl)-1,3-dicarboxyprop-2-yl
4-[2-(carboxymethyl)-1,3-dicarboxyprop-2-yl]phenyl
4-[2-(carboxymethyl)-1,3-dicarboxyprop-2-yl]biphen-4'-yl
3-(2-carboxyethyl)-1,5-dicarboxypent-3-yl
4-[3-(2-carboxyethyl)-1,5-dicarboxypent-3-yl]phenyl
4-[3-(2-carboxyethyl)-1,5-dicarboxypent-3-yl]biphen-4'-yl
4-(3-carboxypropyl)-1,7-dicarboxyhept-4-yl
4-[4-(3-carboxypropyl)-1,7-dicarboxyhept-4-yl]phenyl
4-[4-(3-carboxypropyl)-1,7-dicarboxyhept-4-yl]biphen-4'-yl The polypodal tethers can be fabricated/synthesized by any of a number of methods. Thus, for example, in certain embodiments, a redox-active molecule (e.g., a porphyrin) bearing a triallyl tripod incorporates a p-phenylene group between the porphyrin and the central carbon of the tripod. A p-tolyl group is provided at each of the three non-linking meso-positions of the porphyrin. The synthesis of the resulting $A_3B$-porphyrin can be achieved via the condensation of a dipyrromethane-dicarbinol with the dipyrromethane bearing the tripod (see, e.g., Example 1).

In another approach, a polypodal tether can be coupled to a redox-active molecule by performing a Suzuki coupling reaction, e.g., of a boronic ester porphyrinic macrocycle and a masked polypodal tether aromatic bromo compound. Thus, for example, the synthesis of a zinc porphyrin bearing three alcohol groups in a tripodal architecture via a Suzuki coupling reaction of a meso-substituted boronic ester porphyrin and a masked tripodal alcohol aromatic bromo compound is illustrated in Example 2.

Preparation of redox-active molecules bearing a bipodal tether group, can be accomplished by making use of an aryl-bonded activating group, such as cyano, carbalkoxy, alkyl- or aryl sulfonyl, etc., in such a way to facilitate the creation of the key arylalkyl quaternary carbon center that serves as the anchoring point for the bipodal chains. The selected activating groups allow for the introduction of the bipodal tether chains in more than one way. Thus, for example, one can resort to the use of standard alkylation conditions, 1,4-addition reactions, even phase transfer conditions, and the like (see, e.g., Example 3).

Using the teachings provided herein, the preparation of other redox-active moieties attached to various polypodal tethers can routinely be achieved.

II. Arrays of Electrodes Bearing Redox-Active Molecules Attached to Polypodal Linkers.

In certain embodiments, e.g., particularly when used in memory devices the redox-active molecules are typically coupled to a substrate, e.g., one or more electrodes, semiconductors, etc. using the polypodal tethers described herein. It is noted that in certain embodiments, the redox-active molecule can be coupled to a substrate by a different linker and, in such instances, the polypodal tether can simply act as a spacer to raise the redox-active moiety above the underlying surface.

Thus, in certain embodiments the information storage molecules are typically ultimately coupled to a surface. The surface can be an inert and/or non-conductive surface. More typically, however, the surface will be the surface of an electrode and/or a counterelectrode and/or a semiconductor.

The electrode and/or counter electrodes are typically fabricated of materials capable of conducting electrons. The electrodes and/or counterelectrodes can comprise conductors, semiconductors, superconductors, and the like. In certain embodiments, the electrodes and/or counterelectrodes have a resistivity of less than about $10^{-2}$ ohm-meters, preferably less than about $10^{-3}$ ohm-meters, more preferably less than about $10^{-4}$ ohm-meters, and most preferably less than about $10^{-5}$, or $10^{-6}$ ohm-meters.

Certain preferred electrodes and/or counterelectrodes include metals and/or metal oxides (e.g., W, Sn, Si). In certain embodiments particularly preferred electrodes comprise a material such as ruthenium, osmium, cobalt, rhodium, rubidium, lithium, sodium, potassium, vanadium, cesium, beryllium, magnesium, calcium, chromium, molybdenum, silicon, germanium, aluminum, iridium, nickel, palladium, platinum, iron, copper, titanium, tungsten, silver, gold, zinc, cadmium, indium tin oxide, titanium nitride, titanium oxide, tantalum, tantalum nitride and tantalum oxide, carbon, a carbon nanotube, and the like.

Suitable semiconductors include, but are not limited to Si, Ge, Sn, Se, Te, B, diamond, P, B—C, B—P(BP6), B—Si, Si—C, Si—Ge, Si—Sn and Ge—Sn, SiC, BN/BP/BAs, AlN/AlP/AlAs/AlSb, GaN/GaP/GaAs/GaSb, InN/InP/InAs/InSb, BN/BP/BAs, AlN/AlP/AlAs/AlSb, GaN/GaP/GaAs/GaSb, InN/InP/InAs/InSb, ZnO/ZnS/ZnSe/ZnTe, CdS/CdSe/CdTe, HgS/HgSe/HgTe, BeS/BeSe/BeTe/MgS/MgSe, GeS, GeSe, GeTe, SnS, SnSe, SnTe, PbO, PbS, PbSe, PbTe, CuF, CuCl, CuBr, CuI, AgF, AgCl, AgBr, AgI, $BeSiN_2$, $CaCN_2$, $ZnGeP_2$, $CdSnAs_2$, $ZnSnSb_2$, $CuGeP_3$, $CuSi_2P_3$, (Cu, Ag)(Al, Ga, In, Tl, Fe)(S, Se, Te)$_2$, $Si_3N_4$, $Ge_3N_4$, $Al_2O_3$, (Al, Ga, In)$_2$(S, Se, Te)$_3$, $Al_2CO$, and/or an appropriate combination of two or more such semiconductors. The semiconductors can optionally include one or more dopants (e.g., including, but not limited to a p-type dopant from Groups II, III, or IV of the periodic table; an n-type dopant from Group V of the periodic table).

The redox-active molecules are typically electrically coupled to one or more electrodes to permit setting and/or reading of the oxidation state of the redox-active molecules.

Thus, in certain embodiments, this invention contemplates a composition comprising an array of electrodes where a plurality of the electrodes each comprise one or more redox-active molecule(s) attached to an electrode by a polypodal tether, e.g., as described herein. In various embodiments the redox-active molecules are disposed in the array at various discrete locations to form thereby an electrochemical "storage" cell/memory element. It will be appreciated that in certain embodiments, this invention contemplates a composition comprising an array of storage molecules forming thereby an array of storage cells (memory elements) a plurality of which are independently addressable. The storage molecules can be attached/chemisorbed to electrodes present on a substrate, or to the substrate itself. In certain embodiments the array comprises at least $10^3$, preferably at least $10^4$, more preferably at least $10^5$, and most preferably at least $10^7$, $10^8$, or $10^9$ such storage cells. In certain embodiments the array provides an electrochemical "storage cell/memory element" at a density of at least $10^3/cm^2$, preferably at least $10^4/cm^2$, more preferably at least $10^5/cm^2$, and most preferably at least $10^7/cm^2$, $10^8/cm^2$, $10^9/cm^2$, $10^{10}/cm^2$, $10^{11}/cm^2$, $10^{12}/cm^2$, $10^{13}/cm^2$, or $10^{15}/cm^2$.

In various embodiments each storage cell/location is addressed by at least one electrode, and more preferably by at least two electrodes (e.g., a working electrode and a counter electrode). In various embodiments the working electrode and/or counter electrode can be common to a plurality of storage locations, but the combination of electrodes are preferentially disposed to provide independent setting and/or reading of the oxidation states of a plurality of storage locations.

The architecture of various arrays of redox-active moieties is described in Roth et al. (2000) *J. Vac. Sci. Technol. B*, 18: 2359-2364; Liu et al. (2003) *Science*, 302: 1543-1545; U.S. Pat. Nos. 6,777,516, 6,728,129, 6,674,121, 6,657,884, 6,451,942, 6,381,169, 6,324,091, 6,272,038, 6,212,093, 6,208,553; PCT Publications WO 02/077633, WO 03/052835, WO 03/038886, and the like.

It is noted that, in certain embodiments, the electrode(s) and/or counterelectrode(s) can be functionalized to contain a chemical group that can be derivatized or crosslinked (e.g., a sulfate, a sulfhydryl, an amine, an aldehyde, a carboxylic acid, a phosphate, a phosphonate, an alkene, an alkyne, a hydroxyl group, a bromine, an iodine, a chlorine, a light-activatable group, a group activatable by an electric potential, etc.).

III. Redox-Active Molecules (Information Storage Molecules).

The compositions described herein can be used to synthesize a wide variety of hybrid components and/or devices (e.g., field effect transistors, sensors, memory elements, memory chips, etc.). In certain embodiments, the methods are used to assemble hybrid memory devices where information is stored in a redox-active information storage molecule (e.g., a ReAM). Certain preferred redox-active molecules suitable for use in this invention are characterized by having a multiplicity of oxidation states. In various embodiments those oxidation states can be provided by one or more redox-active units. A redox-active unit refers to a molecule or to a subunit of a molecule that has one or more discrete oxidation states that can be set by application of an appropriate voltage. Thus, for example, in one embodiment, the redox-active molecule can comprise two or more (e.g., 8) different and distinguishable oxidation states with 4, 6 and 8, 16, or 32 oxidation states being of particular significance. Typically, but not necessarily, such multi-state molecules will be composed of several redox-active units (e.g., porphyrins, metallocenes, etc.). Each redox-active molecule is itself at least one redox-active unit, or comprises at least one redox-active unit, but can easily comprise two or more redox-active units.

There are a number of redox-active moieties (ReAMs) useful in the present invention. Such ReAMs include, but are not limited to those based on polydentate proligands, including, but not limited to macrocyclic and non-macrocyclic moieties. A number of suitable proligands and complexes, as well as suitable substituents, are outlined in U.S. Pat. Nos. 6,212,093; 6,728,129; 6,451,942; 6,777,516; 6,381,169; 6,208,553; 6,657,884; 6,272,038; 6,484,394; and U.S. Ser. Nos. 10/040,059; 10/682,868; 10/445,977; 10/834,630; 10/135,220; 10/723,315; 10/456,321; 10/376,865; all of which are expressly incorporated by reference, in particular for the structures and descriptions thereof depicted therein.

Suitable proligands include, but are not limited to ligands that use nitrogen, oxygen, sulfur, carbon or phosphorus atoms (depending on the metal ion) as the coordination atoms (generally referred to in the literature as sigma ($\sigma$) donors) and organometallic ligands such as metallocene ligands (generally referred to in the literature as pi ($\pi$) donors).

In various embodiments the ReAM is or comprises a macrocyclic ligand, that can include macrocyclic proligands and/or macrocyclic complexes. A typical macrocyclic proligand comprises a cyclic moiety that contains donor atoms (sometimes referred to herein as "coordination atoms") oriented so that they can bind to a metal ion. A typical macrocyclic complex comprises a macrocyclic proligand with at least one metal ion. In some embodiments the macrocyclic complex comprises a single metal ion, although as described below, polynuclear complexes, including polynucleate macrocyclic complexes, are also contemplated.

Figure 11:
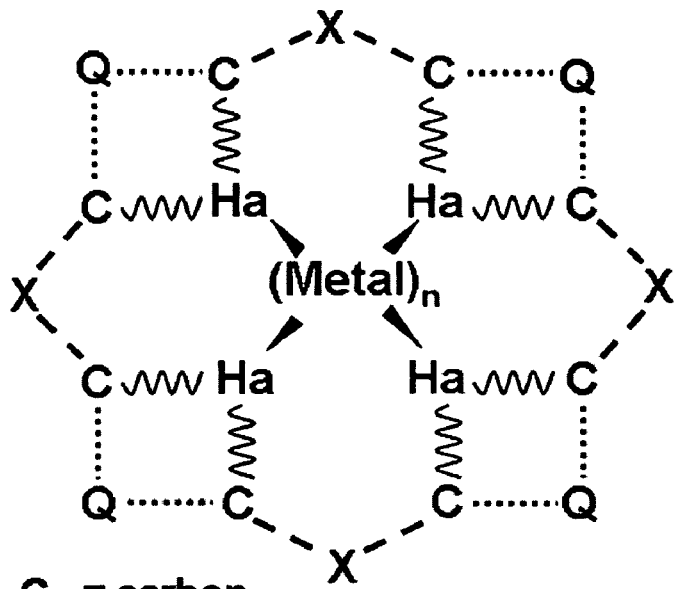
FIG. 11 depicts a broad macrocyclic ligand (e.g. the proligand (when q is 0) or the complex (when q is 1).
Figure 12A:
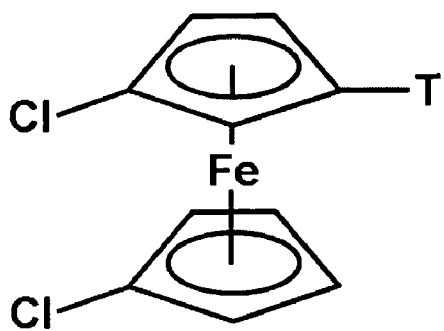
FIGS. 12A through 12F illustrate various ferrocenes, where T denotes a tether (e.g., a multipodal tether).
Figure 12B:
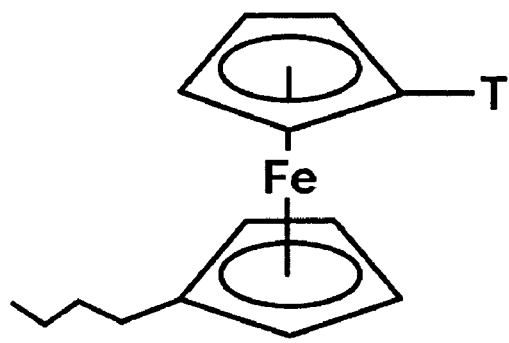
Figure 12C:
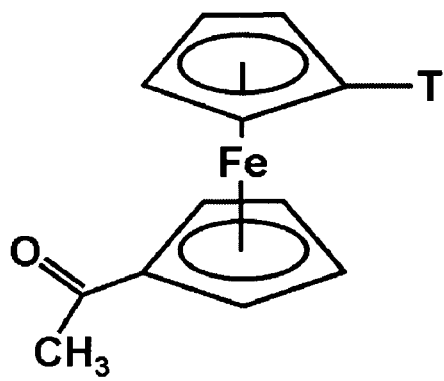
Figure 12D:
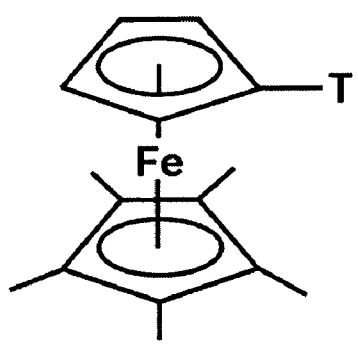
Figure 12E:
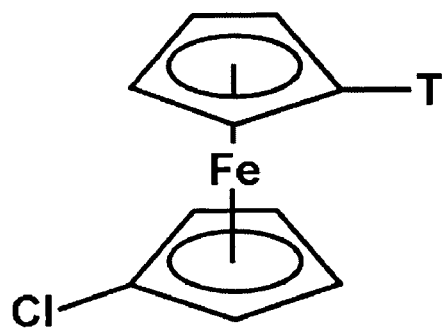
Figure 12F:
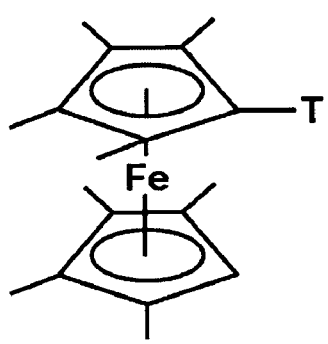

A broad schematic of a suitable macrocyclic ligand is shown and described in FIG. 11. In this embodiment, roughly based on porphyrins, a 16 member ring (when the —X-moiety contains a single atom, either carbon or a heteroatom), 17 membered rings (where one of the —X-moieties contains two skeletal atoms), 18 membered rings (where two of the —X-moieties contains two skeletal atoms), 19 membered rings (where three of the —X-moieties contains two skeletal atoms) or 20 membered rings (where all four of the —X-moieties contains two skeletal atoms), are all contemplated. Each —X-group is independently selected. The ••••Q•••• moiety, together with the skeletal —C-heteroatom-C (with either single or double bonds independently connecting the carbons and heteroatom) for 5 or 6 membered rings that are optionally substituted with 1 or 2 (in the case of 5 membered rings) or 1, 2, or 3 (in the case of 6 membered rings) with independently selected $R^2$ groups. In some embodiments, the rings, bonds and substituents are chosen to result in the compound being electronically conjugated, and at a minimum to have at least two oxidation states.

In some embodiments, the macrocyclic ligands of the invention are selected from the group consisting of porphyrins (particularly porphyrin derivatives as defined below), and cyclen derivatives.

Porphyrins and Porphyrinic Macrocycles.

One particularly preferred subset of macrocycles suitable in the invention are prophoryrinic macrocycles including porphyrins, and porphyrin derivatives. Such derivatives include porphyrins with extra rings ortho-fused, or ortho-perifused, to the porphyrin nucleus, porphyrins having a replacement of one or more carbon atoms of the porphyrin ring by an atom of another element (skeletal replacement), derivatives having a replacement of a nitrogen atom of the porphyrin ring by an atom of another element (skeletal replacement of nitrogen), derivatives having substituents other than hydrogen located at the peripheral meso-, β-, or core atoms of the porphyrin, derivatives with saturation of one or more bonds of the porphyrin (hydroporphyrins, e.g., chlorins, bacteriochlorins, isobacteriochlorins, decahydroporphyrins, corphins, pyrrocorphins, etc.), derivatives having one or more atoms, including pyrrolic and pyrromethenyl units, inserted in the porphyrin ring (expanded porphyrins), derivatives having one or more groups removed from the porphyrin ring (contracted porphyrins, e.g., corrin, corrole) and combinations of the foregoing derivatives (e.g. phthalocyanines, sub-phthalocyanines, and porphyrin isomers). Additional suitable porphyrin derivatives include, but are not limited to the chlorophyll group, including etiophyllin, pyroporphyrin, rhodoporphyrin, phylloporphyrin, phylloerythrin, chlorophyll a and b, as well as the hemoglobin group, including deuteroporphyrin, deuterohemin, hemin, hematin, protoporphyrin, mesohemin, hematoporphyrin, mesoporphyrin, coproporphyrin, uruporphyrin and turacin, and the like.

As is true for the compounds outlined herein, and as will be appreciated by those in the art, each unsaturated position, whether carbon or heteroatom, can include one or more substitution groups as defined herein, depending on the desired valency of the system.

Certain preferred redox-active molecules include a porphyrin, an expanded porphyrin, a contracted porphyrin, a linear porphyrin polymer, a porphyrin sandwich coordination complex, a porphyrin array, and the like. These structures and methods of synthesis are described in detail in U.S. Pat. Nos. 6,777,516, 6,728,129, 6,674,121, 6,657,884, 6,451,942, 6,381,169, 6,324,091, 6,272,038, 6,212,093, 6,208,553; PCT Publications WO 02/077633, WO 03/052835, WO 03/038886, which are incorporated herein by reference.

In addition, included within the definition of "porphyrin" are porphyrin complexes, which comprise a porphyrin proligand and at least one metal ion. Suitable metals for the porphyrin compounds will depend on the heteroatoms used as coordination atoms, but in general are selected from transition metal ions. The term "transition metals" as used herein typically refers to the elements in groups 3 through 12 of the periodic table. Typically transition metals are characterized by the fact that their valence electrons, or the electrons they use to combine with other elements, are present in more than one shell and consequently often exhibit several common oxidation states. In certain embodiments, the transition metals of this invention include, but are not limited to one or more of scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, and/or oxides, and/or nitrides, and/or alloys, and/or mixtures thereof.

In certain embodiments a suitable redox-active molecule is a porphyrin illustrated by Formula XIV:

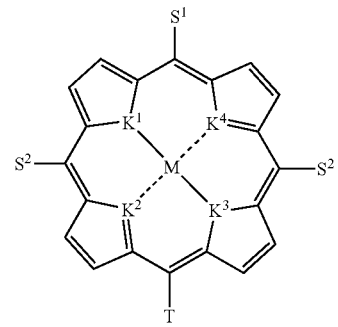

XIV where M is present or absent and when present is a metal or a metalloid; $K^1$, $K^2$, $K^3$, and $K^4$ are independently selected and can include, but are not limited to a group IV element, a group V element, a group VI element, and CH; $S^1$, $S^2$, and $S^3$ are independently selected substituents and/or redox-active units/subunits. T is an optionally present tether (e.g., a multipodal tether as described herein).

In certain embodiments, where $S^1$ and/or $S^2$ and/or $S^3$ comprise a redox active unit or subunit, $S^1$, and/or $S^2$, and/or $S^3$ can be described by the formula -J-F where F is a redox-active subunit (e.g. a metallocene, a porphyrin, etc.) and J is an optionally present linker.

In certain embodiments, where $S^1$ and/or $S^2$ and/or $S^3$ are substituents as described herein, $S^1$, and/or $S^2$, and/or $S^3$ are independently selected from the group consisting of aryl, phenyl, cycloalkyl, alkyl, halogen, alkoxy, alkylthio, perfluoroalkyl, alkenyl, alkynyl, perfluoroaryl, pyridyl, cyano, thiocyanato, nitro, amino, alkylamino, acyl, sulfoxyl, sulfonyl, imido, amido, imidazolyl, and carbamoyl. Typically in certain embodiments $S^1$, and/or $S^2$, and/or $S^3$ are selected to provide a redox potential range of less than about 2 volts. In various embodiments $K^1$, $K^2$, $K^3$, and $K^4$ are independently selected and can include, but are not limited to N, O, S, Se, Te, and CH. In various embodiments M is present and is a metal (e.g., Zn, Mg, Cd, Hg, Cu, Ag, Au, Ni, Pd, Pt, Co, Rh, Ir, Mn, B, Al, Ga, Pb, and Sn). In certain embodiments M is Zn, Mg, or Ni. In various embodiments $S^1$, $S^2$, and $S^3$ are all the same, and/or $K^1$, $K^2$, $K^3$, and $K^4$ are all the same. In certain embodiments $K^1$, $K^2$, $K^3$, and $K^4$ are all N.

In certain preferred embodiments, a substituted aryl group is attached to the porphyrin, and the substituents on the aryl group are selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl.

The porphyrin in Formula XIV can be attached via an optional spacer (X) to a polypodal tether (T) as described herein. Thus, for example, the polypodal tether can be a tripodal tether, e.g., as illustrated in Table 1.

In one illustrative embodiment the redox-active molecule (P) can be represented by Formula XV:

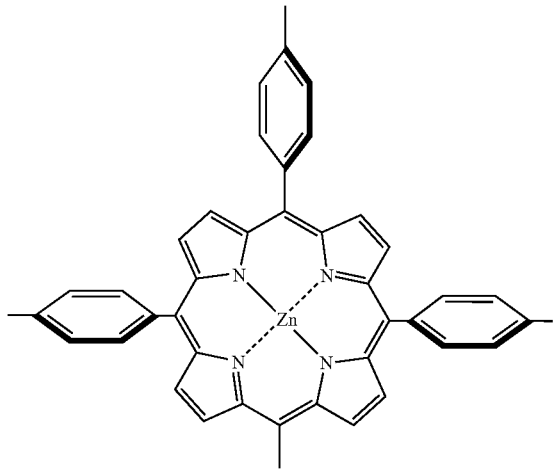

XV

In certain embodiments the redox-active molecules include, but are not limited to porphyrin arrays and porphyrin sandwich compounds, including, but not limited to double-decker and triple-decker porphyrin sandwich compounds. The design and synthesis of suitable porphyrin arrays and sandwich compounds is described in U.S. Pat. No. 6,212,093 B1, in U.S. Patent Publications 20030169618, 20030104229, 20030092896, and by Arnold et al. (1999) Chem. Lett. 483-484, which are incorporated herein by reference.

The ligands in a typical sandwich coordination compound are generally arranged in a stacked orientation (i.e., are generally cofacially oriented and axially aligned with one another, although they may or may not be rotated about that axis with respect to one another) (see, e.g., Ng and Jiang (1997) Chemical Society Reviews 26: 433-442) incorporated by reference. Sandwich coordination complexes include, but are not limited to "double-decker sandwich coordination compounds" and "triple-decker sandwich coordination compounds". The synthesis and use of sandwich coordination compounds is described in detail in U.S. Pat. Nos. 6,212,093; 6,451,942; 6,777,516; and polymerization of these molecules is described in U.S. Ser. No. 10/800,147, filed on Mar. 11, 2004, entitled Procedure for Preparing Redox-Active Polymers on Surfaces, and WO 2005/086826 which are herein incorporated by reference, particularly the individual substituent groups that find use in both sandwich complexes and the "single macrocycle" complexes.

In addition, polymers of these sandwich compounds are also of use; this includes "dyads" and "triads" as described in U.S. Pat. Nos. 6,212,093; 6,451,942; 6,777,516; and polymerization of these molecules is described in PCT Publication WO 2005/086826.

As indicated above, the redox-active molecules can comprise polymers of redox-active moieties. For example, porphyrin polymers (including polymers of porphyrin complexes), macrocycle complex polymers, ReAMs comprising two redox active subunits, etc. can be utilized. The polymers can be homopolymers or heteropolymers, and can include any number of different mixtures (admixtures) of monomeric ReAMs, wherein "monomer" can also include ReAMs comprising two or more subunits (e.g. a sandwich coordination compound, a porphyrin derivative substituted with one or more ferrocenes, etc.). ReAM polymers are described in PCT Publication WO 2005/086826, which is expressly incorporated by reference in its entirety.

Figure 15A:
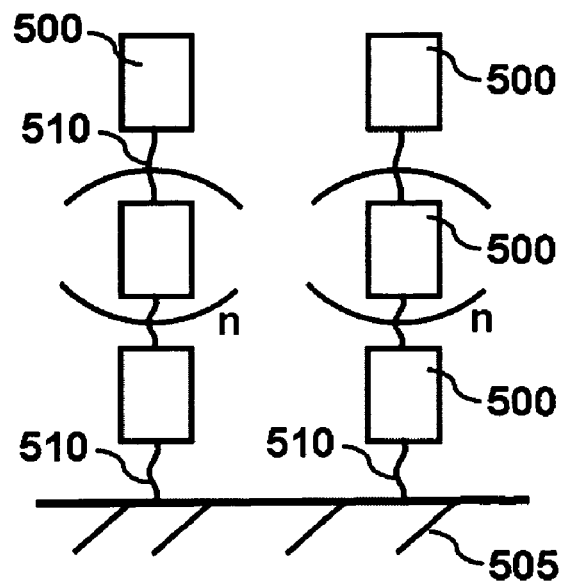
FIGS. 15A-15C schematically depict a variety of polymer configurations.
Figure 15B:
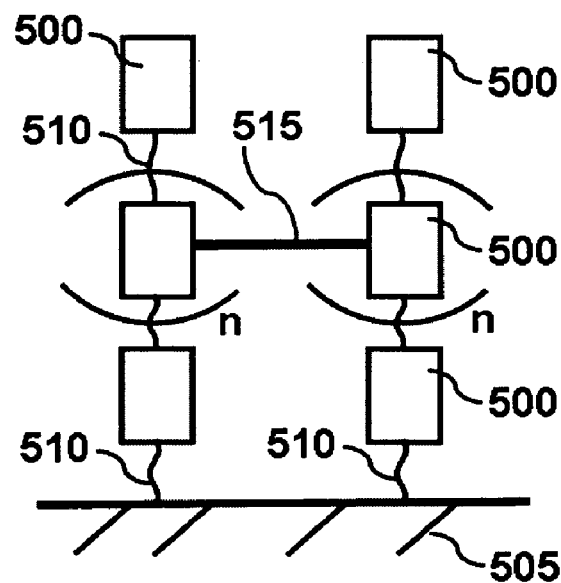
Figure 15C:
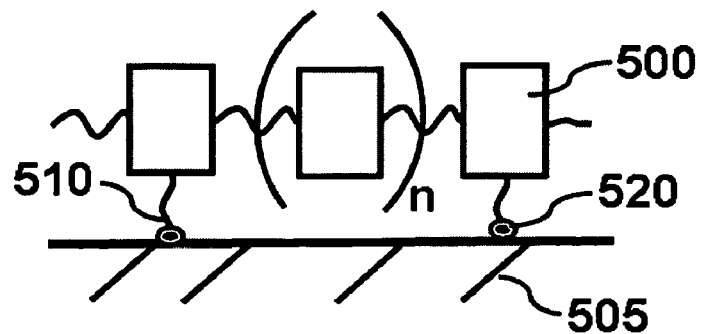

The configuration of the polymers on the substrate (e.g., electrode) can vary. In some embodiments, the polymers are linear in the Z dimension (the direction perpendicular to the substrate surface, as is depicted in FIG. 15A), and can be optionally crosslinked (FIG. 15B). Branched polymers in the Z dimension are also contemplated, and can be optionally crosslinked as well. Linear polymers in the X-Y-dimension (FIG. 15C), or branched and/or crosslinked polymers are also included. In addition, mixtures of polymers can be used in any of these configurations.

In general, the polymerization embodiments rely on the use of substituents that will result in both attachment to the electrode surface (e.g., via a multipodal tether) as well as polymerization to additional ReAMs. Two general approaches the synthesis of these ReAMs include "in situ" polymerization on the surface, and prepolymerization followed by addition to the surface using one or more attachment moieties (e.g. tethers as described herein).

Organometallic Ligands.

In certain embodiments the redox-active moieties (ReAMS) are or comprise an organometallic ligand. In addition to purely organic compounds for use as redox moieties, and various transition metal coordination complexes with δ-bonded organic ligand with donor atoms as heterocyclic or exocyclic substituents, there is available a wide variety of transition metal organometallic compounds with 7r-bonded organic ligands (see, e.g., Advanced Inorganic Chemistry, 5th Ed., Cotton & Wilkinson, John Wiley & Sons, 1988, chapter 26; Organometallics, A Concise Introduction, Elschenbroich et al., 2nd Ed., 1992, VCH; and Comprehensive Organometallic Chemistry II, A Review of the Literature 1982-1994, Abel et al. Ed., Vol. 7, chapters 7, 8, 10 & 11, Pergamon Press, hereby expressly incorporated by reference). Such organometallic ligands include cyclic aromatic compounds such as the cyclopentadienide ion [C5H5(−1)] and various ring substituted and ring fused derivatives, such as the indenylide (−1) ion, that yield a class of bis(cyclopentadieyl)metal compounds, (i.e. the metallocenes) (see, e.g., Robins et al. (1982) J. Am. Chem. Soc. 104: 1882-1893; Gassman et al. (1986) J. Am. Chem. Soc. 108: 4228-4229, and the like, which are incorporated herein by reference. Of these, ferrocene [(C5H5)2Fe] and its derivatives are prototypical examples which have been used in a wide variety of chemical and electrochemical reactions (see, e.g., Connelly et al. (1996) Chem. Rev. 96: 877-910; Geiger et al., Advances in Organometallic Chemistry 23: 1-93; Geiger et al., Advances in Organometallic Chemistry 24: 87)

Metallocene derivatives of a variety of the first, second and third row transition metals are useful as redox moieties (and redox-active subunits). Other suitable organometallic ligands include cyclic arenes such as benzene, to yield bis(arene) metal compounds and their ring substituted and ring fused derivatives, of which bis(benzene)chromium is a prototypical example. Still other acyclic π-bonded ligands such as the allyl(−1) ion, or butadiene yield potentially suitable organometallic compounds, and all such ligands, in conjunction with other π-bonded and δ-bonded ligands constitute a general class of organometallic compounds in which there is a metal to carbon bond. Various dimers and oligomers of such compounds with bridging organic ligands, and additional non-bridging ligands, as well as with and without metal-metal bonds are all useful.

When one or more of the proligands is an organometallic ligand, the ligand is generally attached via one of the carbon atoms of the organometallic ligand, although attachment may be via other atoms for heterocyclic ligands. Preferred organometallic ligands include metallocene ligands, including substituted derivatives and the metalloceneophanes (see, e.g., page 1174 of Cotton and Wilkenson, supra). For example, derivatives of metallocene ligands such as methylcyclopentadienyl, with multiple methyl groups being preferred, such as pentamethylcyclopentadienyl, can be used to increase the stability of the metallocene. In some embodiments, the metallocene is derivatized with one or more substituents as outlined herein, particularly to alter the redox potential of the subunit or moiety.

As described herein, any combination of ligands may be used. Certain preferred combinations include: a) all ligands are nitrogen donating ligands; b) all ligands are organometallic ligands.

In certain embodiments, the redox-active molecule is or comprises a metallocene as shown in Formula XVI:

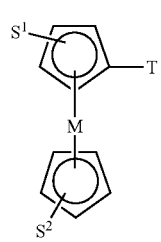

XVI where T is an optionally present linker or polypodal tether as described herein, M is a metal (e.g., Fe, Ru, Os, Co, Ni, Ti, Nb, Mn, Re, V, Cr, W, and the like), $S^1$ and $S^2$ are independently selected substituents including but not limited to aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl. In certain embodiments, a substituted aryl group is attached to the metallocene, and the substituents on the aryl group are selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl.

Certain suitable substituents include, but are not limited to, 4-chlorophenyl, 3-acetamidophenyl, 2,4-dichloro-4-trifluoromethyl. Preferred substituents provide a redox potential range of less than about 2 volts.

The oxidation state of molecules of Formula XVI is determined by the metal and the substituents. Thus, certain particular preferred embodiments are illustrated by the formulae of FIGS. 12A-12F.

The ferrocenes listed above in the formulae of these figures provide a convenient series of one-bit molecules having different and distinguishable oxidation states. Thus the molecules of these formulae have oxidation states of +0.55 V, +0.48V, +0.39 V, +0.17 V, −0.05 V, and −0.18 V, respectively, and provide a convenient series of molecules for incorporation into a storage medium of this invention.

The metallocene in Formula XVI can be attached directly or via a spacer (X) to a polypodal tether (T) as described herein. Thus, for example, the polypodal tether can be a tripodal tether, e.g., as illustrated in Table 1.

Figure 13A:
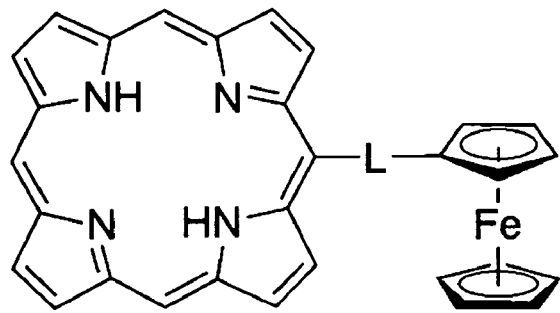
FIGS. 13A-13C depict various embodiments of redox-active molecules for use in the present invention.
Figure 13B:
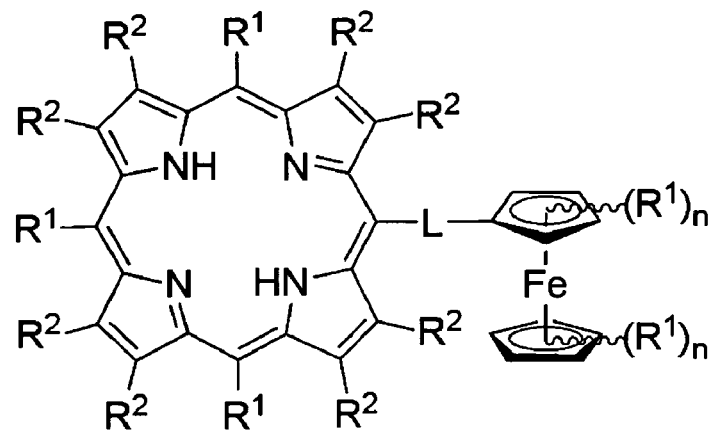
Figure 13C:
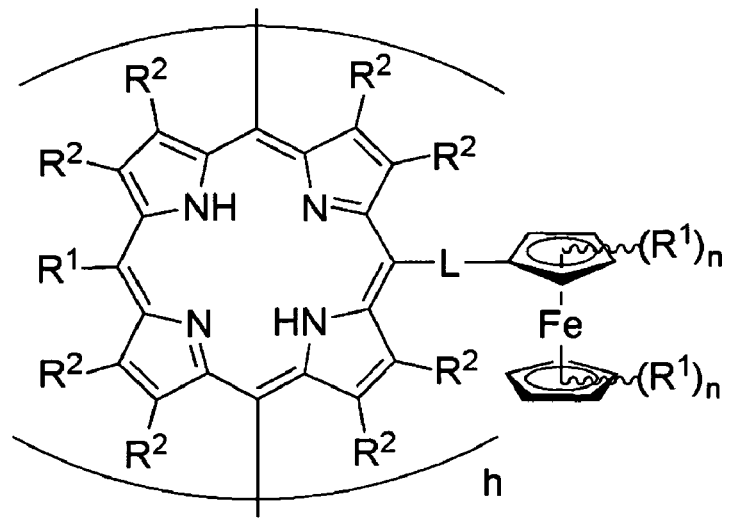
Figure 14A:
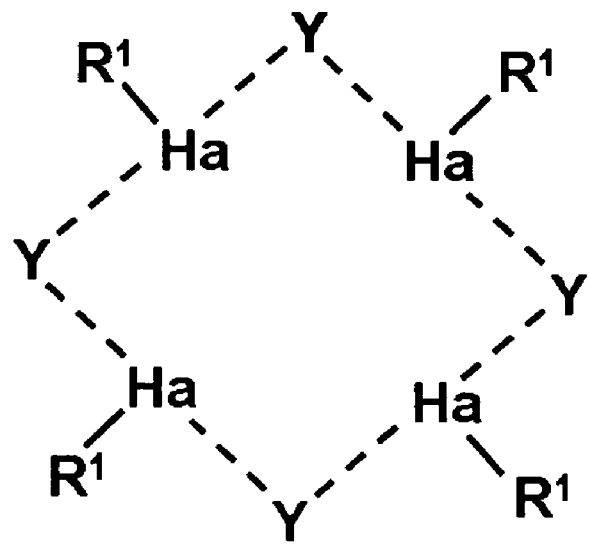
FIG. 14A-14I depict macrocyclic proligands based on cyclen derivatives. The metal ions are not shown, and it will be appreciated that there may be additional hydrogen atoms not depicted as a result. In various embodiments the derivatives can be 12, 13, 14, 15 or 16 membered rings, depending the number of skeletal atoms in the —Y—structure, and the additional skeletal atoms may be carbon or a heteroatom.
Figure 14B:
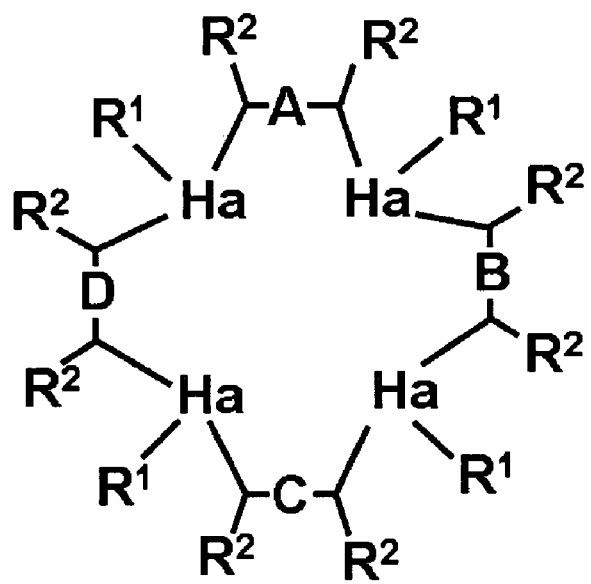
Figure 14C:
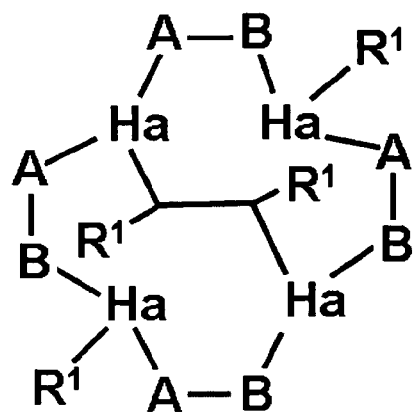
Figure 14D:
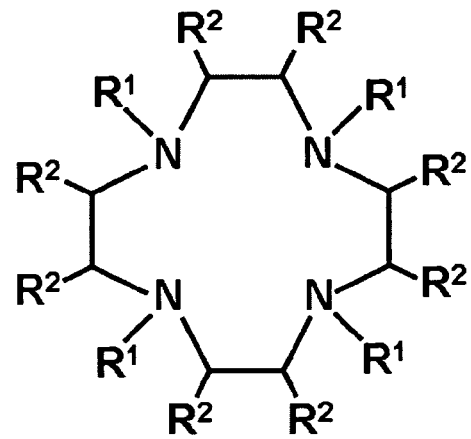
Figure 14E:
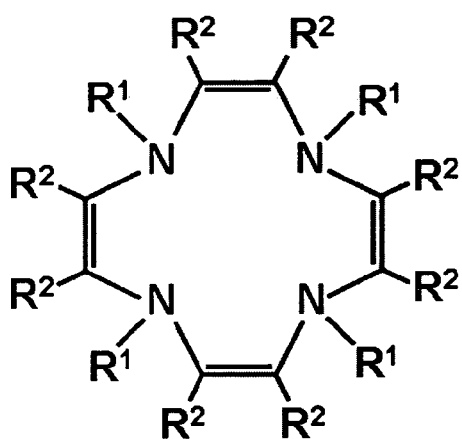
Figure 14F:
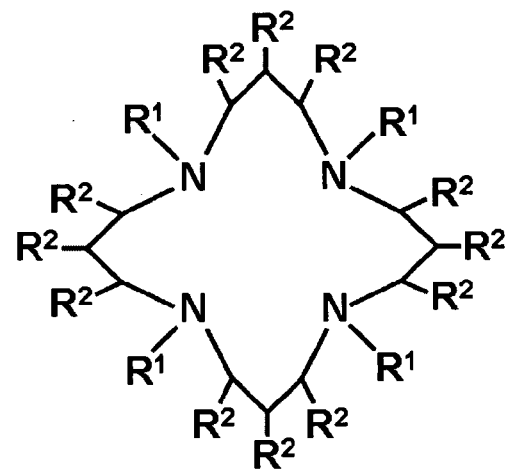
Figure 14G:
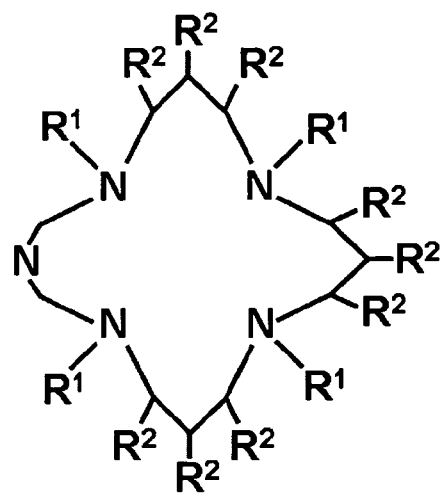
Figure 14H:
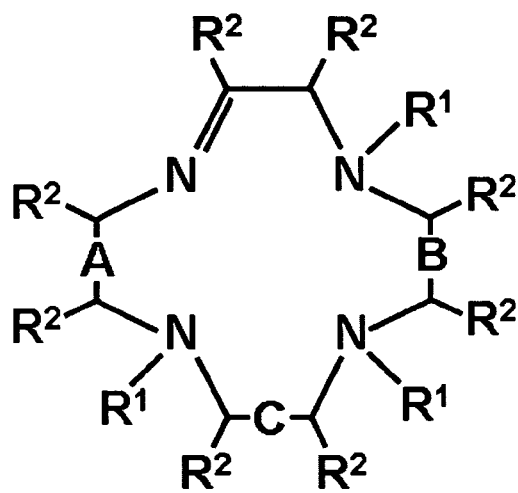
Figure 14I:
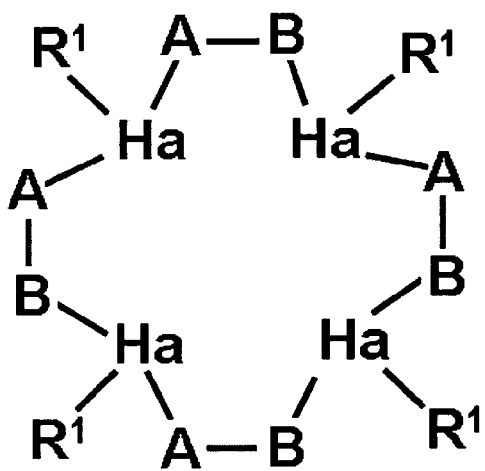

It is also noted, that in certain embodiments, a single redox active molecule can have two or more redox active subunits. For example, as shown in FIG. 13A, there are two redox active subunits, a porphyrin (shown in FIGS. 13A-13C in the absence of a metal) and a ferrocene (both of which can be optionally substituted with independently selected substituents at any position, as described below and depicted in FIG. 13B), usually, but optionally, attached via a linker, L. Similarly, sandwich coordination compounds are considered a single ReAM. This is to be distinguished from the case where these ReAMs are polymerized as monomers; for example, FIG. 13C depicts a polymerized version of FIG. 13B, wherein h is an integer of 2 or more. In addition, the metal ions/complexes of the invention may be associated with a counterion, not generally depicted herein.

Cyclen Derivatives.

There are also a number of suitable macrocycles based on cyclen derivatives. FIG. 14 depicts a number of macrocyclic proligands loosely based on cyclen/cyclam derivatives, which can include skeletal expansion by the inclusion of independently selected carbons or heteroatoms. In some embodiments, at least one R group is a redox active subunit, preferably electronically conjugated to the metal. In some embodiments, including when at least one R group is a redox active subunit, two or more neighboring R groups form cyclo or an aryl group.

Non-Macrocyclic Derivatives.

As a general rule, ReAMs comprising non-macrocyclic chelators are bound to metal ions to form non-macrocyclic chelate compounds, since the presence of the metal allows for multiple proligands to bind together to give multiple oxidation states.

In some embodiments, nitrogen donating proligands are used. Suitable nitrogen donating proligands are well known in the art and include, but are not limited to, $NH_2$; NHR; NRR'; pyridine; pyrazine; isonicotinamide; imidazole; bipyridine and substituted derivatives of bipyridine; terpyridine and substituted derivatives; phenanthrolines, particularly 1,10-phenanthroline (abbreviated phen) and substituted derivatives of phenanthrolines such as 4,7-dimethylphenanthroline and dipyridol[3,2-a:2',3'-c]phenazine (abbreviated dppz); dipyridophenazine; 1,4,5,8,9,12-hexaazatriphenylene (abbreviated hat); 9,10-phenanthrenequinone diimine (abbreviated phi); 1,4,5,8-tetraazaphenanthrene (abbreviated tap); 1,4,8,11-tetra-azacyclotetradecane (abbreviated cyclam) and isocyanide. Substituted derivatives, including fused derivatives, may also be used. It should be noted that macrocylic ligands that do not coordinatively saturate the metal ion, and which require the addition of another proligand, are considered non-macrocyclic for this purpose. As will be appreciated by those in the art, it is possible to covalent attach a number of "non-macrocyclic" ligands to form a coordinatively saturated compound, but that is lacking a cyclic skeleton.

Suitable sigma donating ligands using carbon, oxygen, sulfur and phosphorus are known in the art. For example, suitable sigma carbon donors are found in Cotton and Wilkinson, Advanced Organic Chemistry, 5th Edition, John Wiley & Sons, 1988, hereby incorporated by reference; see page 38, for example. Similarly, suitable oxygen ligands include crown ethers, water and others known in the art. Phosphines and substituted phosphines are also suitable; see page 38 of Cotton and Wilkinson.

The oxygen, sulfur, phosphorus and nitrogen-donating ligands can be attached in such a manner as to allow the heteroatoms to serve as coordination atoms.

In addition, some embodiments utilize polydentate ligands that are polynucleating ligands, e.g. they are capable of binding more than one metal ion. These may be macrocyclic or non-macrocyclic.

A number of suitable proligands and complexes, as well as suitable substituents, are outlined in U.S. Pat. Nos. 6,212,093; 6,728,129; 6,451,942; 6,777,516; 6,381,169; 6,208,553; 6,657,884; 6,272,038; 6,484,394; and U.S. Ser. Nos. 10/040,059; 10/682,868; 10/445,977; 10/834,630; 10/135,220; 10/723,315; 10/456,321; 10/376,865; all of which are expressly incorporated by reference, in particular for the structures and descriptions thereof depicted therein.

Defining Oxidation States.

The oxidation state of redox active molecules described herein (e.g., molecules of Formulae XIV and XVI) is determined by the metal and the substituents, and methods of determining/setting the oxidation states are described, for example, in U.S. Pat. Nos. 6,777,516, 6,728,129, 6,674,121, 6,657,884, 6,451,942, 6,381,169, 6,324,091, 6,272,038, 6,212,093, 6,208,553; PCT Publications WO 02/077633, WO 03/052835, WO 03/038886, and the like, which are incorporated herein by reference.

Control over the oxidation states, e.g., hole-storage and hole-hopping properties of the redox-active molecules used in the devices of this invention allows fine control over the architecture of the memory device.

Such control is exercised through synthetic design. The hole-storage properties depend on the oxidation potential of the redox-active units or subunits that are themselves functional storage media or that are used to assemble the storage media used in the devices of this invention. The hole-storage properties and redox potential can be tuned with precision by choice of base molecule(s), associated metals and peripheral substituents (see, e.g., Yang et al. (1999) *J. Porphyrins Phthalocyanines*, 3: 117-147, the disclosure of which is incorporated herein by reference).

For example, in the case of porphyrins, Mg porphyrins are more easily oxidized than Zn porphyrins, and electron withdrawing or electron releasing aryl groups can modulate the oxidation properties in predictable ways. Hole-hopping occurs among isoenergetic porphyrins in a nanostructure and is mediated via the covalent linker joining the porphyrins (see, e.g., Seth et al. (1994) *J. Am. Chem. Soc.*, 116: 10578-10592, Seth et al (1996) *J. Am. Chem. Soc.*, 118: 11194-11207, Strachan et al. (1997) *J. Am. Chem. Soc.*, 119: 11191-11201; Li et al. (1997) *J. Mater. Chem.*, 7: 1245-1262, Strachan et al. (1998) *Inorg. Chem.*, 37: 1191-1201, Yang et al. (1999) *J. Am. Chem. Soc.*, 121: 4008-4018), the disclosures of which are specifically incorporated herein by reference).

The design of compounds with predicted redox potentials is well known to those of ordinary skill in the art. In general, the oxidation potentials of redox-active units or subunits are well known to those of skill in the art and can be looked up (see, e.g., Handbook of Electrochemistry of the Elements). Moreover, in general, the effects of various substituents on the redox potentials of a molecule are generally additive. Thus, a theoretical oxidation potential can be readily predicted for any potential data storage molecule. The actual oxidation potential, particularly the oxidation potential of the information storage molecule(s) or the information storage medium can be measured according to standard methods. Typically the oxidation potential is predicted by comparison of the experimentally determined oxidation potential of a base molecule and that of a base molecule bearing one substituent in order to determine the shift in potential due to that particular substituent. The sum of such substituent-dependent potential shifts for the respective substituents then gives the predicted oxidation potential.

The suitability of particular redox-active molecules for use in the methods of this invention can readily be determined. The molecule(s) of interest are simply coupled to or adsorbed to a surface (e.g., a hydrogen passivated surface) according to the methods of this invention. Then sinusoidal voltammetry can be performed (e.g., as described herein or in U.S. Pat. Nos. 6,272,038; 6,212,093; and 6,208,553, PCT Publication WO 01/03126, or by (Roth et al. (2000) *Vac. Sci. Technol. B* 18:2359-2364; Roth et al. (2003) *J. Am. Chem. Soc.* 125:505-517) to evaluate: 1) whether or not the molecule(s) are affixed to the surface; and/or 2) the degree of coverage; and/or 3) whether or not the molecule(s) are degraded during the coupling procedure; and/or 4) the charge storage density; and/or 5) the available oxidation states; and/or 6) the stability of the molecule(s) to multiple read/write operations.

Various preferred redox-active molecules and the syntheses thereof include, but are not limited to those described in U.S. Pat. Nos. 6,208,553, 6,212,093, 6,272,038, 6,324,091, 6,381,169, and 6,451,942, and PCT Publication WO 01/03126, and the like which are incorporated herein by reference.

IV. Fabrication and Characterization of the Storage Device
  A) Fabrication.

Devices according to the present invention can be fabricated using standard methods well known to those of skill in the art. Typically fabrication methods utilize typical solid state fabrication technologies coupled with the synthesis methods described herein.

In certain preferred embodiments, electrode layer(s) are applied to a suitable substrate (e.g., silica, glass, plastic, ceramic, semiconductor, etc.) according to standard well known methods (see, e.g., Choudhury (1997) *The Handbook of Microlithography, Micromachining, and Microfabrication*, Soc. Photo-Optical Instru. Engineer, Bard & Faulkner (1997) *Fundamentals of Microfabrication*). In addition, examples of the use of micromachining techniques on silicon or borosilicate glass chips can be found in U.S. Pat. Nos. 5,194,133, 5,132,012, 4,908,112, and 4,891,120.

In one embodiment a metal layer is beam sputtered onto the substrate (e.g., a 10 nm thick chromium adhesion layer is sputtered down followed by a 200 nm thick layer of gold). Then maskless laser ablation lithography (see below), performed e.g., with a Nd:YAG laser, is used to create features with micron dimensions, or with an excimer laser to create features of nanometer dimensions) will create an array of parallel lines of conductor (e.g., gold), that can be used as working electrodes with dimensions ranging between a few microns to tens of nanometers.

Once the electrode array is formed, the entire array, or portions of the array, or individual electrodes are wetted (e.g., immersed or spotted) with one or more solutions of the appropriate derivatized storage media (e.g., porphyrin nanostructures), and the constituents of the memory media (e.g., monomeric porphyrin subunits) self-assemble on the arrays to form memory elements. It will be appreciated that different solutions can be applied to different regions of the electrode array to produce storage cells comprising different storage medium. Methods of spotting different reagents on surfaces (e.g., on glass surfaces) at densities up to tens of thousands of different species/spots per $cm^2$ are known (see, e.g., U.S. Pat. No. 5,807,522).

If desired, a suitable electrolyte layer (e.g., a thin layer of Nafion polymer) approximately 1 nm to 1000 nm, preferably about 100 nm to about 500 nm, more preferably about 10 nm to about 100 nm and most preferably about one hundred nanometers thick can be cast over portions or the entire surface of the chip. This polymer serves to hold the electrolyte for electrochemical reaction. Finally, the entire chip can be coated with a layer (e.g., 10 nm to about 1000 nm, more preferably 100 nm to about 300 nm and most preferably about 200 nm) of conducting material (e.g., silver) which acts as a reference electrode.

In certain approaches, the chip is then turned 90 degrees, and maskless laser ablation lithography can be performed again to create a second array of parallel lines that are perpendicular to the original set. This forms a three dimensional array of individual memory elements, where each element is formed by the intersection of these two perpendicular linear arrays.

Each individual element can be addressed by selecting the appropriate X and Y logic elements, corresponding to one working electrode and one reference electrode separated by the Nafion polymer/electrolyte layer. Since this structure is inherently three dimensional, it is possible, particularly using the polypodal tethers described herein to extend the array into the Z-direction, creating a 3-D array of memory elements as large as it is feasible to connect to.

These structures can be created on the micrometer or nanometer scale. It is possible to create these structures on a scale similar to silicon microstructures created with conventional nanolithographic techniques (i.e. 100-200 nm). This allows the interfacing of the memory elements with conventional silicon-based semiconductor electronics.

In the laser-ablation lithography, coherent light is sent through a beam splitter (50% transmittance) and reflected by a mirror to make two nearly parallel identical beams (Rosenwald et al. (1998) *Anal. Chem.*, 70: 1133-1140). These beams are sent through e.g., a 50 cm focal length lens for ease in focusing to a common point. The placement of the beams is fine-tuned to allow complete overlap of the mode structure of the laser spot. Higher order interference patterns are minimized through the use of high quality optics (1/10 wave surface flatness). This ensures that the variation between intensity maxima and minima in the first order will be several orders of magnitude larger than those formed with second and higher orders. This produces a well-defined pattern of lines across the electrode surface, where the spacing between points of positive interference (D) can be approximated by the Bragg Equation: $n\lambda=2D \sin(\theta/2)$, where $\lambda$=wavelength, $\theta$=angle between the beams, and n is order. For example, when a Nd:YAG is used at 1064 nm, the recombination of the two beams in this manner generates an interference pattern with ~2 micron spacing when the angle between the 2 beams is 15°. The interference pattern spacing can easily be changed by modifying the angle between the beams. Attenuation of the beam was accomplished by inserting one or more neutral density filters before the beam splitter. In this way, the exposure of the gold layer to the Nd-YAG interference pattern can be performed at different beam attenuations to produce power densities between 1 and 100 MW/cm$^2$.

In certain embodiments, the memory elements comprising the memory devices of this invention are fabricated using "moleholes". In certain embodiments, a "molehole" comprises two or more arrays of conductors or semiconductors (e.g., electrodes) separated from each other vertically (e.g., by a dielectric, insulator, etc.) so that the conductors overlap each other at least one point. Within one or more intersecting points of an upper and lower electrode (e.g., top and bottom interconnect) a well is fabricated. This well penetrates the electrodes, so that the electrodes form a portion of the side and/or bottom of the well.

Storage molecules of this invention are attached to one or more of the exposed conductor surfaces in the wells. Each well can then function as an electrochemical cell permitting electrochemical measurements of the bound molecules. The fabrication and use of such "moleholes" is described in detail in PCT Publication WO 03/085752.

B) Electrically Coupling Redox-Active Molecules to Electrode(s).

In the storage devices of this invention, the redox-active molecules are electrically coupled to one or more electrodes. The term "electrical coupling" is used to refer to coupling schemes that permit the redox-active molecules to gain or lose electrons to the electrode. The coupling can be a direct attachment of the redox-active molecules to the electrode, or an indirect attachment (e.g., via one or more polypodal tether(s)). The attachment can be a covalent linkage, an ionic linkage, a linkage driven by hydrogen bonding or can involve no actual chemical attachment, but simply a juxtaposition of the electrode to the storage medium. In some embodiments, the electrode can be some distance (e.g., about 5 Å to about 50 Å) from the storage medium and electrical coupling can be via electron tunneling, or other methods of electron transfer.

In some preferred embodiments, the polypodal tethers described herein are used to attach the redox-active molecules to the electrode(s). The tethers can be electrically conductive or they can be short enough that electrons can pass directly or indirectly between the electrode and the redox-active molecules.

Where the substrate (e.g., electrode) to which the storage molecule(s) are to be coupled comprises a group IV element (e.g., silicon, germanium, doped silicon, doped germanium, etc.) the molecules are readily coupled to the surface if provided with either a carbon, a thiol group, or an alcohol or with a tether comprising a thiol group, a carbon, or an alcohol. Methods of coupling a molecule comprising an alcohol or a thiol to a group IV element are described in copending application U.S. Ser. No, 10\040,059, filed on Oct. 26, 2001. Other methods of attaching redox-active moieties to substrates are described in U.S. Ser. No. 10/628,868, filed Jul. 28, 2003, in U.S. Ser. No. 10/742,596, filed Dec. 19, 2003, and in PCT/US2004/024105, filed Jul. 26, 2004, all of which are incorporated herein by reference for the methods and compounds disclosed therein.

Using the teachings provided herein, and in these references, other methods of coupling a storage molecule and/or molecules of a storage medium to one or more electrodes, or other substrates, will be routinely implemented by one of skill in the art.

C) Addressing the Memory Cells.

Addressing of the storage cell(s) in the devices of this invention is relatively straightforward. In one simple approach a discrete pair of electrodes (e.g., one working and one reference electrode) can be connected to every storage cell. Individual reference electrodes, however are not required and can be replaced with one or more common reference electrodes connected to all or to a subset of all of the storage elements in a particular device. Alternatively, the common reference electrodes can be replaced with one or more conductive "backplanes" each communicating to all, or to a subset, of the storage cells in a particular device.

Where the storage cells contain identical storage media, in certain embodiments, each storage cell is addressed with a separate working electrode so that the storage (oxidation) states of the storage cells can be distinguished from each other. Where the storage cells contain different storage media such that the oxidation states of one storage cell are different and distinguishable from the oxidation states of another storage cell, the storage cells can be addressed by a common working electrode thereby reducing the number of electrodes in a device.

In certain embodiments, the storage devices of this invention contain at least 2048, 4096, 8192, 16384, 32768, 65,536, 131,072, 262,144, 5,24,288, $10^6$, $10^7$, $10^8$, or $10^9$, or more storage locations per layer (2048, 4096, 8192, 16384, 32768, 65,536, 131,072, 262,144, 5,24,288, $10^6$, $10^7$, $10^8$, or $10^9$ or more locations in the mirror image architecture) with each location capable of storing one or more bits (e.g., holding a two bit word). In certain embodiments, a 1024-bit or a 512-bit chip can contain 8 wiring interconnects on each of the three electrode grids in the 3-dimensional architecture.

D) Characterization of the Memory Device.

The performance (e.g., operating characteristics) of the memory devices of this invention is characterized by any of a wide variety of methods, most preferably by electrochemical methods (amperometry and sinusoidal voltammetry, see, e.g., Howell et al. (1986) *Electroanal. Chem.*, 209: 77-90; Singhal and Kuhr (1997) *Anal. Chem.*, 69: 1662-1668), optical spectroscopy (Schick et al. (1989) *J. Am. Chem. Soc.* 111: 1344-1350), atomic force microscopy, electron microscopy, imaging spectroscopic methods, and the like. Surface-enhanced resonance and Raman spectroscopy can also be used to examine the storage medium on the electrodes.

Among other parameters, characterization of the memory devices (e.g., memory cells) involves determining the number of storage medium molecules (e.g., porphyrin arrays) required for defect-tolerant operation. Defect tolerance includes factors such as reliably depositing the required number of holes to write the desired digit and accurately detecting the numbers/transfer rates of the holes.

The long-term resistance of electron/holes to charge-recombination in the solid-phase medium of the device package is also determined. Using these parameters, the device architecture can be optimized for commercial fabrication.

IV. Writing to and Reading a Molecular Memory.

In certain embodiments of the data storage devices of this invention, information is written to a particular memory location via application of a potential of the requisite value and temporal duration at the appropriate working and/or reference electrode(s) to achieve the desired digital value. The information can be erased via application of a potential of the opposite sign.

There is a great advantage to the small size of each memory element, which is essentially a modified electrode surface. When each memory element is reduced to sub-micron dimensions, the area of the surface allows the presence of only a few hundred data storage (redox-active) molecules. Using Faraday's law, Q=nFN (where Q equals the total charge, n equals the number of electrons per molecule, F is 96,485 Coulombs/mole and N is the number of moles of electroactive species present), it can be determined that only a small charge (1.6× $10^{-16}$ C; if passed in 1 μs, would result in a current of roughly 160 pA) must pass in order to change the electrochemical charge corresponding to each bit.

Additionally, the intrinsic limitation to the speed of most electrochemical experiments lies in the time required to charge the electrode to the appropriate potential (the charging current, which has a time dependence of exp(–t/RC)). Since the capacitance of the electrode is directly proportional to its area, miniaturization of each element of the system to submicron dimensions will greatly increase its speed. For example, a square gold electrode with 0.1 μm dimensions would have a capacitance of approximately $2\times10^{-19}$ F, leading to an RC time constant of only 2 picoseconds. For this reason, electrode charging currents should be insignificant in determining the ultimate performance of these devices.

The voltage used to write the data can be derived from any of a wide variety of sources. In a simple embodiment, the voltage can simply be the output from a power supply. However, in certain preferred embodiments, the voltage will be the output from some element of an electronic circuit. The voltage can be a signal, the representation of a logic state, the output from a gate, from an optical transducer, from a central processing unit, and the like. In short, virtually any voltage source that can be electrically coupled to the devices of this invention can be used to write data to the storage media therein.

The storage device(s) of this invention can be read according to any of a wide variety of methods well known to those of ordinary skill in the art. Essentially any method of detecting the oxidation state of a compound can be utilized in the methods of this invention. However, where the readout is destructive of the state of the memory cell(s), the read will preferably be followed by a refresh to reset the oxidation state of the storage cell.

In certain embodiments redox-active molecules of a storage cell are set to neutral (e.g., 0 potential for the system, but which might not be at true zero voltage with respect to ground) using the working electrode. The oxidation state of the memory cell is then set by changing the potential at the reference electrode (e.g., by setting the reference electrode negative to the desired voltage). The oxidation state of the storage cell is then measured (e.g., using sinusoidal voltammetry) via the working electrode. In this format, the oxidation state can be assayed by measuring current. By measuring current at the working electrode and setting the state with the reference electrode, the measurement is not made at the place the potential is applied. This makes it is simpler to discriminate the oxidation state. If the potential were applied to the electrode through which the current was measured unnecessary noise could be introduced into the system.

In certain embodiments, reading of information from a particular memory location is achieved extremely rapidly by sweeping a potential over the full range used to establish the dynamic range of the storage element. The fidelity of the measurement is dependent on how well the oxidation state of the individual storage element can be determined. Traditionally, electrochemical methods could only improve the signal to noise ratio by discriminating the faradaic signal from the background components in the time domain through application of pulse waveforms (i.e., differential pulse polarography, square wave voltammetry). These methods discriminate the faradaic current from the charging current in the time domain, since charging currents decay much more rapidly than the faradaic current (exp(–t/RC) vs $t^{-1/2}$, respectively). However, the analytical faradaic current is not totally discriminated from the charging current, and most of the signal is discarded because sampling is done late in the pulse cycle.

Sinusoidal voltammetry (SV) has been shown to have significant advantages over traditional waveforms in an electrochemical experiment (Singhal et al. (1997) *Anal. Chem.*, 69: 1662-1668. For example, the background current resulting from cyclic voltammetry (consisting primarily of charging current) resembles a square wave, which contains significant intensity at both fundamental and odd harmonic frequencies. In contrast, the charging current resulting from sine wave excitation has only one frequency component centered at the fundamental, while the faradaic current is distributed over many frequencies. This characteristic of cyclic (e.g., sine wave) excitation simplifies the electroanalytical measurement, since the signal from each oxidation state can be fine-tuned by "locking-in" on one of the higher frequency harmonics. Ultimately, the speed at which this can be performed is only limited by the kinetics of the redox reaction, which may ultimately lead to megahertz frequency operation.

Since most electrochemical methods rely on differences between the $E_{1/2}$'s ($E_{1/2}$ is the potential at which half of the subject molecules are oxidized or reduced to a particular oxidation state) to differentiate compounds present in a sample and thereby to generate the selectivity for the measurement, this has severely limited the utility of electrochemical methods for the analysis of many complex matrices. In contrast, sinusoidal voltammetry can exploit the vast diversity in electron transfer rates observable at solid electrodes $k^0$, the rate of electron transfer, can vary over ten orders of magnitude at the same electrode surface) to obtain additional selectivity in the electrochemical measurement.

The composition of the frequency spectrum is extremely dependent on the rate of electron transfer. By adjusting the frequency of the sinusoidal (or other time-varying) excitation waveform, it becomes possible to use this kinetic information as well as the phase information to discriminate between two molecules which have very similar electrochemical properties. For example, this technique has been used for the detection of the direct oxidation of double-stranded DNA at copper electrodes (Singhal and Kuhr (1997) *Anal. Chem.*, 69: 1662-1668). Where this is usually undetectable at conventional electrodes with standard voltammetric techniques, the use of sinusoidal voltammetry allowed the measurement of 1.0 nM double-stranded DNA. The concentration detection limit (S/N=3) for this size of dsDNA at the 6th harmonic is 3.2 pM. When coupled with a low-volume system, such as a monolayer of the adsorbed material, this allows detection of sub-zeptomole ($10^{-21}$ mole) quantities of the storage medium molecule(s) on the surface.

This procedure may ultimately degrade the memory in the absence of a refresh mechanism. The level of degradation will depend on the total number of molecules ultimately used to ensure acceptable fault tolerance. To avoid degradation problems, however, a refresh cycle (a write cycle resetting the memory to the read value) can be inserted immediately after each read cycle is complete.

In certain embodiments, an improved signal to noise ratio (S/N) in the electrochemical measurement (e.g., amperometry, voltammetry, etc.) can be achieved by temporally dissociating the faradaic current from the charging current associated with reading the charge of the redox-active molecules (e.g., a self-assembled monolayer (SAM)). This method, designated open circuit potential amperometry (OCPA), quantitatively reads the charge of the redox species bound to (electrically coupled to) an electrode surface, while discriminating against both charging current(s) and amperometric signal(s) that arise, e.g., from diffusion-based species in solution.

Voltammetric data can also be obtained using this methodology. In this method, designated open circuit potential voltammetry (OCPV), a series of OCPA steps is performed in which the potential is successively incremented (similar to pulse voltammetric methods). OCPA and OPCV methods are described in detail in U.S. Ser. No. 10/098,996, in U.S. Ser. No. 10/098,996, filed on Apr. 7, 2004, and in PCT Publication WO 02/077633, which are incorporated herein by reference.

As indicated above, the molecular memory devices can be read by any of a wide variety of electrochemical technologies including amperometric methods (e.g., chronoamperometry), coulometric methods (e.g., chronocoulometry), voltammetric methods (e.g., linear sweep voltammetry, cyclic voltammetry, pulse voltammetries, sinusoidal voltammetry, etc.), any of a variety of impedance and/or capacitance measurements, and the like. Such readouts can be performed in the time and/or frequency domain.

In one preferred embodiment, readout is accomplished using a fast potentiostat/voltammetry system. Such a system is capable of reading and writing the memory elements, on a microsecond time scale. Such a system can be modified from a prototypical system described in U.S. Pat. No. 5,650,061.

An ultrafast impedance analysis system capable of characterizing the redox-active molecules on a microsecond or faster time scale can be constructed using an Arbitrary Waveform Synthesizer (e.g., HP 8770A, AWS) and a 1-GHz Digitizing Oscilloscope (e.g., HP 54111D) controlled by a computer system (e.g., HP 9000 series 300 computer system, Hewlett-Packard, Palo Alto, Calif.). The impedance data sets can be collected with the digital scope with 8192 time domain points at 25 MHz. Thus, a full 8192 point data set can be acquired in a total of 328 μs. Both the excitation and the response waveforms are measured; the excitation waveform is measured prior to the start of the experiment so that the response acquisitions can be done during the course of the experiment without interruption. One preferred excitation signal consists of a waveform with an amplitude of 60 $mV_{(p-p)}$ which covers a frequency band from approximately 30 KHz to over 1 MHz. If five complete replicates of each excitation or response waveform are contained within the 8192 data points set captured by the capture device (e.g., oscilloscope), because no further ensemble averaging is needed, each full impedance spectra can be acquired in 328 μs. Therefore, the whole frequency band under study can be excited and monitored in a single acquisition. The FET of the time domain data provides frequency-amplitude and frequency-phase characterization of the data equivalent to the data given by a lock-in based system.

V. Use of the Storage Device in Computer Systems and Other Devices.

Figure 27A:
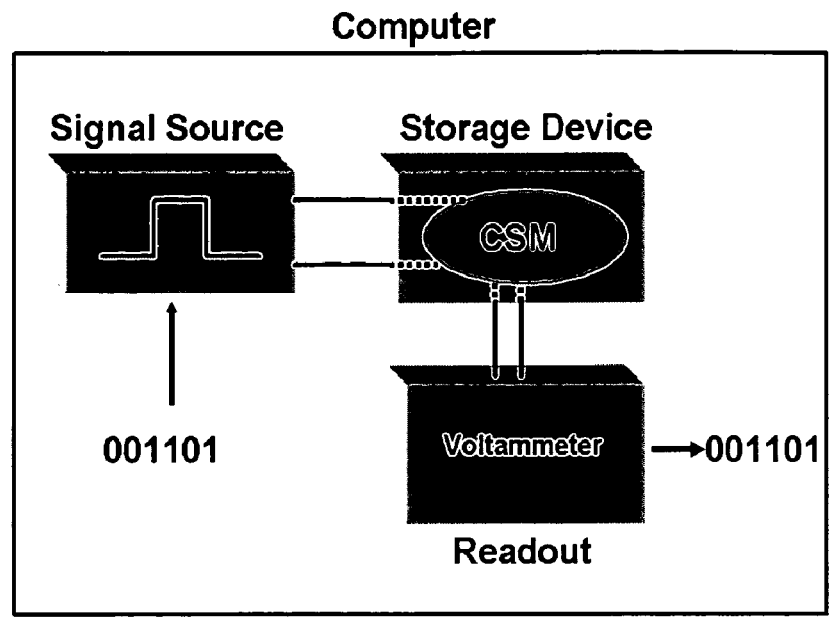
FIGS. 27A and 27B illustrate various computer architectures incorporating certain memory devices according to this invention.

The use of the storage devices fabricated according to the methods of this invention in computer systems is contemplated. One such computer system is illustrated in FIG. 27A. The computer comprises a signal source (e.g., I/O device or CPU), a storage device of this invention and appropriate circuitry (e.g., voltammetry circuitry) to read the state(s) of the storage device. In operation, voltages representing the bits to be stored are applied to the working electrodes of the storage device thereby setting the memory. When retrieval is necessary (e.g., for output, or further processing) the state(s) of the storage device is read by the I/O circuitry and the information is passed off to other elements (e.g., CPU) in the computer.

Figure 27B:
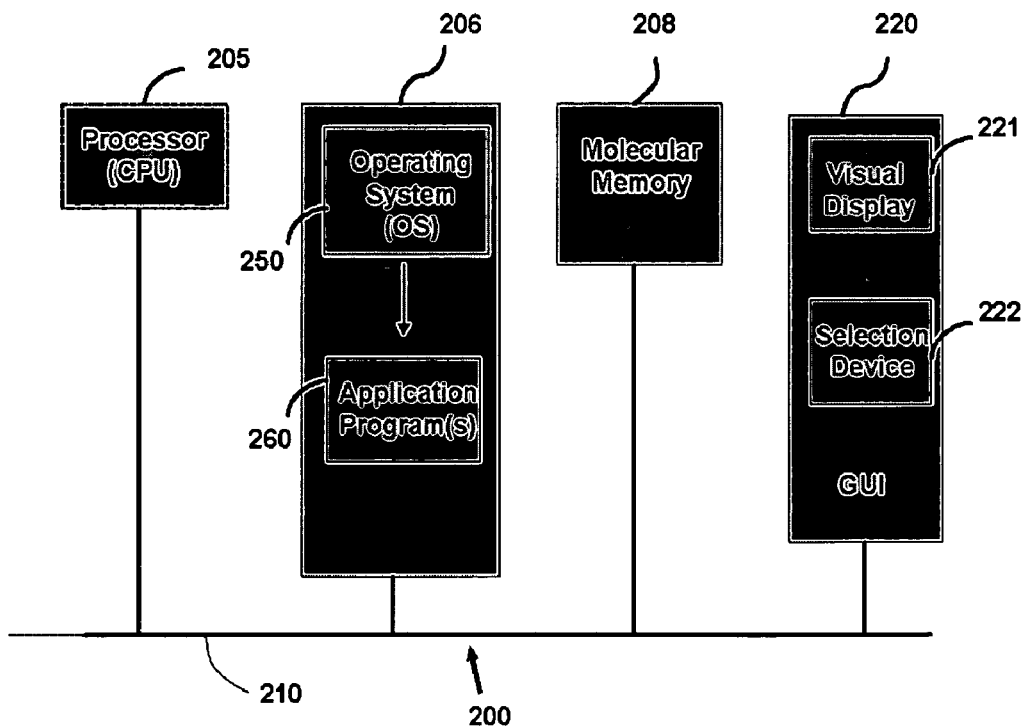

FIG. 27B illustrates the memory devices of this invention integrated into a standard computer architecture or computer system 200. The hardware of system 200 includes a processor (CPU) 205, a memory 206 (which can comprise molecular memory devices), a persistent storage 208 which does comprise molecular memory devices of this invention, and hardware for an optional graphical user interface (GUI) 220, coupled by a local bus or interface 210. The persistent memory 208 can include the elements shown in FIG. 27A. System 200 can further include additional hardware components (not shown).

System 200 can be, for example, a personal computer or workstation, a video game controller, a cell phone, a PDA, a digital video recorder, a digital music or video player, and the like. Processor 205 can be, for example, a microprocessor, such as the 80386, 80486, or Pentium™ microprocessor, made by Intel Corp. (Santa Clara, Calif.), a cell phone microprocessor, a video game microprocessor, and the like. Memory 206 can include, for example, random-access memory (RAM), read-only memory (ROM), virtual memory, molecular memory or any other working storage medium or media accessible by processor 205. Persistent storage 208 can include a hard disk, a floppy disk, an optical or magnetooptical disk, a molecular memory or any other persistent storage medium. GUI 220 facilitates communications between a user and system 200. Its hardware includes a visual display 221 and a selector device (mouse, keyboard, etc.) 222. Through visual display 221, system 200 can deliver graphical and textual output to the user. From selector device 222, system 200 can receive inputs indicating the user's selection of particular windows, menus, and menu items. Visual display 221 can include, for example, a cathode-ray tube (CRT) or flat-panel display screen, or a head-mounted display such as a virtual reality display. Selector device 222 can be, for example, a two-dimensional pointing device such as a mouse, a trackball, a track pad, a stylus, a joystick, or the like. Alternatively or additionally, selector device 222 can include a keyboard, such as an alphanumeric keyboard with function and cursor-control keys.

The software of system 200 can include an operating system 250 and an application program 260. The software of system 200 can further include additional application programs (not shown). Operating system 150 can be, for example, the Microsoft® Windows® operating system for IBM PC and compatible computers having or emulating Intel 80386, 80486, or Pentium™ processors, linux, various mobile PC and cell phone operating systems, and the like. The operating system can be specialized for operation utilizing molecular memory elements. Application program 160 is any application compatible with the operating system and system 200 architecture. Persons of skill in the art will appreciate that a wide range of hardware and software configurations can support the system and method of the present invention in various specific embodiments.

The memory devices of this invention can also be used in a wide variety of other devices—essentially any device in which "conventional" memory chips (e.g., DRAM, SRAM, Flash memory, etc.) are used. Such devices include, but are not limited to cell phones, computers, video game controllers, digital video recorders, digital music players, digital video players, dedicated storage devices, appliances, and the like.

EXAMPLES

The following examples are offered to illustrate, but not to limit the claimed invention.

Example 1

A Compact All-Carbon Tripodal Tether Affords High Coverage of Porphyrins on Silicon Surfaces Redox-active molecules designed to give high charge density on electroactive surfaces are useful for applications in molecular information storage. To achieve a small molecular footprint, and thereby high surface charge density, a compound consisting of a triallyl tripod attached via a p-phenylene unit to a porphyrin (1) has been synthesized. The zinc chelate of 1 (Zn-1) was attached to Si(100). Electrochemical measurements indicate that the molecular footprint (75 Å) in the monolayer is only ~50% larger than the minimum achievable, indicating high surface coverage. IR spectroscopy indicates the bands due to the $\nu(C=C)$ (1638 cm$^{-1}$) and $\gamma(CH)$ (915 cm$^{-1}$) vibrations present in the solid sample (KBr pellet) are absent from the spectra of the monolayers of Zn-1, consistent with saturation of the double bond in each of the three legs of the tripod upon the hydrosilylation process accompanying attachment. Comparison of the relative intensities of the in-plane (998 cm$^{-1}$) versus out-of-plane (797 cm$^{-1}$) porphyrin modes indicates the average tilt angle ($\alpha$) of the porphyrin ring with respect to the surface normal is ~46°, a value also observed for analogous porphyrins tethered to Si(100) via monopodal carbon linkers. Accordingly, the higher packing densities afforded by the compact tripodal linker are not due to a more upright orientation on the surface. The charge-retention half-lives ($t_{1/2}$) for the first oxidation state of the Zn-1 monolayers increase from 10-50 s at low surface coverage ($10^{-11}$ mol·cm$^{-2}$) to near 200 s at saturation coverage. Taken together, the high surface charge density (despite the lack of upright orientation) of the triallyl-tripodal porphyrin makes this construct a viable candidate for molecular information storage applications.

Introduction

Figure 3:
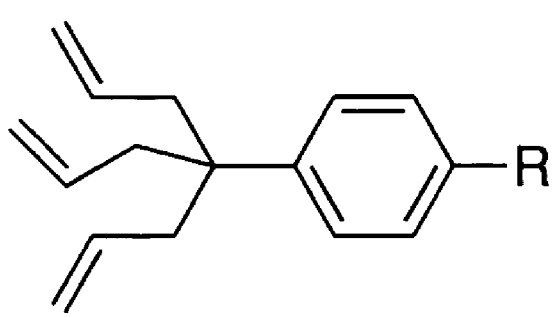
FIG. 3 illustrates various triallyl-arene compounds suitable for use in the compositions and methods of this invention.

We sought an improved tripod design for linking redox-active molecules to electroactive surfaces. Our initial focus was new tripods for attachment to silicon substrates. In this regard, our previous studies of porphyrin monolayers on silicon revealed that carbon anchors are generally more robust than anchors such as oxygen or sulfur (Liu et al. (2004) *J. Org. Chem.*, 69: 5568-5577). Accordingly, we chose to design the tripod(s) with alkenyl functionalization to provide attachment via a carbosilane linkage. We also sought a design wherein the tripod is relatively compact. We anticipated that this might facilitate attachment to the surface via all three legs of the tripod and potentially to higher packing densities in the monolayers. We ultimately chose a triallyl-substituted arene motif for the tripod. Illustrative triallyl-arene compounds (3a-g) known to date are shown in FIG. 3 (Lin et al. (1997) *Synth. Commun.*, 27: 1975-1980; Sartor et al. (2000) *New J. Chem.*, 24: 351-370; Martinez et al. (2002) *Org Lett.*, 4: 651-653). The goal was to extend this chemistry to incorporate the triallyl tripod with a porphyrin unit.

In this example, we first describe the synthesis of the tripodal porphyrins. We then examine the structural and electron-transfer characteristics of one member of this set, the zinc chelate (Zn-1), attached to Si(100). The Zn-1 monolayers on Si(100) were examined using fast-scan cyclic voltammetry to quantitate the packing densities of the monolayers, swept waveform AC voltammetry (SWAV) to elucidate the kinetics of electron transfer,[3] open circuit potential amperometry (OCPA) to determine the time of charge retention after removal of the applied potential (Roth et al. (2002) *Langmuir*, 18: 4030-4040), and Fourier transform infrared (FTIR) spectroscopy to measure the relative orientations of the porphyrin rings with respect to the surface plane (Yasseri et al. (2004) *J. Am. Chem. Soc.*, 126: 15603-15612; Wei et al. (2005) *J. Phys. Chem. B*, 109: 6323-6330).

Results and Discussion

Synthesis.

Figure 4:
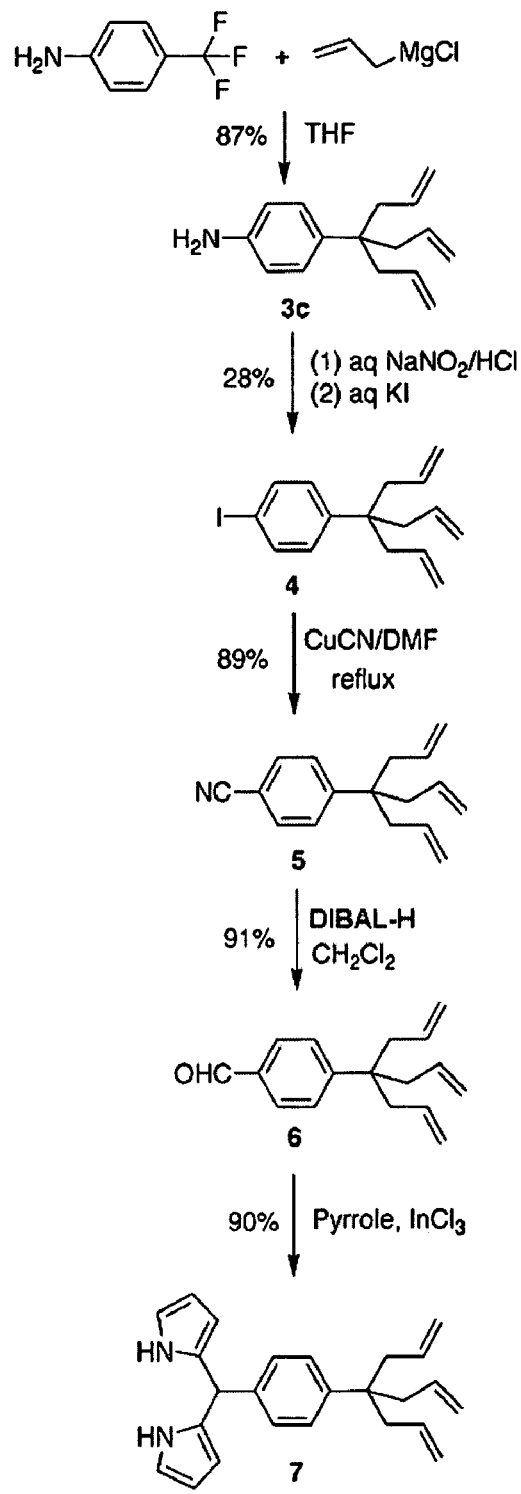
FIG. 4 illustrates synthesis Scheme 1.

Our design of the porphyrin bearing a triallyl tripod incorporates a p-phenylene group between the porphyrin and the central carbon of the tripod. A p-tolyl group is present at each of the three non-linking meso-positions of the porphyrin. The synthesis of the resulting A$_3$B-porphyrin can be achieved via the condensation of a dipyrromethane-dicarbinol with the dipyrromethane bearing the tripod (Rao et al. (2000) *J. Org. Chem.*, 65: 7323-7344). The synthesis of the latter begins with commercially available 4-(trifluoromethyl)aniline, which upon reaction with allyl magnesium chloride provides 4-(triallylmethyl)aniline (3c) (Lin et al. (1997) *Synth. Commun.*, 27: 1975-1980) (FIG. 4, Scheme 1). The reaction requires 5 equiv of allyl magnesium chloride and involves repetition of fluoride elimination followed by addition of the Grignard reagent to the resulting quinone-imine. The previous synthesis at the 2-mmol scale in diethyl ether afforded 3c in 54% yield. We carried out the reaction at the 160-mmol scale in THF and obtained 3c in 87% yield.

The conversion of the triallyl-aniline 3c to the triallyl-iodobenzene 4 was achieved via the Sandmeyer reaction. Diazotization of amine 3c in the presence of hydrochloric acid with sodium nitrite at 0-5° C. followed by treatment with potassium iodide gave iodo compound 4 in 28% yield. The Rosenmund-von Braun reaction of 4 with CuCN in DMF afforded the triallyl-cyanobenzene 5 in 89% yield. Reduction of 5 with DIBAL-H gave the triallyl-benzaldehyde 6 in 91% yield. Treatment of 6 to the standard conditions for dipyrromethane formation (excess pyrrole and $InCl_3$ at room temperature) (Laha et al. (2003) *Org. Process Res. Dev.,* 7: 799-812) provided dipyrromethane 7 in 90% yield.

Figure 5:
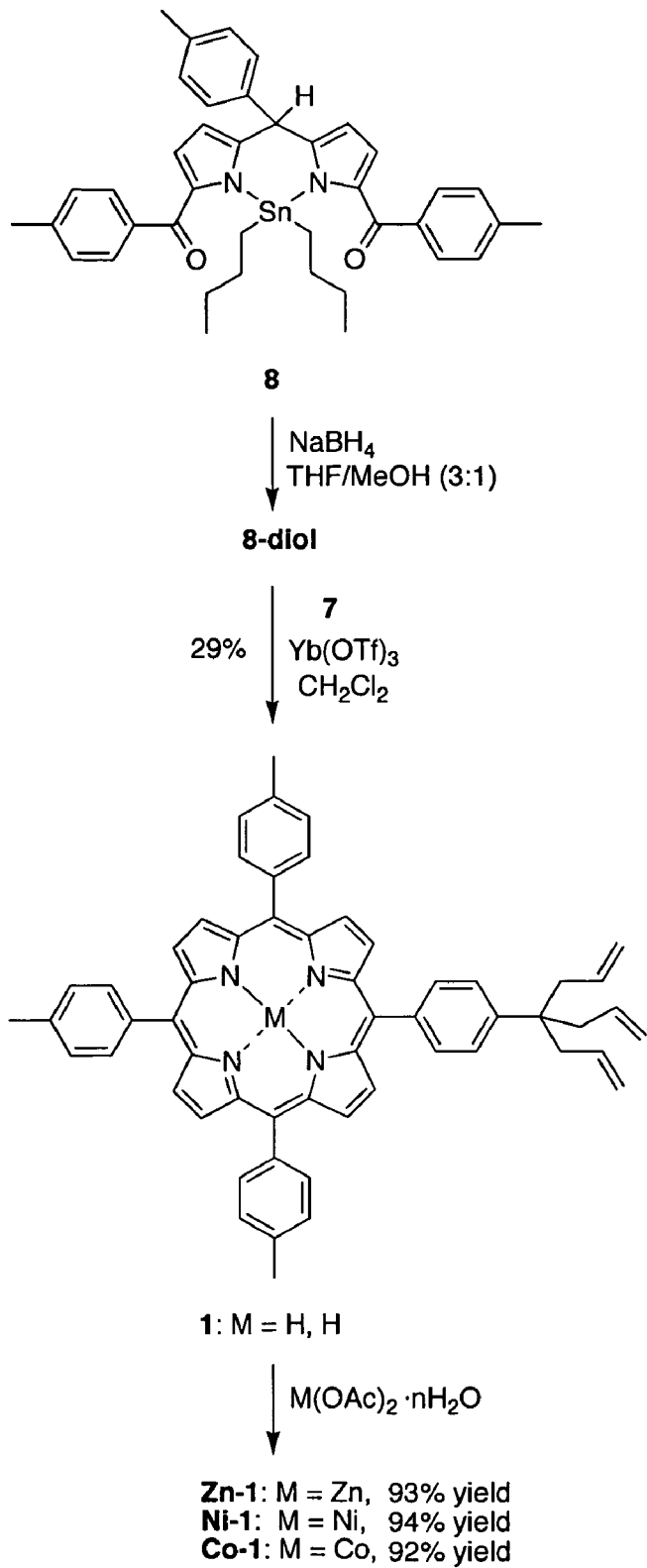
FIG. 5 illustrates synthesis Scheme 2.

The condensation of the triallyl-dipyrromethane 7 with dipyrromethane-dicarbinol 8-diol (prepared by reduction of 8 with $NaBH_4$) (Tamaru et al. (2004) *J. Org. Chem.,* 69: 765-777) at room temperature in the presence of a mild Lewis acid [$Yb(OTf)_3$] (Geier et al. (2001) *J. Porphyrins Phthalocyanines,* 5: 810-823) followed by oxidation with DDQ afforded free base porphyrin 1 in 29% yield. Metalation with $Zn(OAc)_2 \cdot 2H_2O$ at room temperature afforded the desired Zn-porphyrin Zn-1 in 93% yield. Similar metalation with $Ni(OAc)_2 \cdot 4H_2O$ or $Co(OAc)_2$ provided Ni-porphyrin Ni-1 or Co-porphyrin Co-1, respectively, in high yield (FIG. 5, Scheme 2).

Monolayer Characterization.

Monolayers of Zn-1 were prepared on Si(100) substrates and examined via electrochemical and FTIR techniques. The general electrochemical and vibrational characteristics of the Zn-1 monolayers are similar to those we have previously reported for other porphyrins tethered to Si(100) via monopodal carbon tethers (Wei et al. (2005) *J. Phys. Chem. B,* 109: 6323-6330). Consequently, we will not reiterate these general features herein, but rather only describe key features that distinguish the tripodal design from monopodal motifs.

Electrochemical Studies of Surface Coverage Electron-Transfer Rates, and Charge-Retention Times.

The goal of the electrochemical studies was to determine the saturation surface coverage and elucidate the electron-transfer and charge-retention characteristics of the Zn-1 monolayers. These properties of the monolayers are described below.

Figure 6:
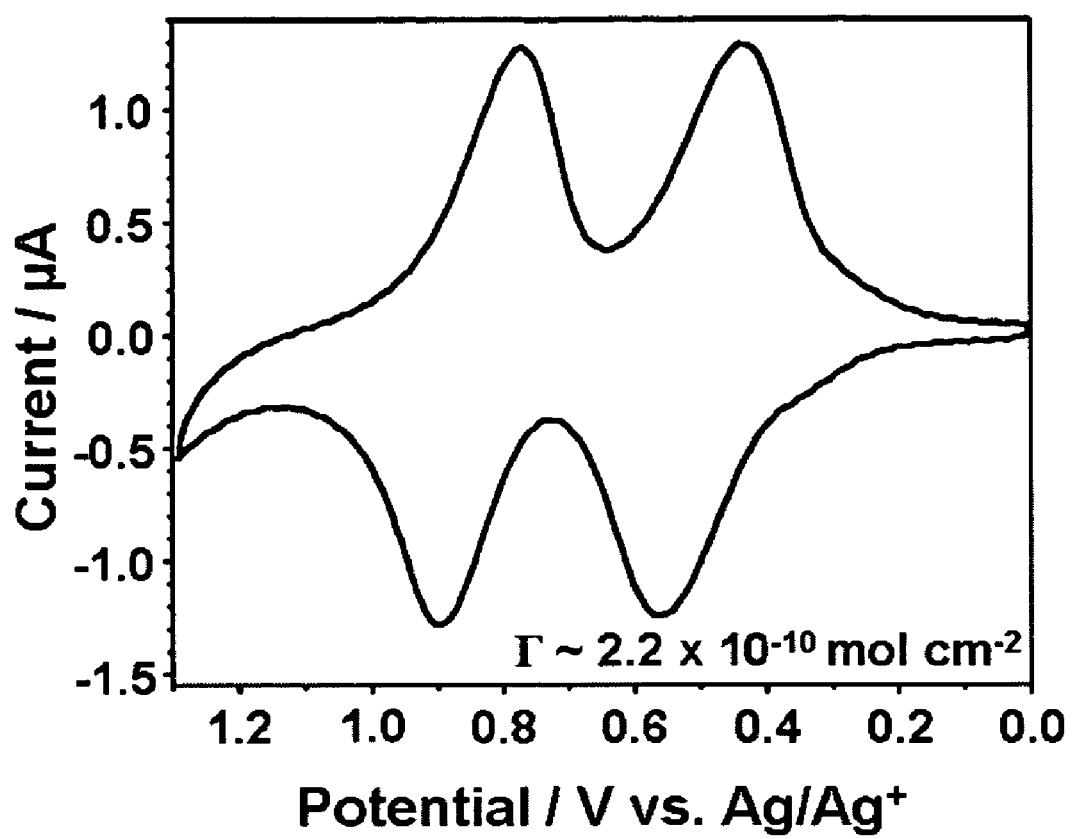
FIG. 6 illustrates a representative fast-scan (100 V s⁻¹) voltammogram of a Zn-1 monolayer on Si(100).

A representative fast scan (100 V s$^{-1}$) cyclic voltammogram for the saturation-coverage Zn-1 monolayer on a Si(100) microelectrode (100 μm×100 μm) is shown in FIG. 6. At oxidizing potentials, the monolayer exhibits two resolved voltammetric waves indicative of formation of the mono- and dication porphyrin π-radicals. The redox potentials are similar to those observed for this type of porphyrin tethered to Si(100) with other types of linkers (Roth et al. (2003) *J. Am. Chem. Soc.,* 125: 505-517; Yasseri et al. (2004) *J. Am. Chem. Soc.,* 126: 15603-15612; Wei et al. (2005) *J. Phys. Chem. B,* 109: 6323-6330). The surface coverage, $\Gamma$, obtained by integrating the voltammetric waves is $\sim 2.2 \times 10^{-10}$ mol·cm$^{-2}$, a value that is approximately three-fold higher than that obtained for porphyrins with monopodal carbon (or oxygen, sulfur, or selenium) tethers. The high saturation coverage observed for the tripodal porphyrin was highly reproducible from electrode to electrode. The surface coverage observed for Zn-1 corresponds to a molecular footprint of 75 Å$^2$, a value only 50% larger than that observed for porphyrins in Langmuir-Blodgett films (Schick et al. (1989) *J. Am. Chem. Soc.* 111: 1344-1350).

Figure 7:
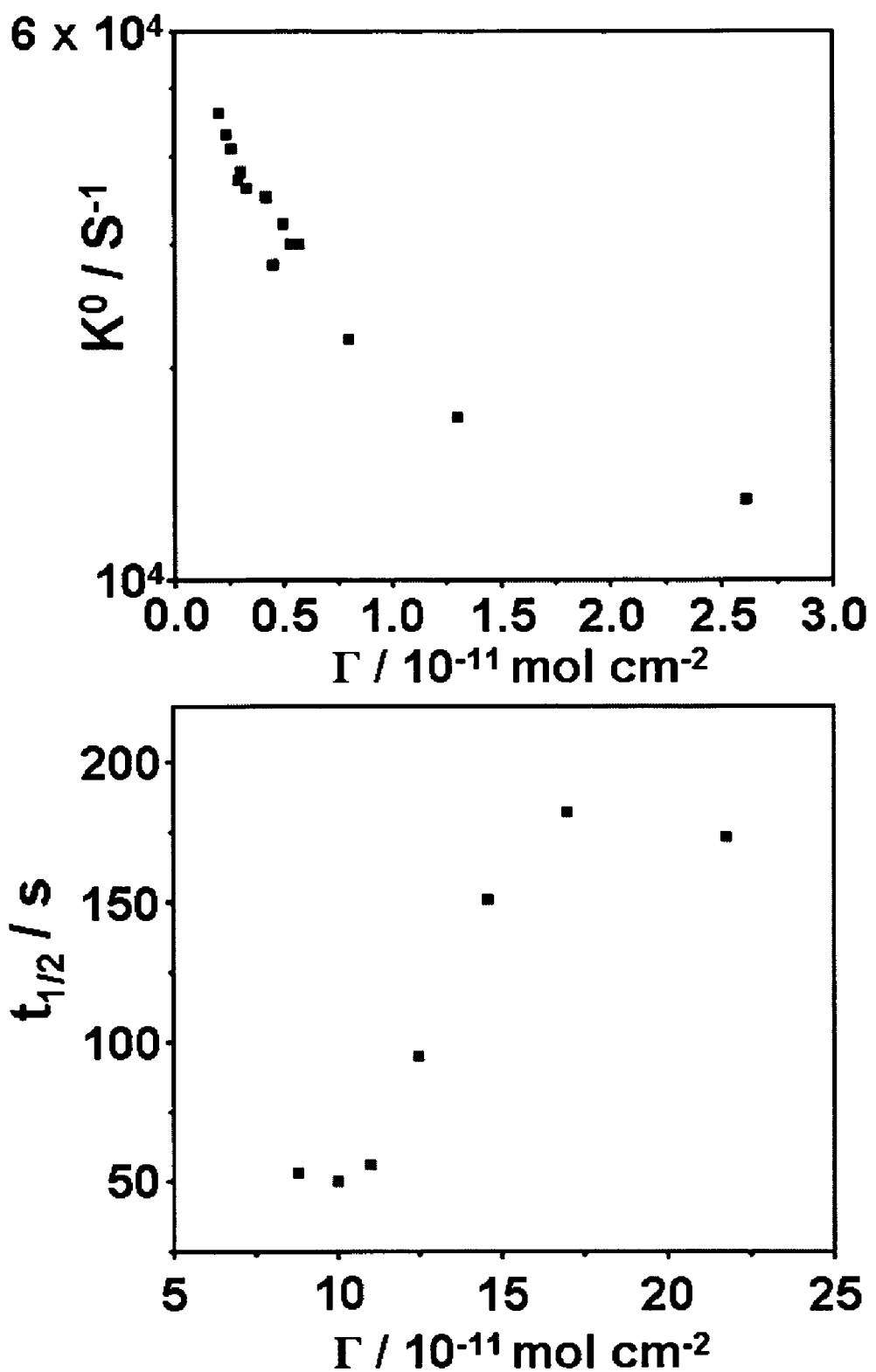
FIG. 7 illustrates standard electron-transfer rate constants, k⁰ (top panel), and charge-retention half-lives, $t_{1/2}$ (bottom panel), versus surface concentration, Γ, for the first oxidation state of Zn-1 monolayers on Si(100).

The standard electron-transfer rate constants, $k^0$, were measured for the first oxidation process ($E^{0/+1}$) of the Zn-1 monolayers at a variety of coverages from the low 10$^{-12}$ to mid 10$^{-11}$ mol·cm$^{-2}$ range. The interest in this surface-concentration dependence of the electron-transfer rates stems from our previous studies on porphyrin monolayers, both on Si(100) and Au(111), which show that the electron-transfer rates depend on surface coverage (Roth et al. (2002) *J. Phys. Chem. B,* 106: 8639-8648; Roth et al. (2003) *J. Am. Chem. Soc.,* 125: 505-517; Yasseri et al. (2004) *J. Am. Chem. Soc.,* 126: 15603-15612; Wei et al. (2005) *J. Phys. Chem. B,* 109: 6323-6330; Wei et al. (2004) *J. Org. Chem.,* 69: 1461-1469). As we have previously discussed, the electron-transfer rates cannot be measured at very high surface concentrations, i.e. those near saturation coverages, owing to experimental limitations. Nevertheless, the available concentration range is wide enough to compare the trends observed for the tripodal versus monopodal porphyrins. The electron-transfer rates of Zn-1 as a function of surface concentration are shown in FIG. 7 (top panel). Inspection of these data reveals that the electron-transfer rate decreases with increasing surface concentration, similar to the behavior observed for other types of porphyrin monolayers on both Au(111) and Si(100) (Id.). In addition, the electron-transfer rates observed for Zn-1 at any particular surface coverage are comparable to those observed for an analogous porphyrin with a monopodal carbon tether (Wei et al. (2005) *J. Phys. Chem. B,* 109: 6323-6330).

The charge-retention half-lives, $t_{1/2}$, were also measured at selected surface coverages for the first oxidation state of the Zn-1 monolayers, in parallel with the studies of the electron-transfer kinetics. Again, the interest in this surface-concentration dependence of charge-retention stems from our previous studies on porphyrin monolayers, both on Si(100) and Au(111), which show that this process also depends on surface coverage (Roth et al. (2002) *J. Phys. Chem. B,* 106: 8639-8648; Roth et al. (2003) *J. Am. Chem. Soc.,* 125: 505-517; Wei et al. (2005) *J. Phys. Chem. B,* 109: 6323-633; Wei et al. (2004) *J. Org. Chem.,* 69: 1461-1469). We were particularly interested in the charge-retention characteristics of Zn-1 at high surface coverage, beyond that achievable for porphyrins with monopodal linkers. The charge-retention half-lives of the Zn-1 monolayers as a function of surface concentration are shown in FIG. 7 (bottom panel). Inspection of these data reveals that the charge-retention times for all of the monolayers increase (charge-dissipation rates decrease) as the surface concentration increases, consistent with previous observations on other types of porphyrin monolayers on both Au(111) and Si(100) (Roth et al. (2002) *J. Phys. Chem. B,* 106: 8639-8648; Roth et al. (2003) *J. Am. Chem. Soc.,* 125: 505-517; Yasseri et al. (2004) *J. Am. Chem. Soc.,* 126: 15603-15612; Wei et al. (2004) *J. Org. Chem.,* 69: 1461-1469). The charge-retention times for Zn-1 at surface concentrations in the 10$^{-11}$ mol·cm$^{-2}$ regime are in the 10-50 s range, comparable to that observed for an analogous porphyrin with a monopodal tether (Wei et al. (2005) *J. Phys. Chem. B,* 109: 6323-6330). As the surface coverage is increased into the 10$^{-10}$ mol·cm$^{-2}$ range, the charge-retention times increase, peaking near 200 s at saturation coverage.

FTIR Studies of Adsorption Geometry.

The electrochemical studies show that the tripodal linker affords significantly higher surface coverage than either the tripods 2a and 2b or any of the types of monopodal linkers we have previously examined. The higher surface coverage afforded by the compact tripod versus the previous more bulky designs is easily rationalized, given the limitations of the latter linkers. On the other hand, the higher coverage of the compact tripod versus the monopodal linkers is less obvious. In this regard, our previous studies of porphyrins attached to Au(111) and Si(100) via monopodal tethers have shown that the molecules are significantly tilted with respect to the surface normal (Yasseri et al. (2004) *J. Am. Chem. Soc.,* 126: 11944-11953; Yasseri et al. (2004) *J. Am. Chem. Soc.,* 126:

15603-15612; Wei et al. (2005) *J. Phys. Chem. B,* 109: 6323-6330). Accordingly, one possible explanation for the higher packing densities exhibited by the compact tripod is that this design leads to a more upright orientation for the porphyrin. To explore this issue, we probed the adsorption geometry of the porphyrin using FTIR spectroscopy.

Figure 8:
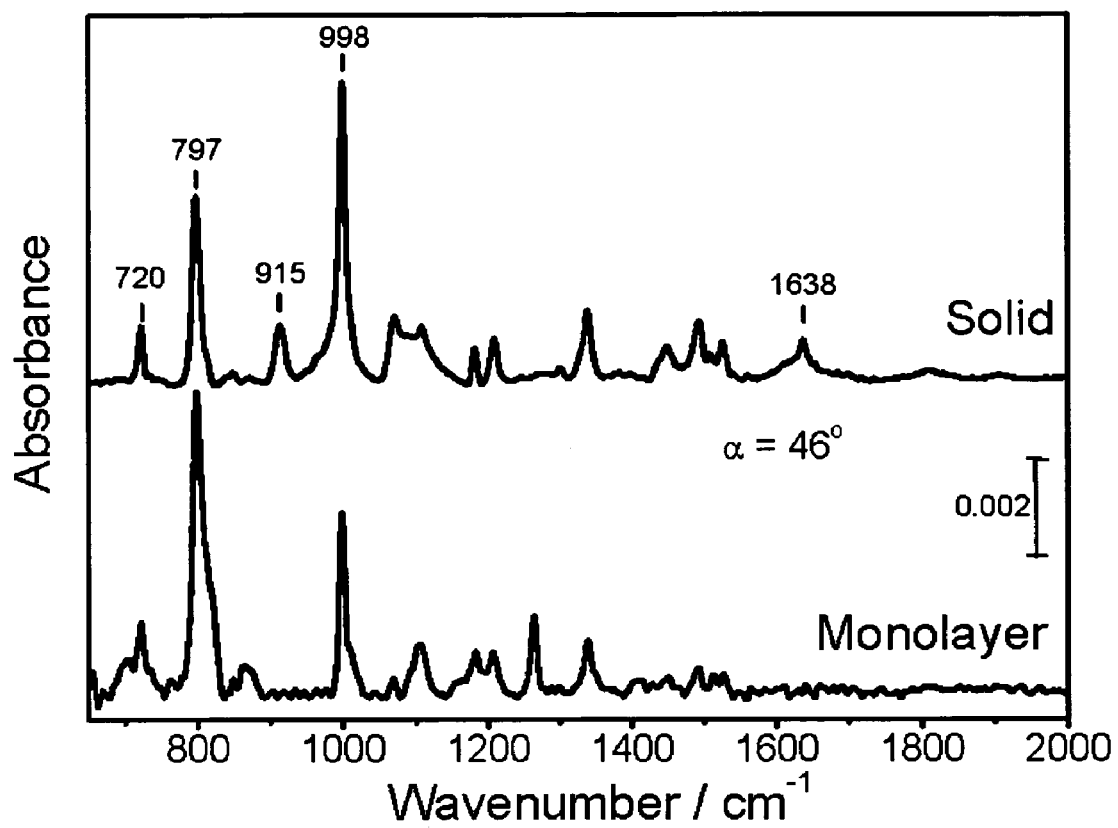
FIG. 8 illustrates FTIR spectra of a solid Zn-1 porphyrin in a KBr pellet and a corresponding Zn-1 monolayer on Si(100).
Figure 9:
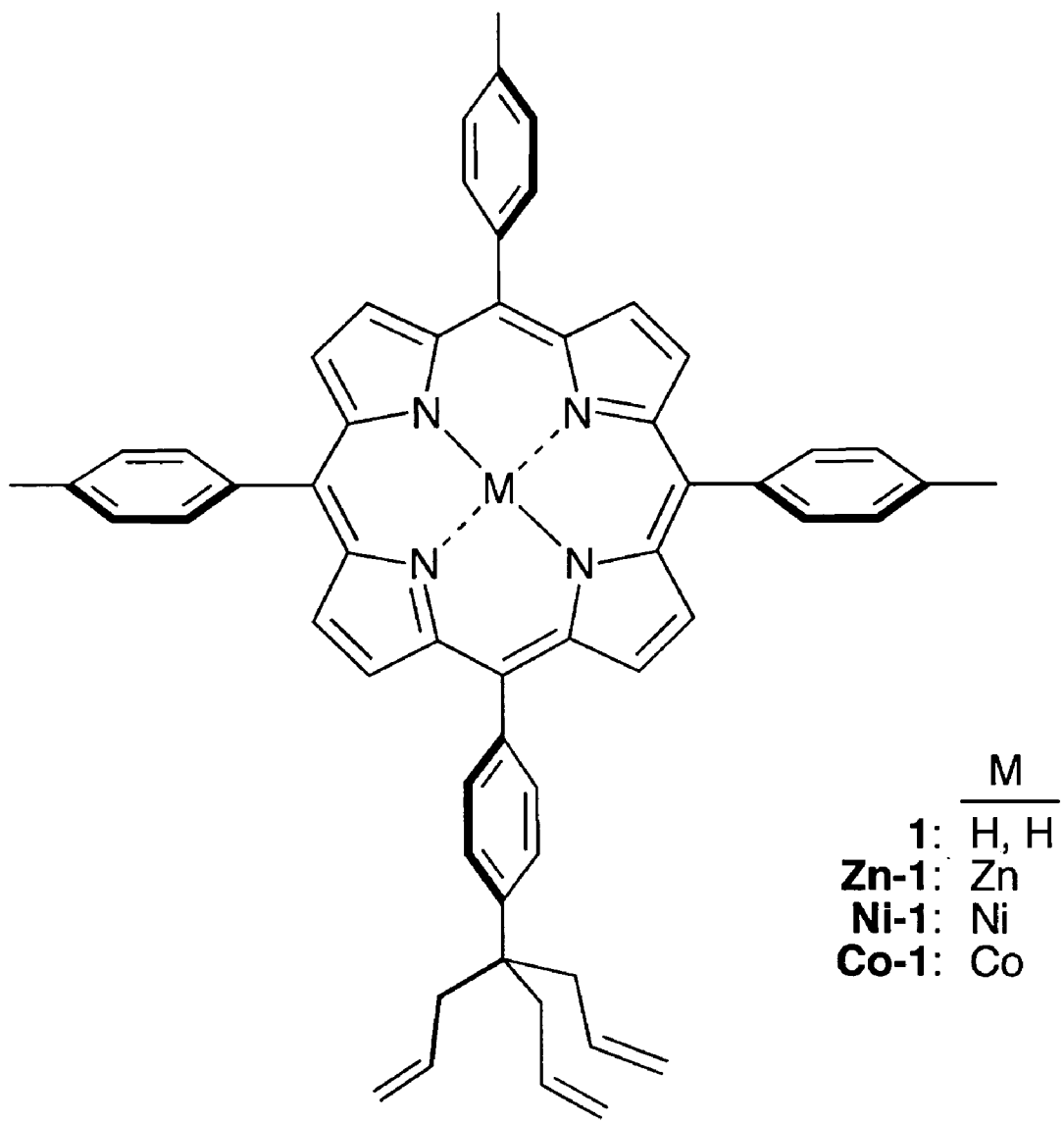
FIG. 9 illustrates a polypodal (tripodal) tether attached to a redox-active molecule (a porphyrin).

The mid-frequency (700-1900 cm$^{-1}$) IR spectrum of the saturation-coverage Zn-1 monolayer is shown in the bottom trace of FIG. 8; the spectrum of a solid sample of the parent porphyrin is shown in the top trace for comparison. The IR spectra of the tripodal porphyrin in both the monolayer and solid forms are similar to those we have previously reported for an analogous porphyrin with a monopodal linker (Wei et al. (2005) *J. Phys. Chem. B,* 109: 6323-6330). The key vibrational signatures relevant to our studies are the porphyrin pyrrole in-plane ring breathing mode near 998 cm$^{-1}$ (L$^1$ et al. (1990) *J. Phys. Chem.,* 94: 31-47), and the out-of-plane β-pyrrole hydrogen deformation at 797 cm$^{-1}$ (Li et al. (1989) *J. Am. Chem. Soc.,* 111: 7012-7023). For the solid sample, other important features are the C=C stretching vibration, ν(C=C), of the alkene group in the linker at 1638 cm$^{-1}$ and out-of-plane C—H deformation, γ(CH), of this group at 915 cm$^{-1}$ (Silverstein and Bassler (1967) *Spectrophotometric Identification of Organic Compounds,* Wiley: New York). [Note that only weak bands are seen in the high-frequency (2600-3400 cm$^{-1}$) spectral region (not shown), all attributable to C—H stretches.]

Comparison of the IR spectra of the solid and monolayers reveals that the bands due to the ν(C=C) (1638 cm$^{-1}$) and γ(CH) (915 cm$^{-1}$) vibrations are absent from the spectra of the monolayers. The absence of these bands is consistent with saturation of the double bond in each of the three legs of the tripod. These data are consistent with, although not definitive proof of, the view that each of the three legs of the compact tripod attaches to the Si(100) surface via a hydrosilylation reaction (as expected when an alkene reacts with hydrogen-passivated silicon (Buriak (1999) *Chem. Commun.* 1051-1060; Buriak (2002) *Chem. Rev.* 102: 1271-1308)).

The relative intensities of the in-plane (998 cm$^{-1}$) versus out-of-plane (797 cm$^{-1}$) porphyrin modes can be used to determine the average tilt angle (α) of the porphyrin ring with respect to the surface normal (Painter et al. (1982) *The Theory of Vibrational Spectroscopy and Its Application to Polymeric Materials,* Wiley: New York; Allara and Nuzzo (1985) *Langmuir,* 1: 52-66; Harrick and Mirabella (1985) *International Reflection Spectroscopy: Review and Supplement,* Harrick Scientific Corp., New York; Greenler (1966) *J. Chem. Phys.* 44: 310-315; Zaera, F. *Int. Rev. Phys. Chem.* 2002, 21, 433-471). The average angle determined for the porphyrins in the Zn-1 monolayers is ~46°, a value that is generally similar to those we have observed for analogous porphyrins tethered to Si(100) via monopodal carbon linkers (Wei et al. (2005) *J. Phys. Chem. B,* 109: 6323-6330). Accordingly, the higher packing densities afforded by the compact tripodal linker are not due to a more upright orientation on the surface. We speculate that the more symmetrical structure of the compact tripod may promote better long range ordering of the porphyrins on the surface than can be achieved via a monopodal linker. Finally, we note that attachment via three legs of the compact tripod and a tilted orientation for the porphyrin are not inconsistent. Molecular models of the tripod on the Si(100) surface show that tilted orientations are possible owing to the torsional flexibility of the alkane chains in the linker. We also note that tilting is not inconsistent with a small molecular footprint. In particular, the porphyrins in the very densely packed Langmuir-Blodgett films are significantly tilted with respect to the surface normal (Schick et al. (1989) *J. Am. Chem. Soc.* 111: 1344-1350).

Experimental Section
Synthesis
5-[4-(4-Allylhepta-1,6-dien-4-yl)phenyl]-10,15,20-tri-p-tolylporphyrin (1)

Following a general procedure (Tamaru et al. (2004) *J. Org. Chem.,* 69: 765-777; Geier et al. (2001) *J. Porphyrins Phthalocyanines,* 5: 810-823), a solution of 8 (Tamaru et al. (2004) *J. Org. Chem.,* 69: 765-777) (0.42 g, 0.60 mmol) in THF/MeOH (10:1, 24 mL) was treated with NaBH$_4$ (0.91 g, 24 mmol) at room temperature. After 2 h, the reaction mixture was quenched with saturated aqueous NH$_4$Cl and extracted with CH$_2$Cl$_2$. The organic phase was dried (Na$_2$SO$_4$) and concentrated to provide the corresponding dicarbinol 8-diol. The resulting dicarbinol was then immediately subjected to condensation with dipyrromethane 7 (214 mg, 0.600 mmol) in the presence of Yb(OTf)$_3$ (2.98 g, 4.81 mmol) in CH$_2$Cl$_2$ (240 mL). After 80 min, DDQ (409 mg, 1.80 mmol) was added and the mixture was stirred for 1 h. Then TEA (2.40 mL) was added and the mixture was stirred for about 30 min. The reaction mixture was passed through a pad of silica and eluted with CH$_2$Cl$_2$. The porphyrin band was collected and chromatographed [silica, hexanes/ethyl acetate (9:1→4:1)] to provide a pink solid (139 mg, 29%): $^1$H NMR δ −2.75 (s, 2H), 2.65-2.74 (m, 15H), 5.12-5.24 (m, 6H), 5.77-5.93 (m, 3H), 7.46-7.60 (m, 6H), 7.65 (d, J=8.0 Hz, 2H), 8.04-8.12 (m, 6H), 8.14 (d, J=8.0 Hz, 2H), 8.76-8.83 (m, 2H), 8.83-8.92 (m, 6H); MALDI-MS obsd 791.1; FABMS obsd 791.4146, calcd 791.4114 [(M+H)$^+$, M=C$_{57}$H$_{50}$N$_4$]; λ$_{abs}$ 421, 516, 551, 594, 649 nm.

Zinc(II)-5-[4-(4-Allylhepta-1,6-dien-4-yl)phenyl]-10,15,20-tri-p-tolylporphyrin (Zn-1)

A solution of 1 (132 mg, 167 μmol) in CHCl$_3$ (13 mL) was treated with a solution of Zn(OAc)$_2$.2H$_2$O (183 mg, 0.832 mmol) in MeOH (2.6 mL) at room temperature. The reaction was followed by TLC. The reaction was complete in 2 h. The reaction mixture was washed with saturated aqueous NH$_4$Cl and extracted with CH$_2$Cl$_2$. The combined organic layer was dried (Na$_2$SO$_4$), concentrated and chromatographed [silica, hexanes/ethyl acetate (9:1)] to afford a pink solid (132 mg, 93%): $^1$H NMR δ 2.66-2.78 (m, 15H), 5.12-5.28 (m, 6H), 5.80-5.96 (m, 3H), 7.50-7.60 (m, 6H), 7.67 (d, J=8.4 Hz, 2H), 8.04-8.14 (m, 6H), 8.16 (d, J=8.4 Hz, 2H), 8.88-8.94 (m, 2H), 8.94-9.02 (m, 6H); MALDI-MS obsd 852.4; FABMS obsd 852.3193, calcd 852.3170 (C$_{57}$H$_{48}$N$_4$Zn); λ$_{abs}$ 424, 551 nm.

Nickel(II)-5-[4-(4-Allylhepta-1,6-dien-4-yl)phenyl]-10,15,20-tri-p-tolylporphyrin (Ni-1)

A solution of 1 (12 mg, 15 μmol) in CHCl$_3$ (1.9 mL) was treated with a solution of Ni(OAc)$_2$.4H$_2$O (3.8 mg, 15 μmol) in MeOH (0.5 mL) at room temperature. The reaction was followed by TLC. The reaction did not proceed even after 9 h. Therefore an additional portion of Ni(OAc)$_2$.4H$_2$O (85 mg, 0.34 mmol) in MeOH (4 mL) and CHCl$_3$ (16 mL) was added and the reaction mixture was refluxed. After 11 h, some free base porphyrin remained. Another portion of Ni(OAc)$_2$.4H$_2$O (8.0 mg, 32 μmol) in MeOH (1 mL) was added and the reaction mixture was allowed to reflux for another 2 h. The reaction mixture was concentrated and then CH$_2$Cl$_2$ was added. The organic solution was washed with water, dried (Na$_2$SO$_4$), concentrated and chromatographed [silica, hexanes/CH$_2$Cl$_2$ (2:1)] to afford a pink solid (12 mg, 94%): $^1$H NMR δ 2.60-2.71 (m, 15H), 5.08-5.22 (m, 6H), 5.72-5.90 (m, 3H), 7.42-7.52 (m, 6H), 7.60 (d, J=8.4 Hz, 2H), 7.84-7.92 (m, 6H), 7.95 (d, J=8.4 Hz, 2H), 8.66-8.82 (m, 8H); MALDI-MS obsd 847.2; FABMS obsd 846.3284, calcd 846.3232 (C$_{57}$H$_{48}$N$_4$Ni); λ$_{abs}$ 417, 528 nm.

Cobalt(II)-5-[4-(4-Allylhepta-1,6-dien-4-yl)phenyl]-10,15,20-tri-p-tolylporphyrin (Co-1)

A solution of 1 (14 mg, 18 µmol) in CHCl$_3$ (8.5 mL) was treated with a solution of Co(OAc)$_2$ (31.1 mg, 176 µmol) in MeOH (1.7 mL) at room temperature. The reaction mixture was refluxed for 8 h with monitoring by TLC. The reaction mixture was concentrated and then CH$_2$Cl$_2$ was added. The organic solution was washed with water, dried (Na$_2$SO$_4$), concentrated and chromatographed [silica, hexanes/CH$_2$Cl$_2$ (2:1)] to afford a red solid (14 mg, 92%): $^1$H NMR δ 3.80-3.98 (m, 6H), 4.08-4.26 (br, 9H), 6.00-6.20 (m, 6H), 710-7.23 (br, 3H), 9.65-9.95 (m, 8H), 12.6-13.6 (br, 8H), 15.60-16.60 (br, 8H); MALDI-MS obsd 848.1; FABMS obsd 847.3267, calcd 847.3211 (C$_{57}$H$_{48}$CoN$_4$); λ$_{abs}$ 413, 530 nm.

4-(4-Allylhepta-1,6-dien-4-yl)aniline (3c)

Following a literature procedure (Lin et al. (1997) *Synth. Commun.*, 27: 1975-1980), a 2 M solution of allyl magnesium chloride in THF (0.400 L, 0.800 mol) was diluted with additional THF (1.00 L) and then treated dropwise with a solution of 4-(trifluoromethyl)aniline (19.9 mL, 0.160 mol) in THF (210 mL) at −50° C. under argon. After complete addition the sides of the reaction flask were rinsed with additional THF (150 mL). The resulting solution was heated at reflux. The reaction was monitored by TLC for the complete consumption of 4-(trifluoromethyl)aniline. After 3.5 h, the mixture was concentrated and then CH$_2$Cl$_2$ was added. The organic solution was washed with water, dried (Na$_2$SO$_4$), and filtered. The filtrate was concentrated and chromatographed [silica, CH$_2$Cl$_2$/hexanes (2:1)], affording a pale yellow solid (31.7 g, 87%): $^1$H NMR δ 2.36-2.43 (m, 6H), 3.48-3.66 (br, 2H), 4.94-5.06 (m, 6H), 5.50-5.64 (m, 3H), 6.62-6.70 (m, 2H), 7.06-7.12 (m, 2H); $^{13}$C NMR δ 42.1, 42.6, 115.0, 117.5, 127.6, 135.0, 135.8, 144.1; FABMS obsd 228.1757, calcd 228.1752 [(M+H)$^+$, M=C$_{16}$H$_{21}$N].

1-(4-Allylhepta-1,6-dien-4-yl)-4-iodobenzene (4)

A solution of conc. HCl/H$_2$O (1:1 v/v, 44 mL) was added to a solution of 3c (11.4 g, 50.2 mmol) in THF (80 mL). The mixture was stirred at room temperature for 75 min, then cooled to 0-5° C. A chilled solution of NaNO$_2$ (7.99 g, 116 mmol) in water (80 mL) was added while maintaining the temperature of the reaction mixture below 5° C. Additional H$_2$O (30 mL) was added. The reaction mixture was tested for the presence of nitrous acid with starch paper. A solution of KI (14.2 g, 85.5 mmol) in H$_2$O (16 mL) cooled to ~5° C. was added, again maintaining the mixture at <5° C. throughout the addition. Additional H$_2$O (24 mL) and THF (150 mL) were added. The reaction mixture was then gradually allowed to warm to room temperature. After ~6.5 h, the reaction mixture was neutralized with saturated aqueous Na$_2$CO$_3$ and then filtered. The filtrate was concentrated. The resulting residue was dissolved in CH$_2$Cl$_2$ and washed with water. The organic phase was dried (Na$_2$SO$_4$), concentrated and chromatographed (silica, hexanes) to afford a colorless liquid (4.73 g, 28%): $^1$H NMR (300 MHz) δ 2.38-2.50 (m, 6H), 4.94-5.12 (m, 6H), 5.44-5.64 (m, 3H), 7.00-7.12 (m, 2H), 7.58-7.70 (m, 2H); $^{13}$C NMR δ 41.8, 42.0, 43.5, 91.4, 117.8, 118.2, 129.1, 134.2, 137.3, 145.8.

4-(4-Allylhepta-1,6-dien-4-yl)benzonitrile (5)

Following a literature procedure (Hanack et al. (1993) *Synthesis*, 387-390), a mixture of 4 (5.07 g, 15.0 mmol), CuCN (2.03 g, 22.6 mmol) and DMF (50 mL) was heated over the course of 30 min until refluxing with continued reflux for 3 h. The reaction was monitored by TLC. The mixture was poured into a flask containing crushed ice and concentrated aqueous NH$_4$OH (200 mL). The resulting mixture was bubbled with oxygen for 14 h. The resulting dark blue mixture was then filtered. The layers of the filtrate were separated and the aqueous layer was extracted with CH$_2$Cl$_2$. The combined organic layer was dried (Na$_2$SO$_4$), concentrated and chromatographed [silica, hexanes/ethyl acetate (19:1)] to afford a colorless liquid (3.17 g, 89%): IR (CH$_2$Cl$_2$) 2230 cm$^{-1}$; $^1$H NMR (300 MHz) δ 2.40-2.54 (m, 6H), 4.94-5.12 (m, 6H), 5.40-5.62 (m, 3H), 7.36-7.48 (m, 2H), 7.56-7.68 (m, 2H); $^{13}$C NMR δ 41.6, 44.2, 109.8, 118.6, 119.1, 127.8, 132.0, 133.5, 151.7; FABMS obsd 238.1589, calcd 238.1596 [(M+H)$^+$, M=C$_{17}$H$_{19}$N].

4-(4-Allylhepta-1,6-dien-4-yl)benzaldehyde (6)

Following a literature procedure (Lindsey et al. (1994) *Tetrahedron*, 50: 8941-8968), a solution of 5 (2.21 g, 9.32 mmol) in CH$_2$Cl$_2$ (25 mL) was cooled to 0° C. and was treated dropwise with a 1 M solution of DIBAL-H in hexanes (11.2 mL, 11.2 mmol). The solution was allowed to slowly warm to room temperature. The reaction was monitored by TLC. After 3 h, the reaction mixture was poured into a beaker containing crushed ice and 6 N HCl. The mixture was stirred for about 1 h. The layers were separated and the aqueous phase was extracted with CH$_2$Cl$_2$. The combined organic layer was washed with aqueous NaHCO$_3$ followed by water. The organic layer was dried (Na$_2$SO$_4$), concentrated and chromatographed [silica, hexanes/ethyl acetate (19:1)] to afford a colorless liquid (2.04 g, 91%): IR (CH$_2$Cl$_2$) 3078, 1705 cm$^{-1}$; $^1$H NMR (300 MHz) δ 2.44-2.59 (m, 6H), 4.94-5.14 (m, 6H), 5.44-5.66 (m, 3H), 7.45-7.58 (m, 2H), 7.80-7.93 (m, 2H), 9.99 (s, 1H); $^{13}$C NMR δ 41.8, 44.3, 118.4, 127.6, 129.6, 133.8, 134.4, 153.4, 192.0; FABMS obsd 241.1597, calcd 241.1592 [(M+H)$^+$, M=C$_{17}$H$_{20}$O].

5-[4-(4-Allylhepta-1,6-dien-4-yl)phenyl]dipyrromethane (7)

Following a general procedure (Laha et al. (2003) *Org. Process Res. Dev.*, 7: 799-812), a degassed solution of 6 (1.54 g, 6.42 mmol) in pyrrole (45 mL, 649 mmol) at room temperature was treated with InCl$_3$ (136 mg, 0.615 mmol). The mixture was stirred for 4 h, during which the mixture turned greenish brown. The reaction was quenched by the addition of NaOH (769 mg, 19.2 mmol, 20-40 mesh beads). The reaction mixture was stirred for 1 h and then filtered through a plug of cotton. The filtered material was washed with CH$_2$Cl$_2$. The filtrate was concentrated and then diluted with CH$_2$Cl$_2$. The organic solution was washed with water, then dried (Na$_2$SO$_4$), concentrated, and chromatographed [silica, hexanes/ethyl acetate (4:1)] to provide a dark brown viscous liquid (2.05 g, 90%): $^1$H NMR δ 2.38-2.48 (m, 6H), 4.96-5.02 (m, 4H), 5.02-5.05 (m, 2H), 5.42 (s, 1H), 5.48-5.61 (m, 3H), 5.86-5.90 (m, 2H), 6.13-6.17 (m, 2H), 6.64-6.68 (m, 2H), 7.08-7.18 (m, 2H), 7.23-7.28 (m, 2H), 7.85 (br, 2H); $^{13}$C NMR δ 42.1, 43.3, 43.7, 107.4, 108.6, 117.4, 117.8, 127.2, 128.2, 132.9, 134.7, 139.5, 144.7. FABMS obsd 356.2256, calcd 356.2252 (C$_{25}$H$_{28}$N$_2$).

Example 2

Synthesis of Porphyrins Bearing Three Alcoholic Groups in a Tripodal Architecture for Studies in Molecular Information Storage The synthesis of a zinc porphyrin bearing three alcohol groups in a tripodal architecture is described. The porphyrin was prepared via a Suzuki coupling reaction of a meso-substituted boronic ester porphyrin and a masked tripodal alcohol aromatic bromo compound. The resulting masked alcohol porphyrin and its fully deprotected trialcohol porphyrin were found to attach to a variety of electroactive surfaces [Si(100), TiW, TiN, and WN].

Introduction

One approach to increase the charge storage density is to employ redox-active molecules (e.g., porphyrins) that possess a multipodal (e.g., a tripodal) surface attachment group. Such systems are anticipated to yield surface attached layers of redox-active molecules (ReAMs) having increased stability and/or higher charge storage density. Without being bound to a particular theory, it is believed that stability is improved because fewer native surface atoms remain unbound, thus limiting substrate and/or redox-active molecule degradation pathways.

In this example, the synthesis of several porphyrins bearing three alcohol groups in a tripodal architecture is described. This class of porphyrins were prepared as models to see if such a compact, trialcohol linker would generate porphyrin ReAM layers with high charge density and perhaps more importantly, greater stability towards volammetric cycling.

Results and Discussion

Synthetic Strategy.

Figure 10:
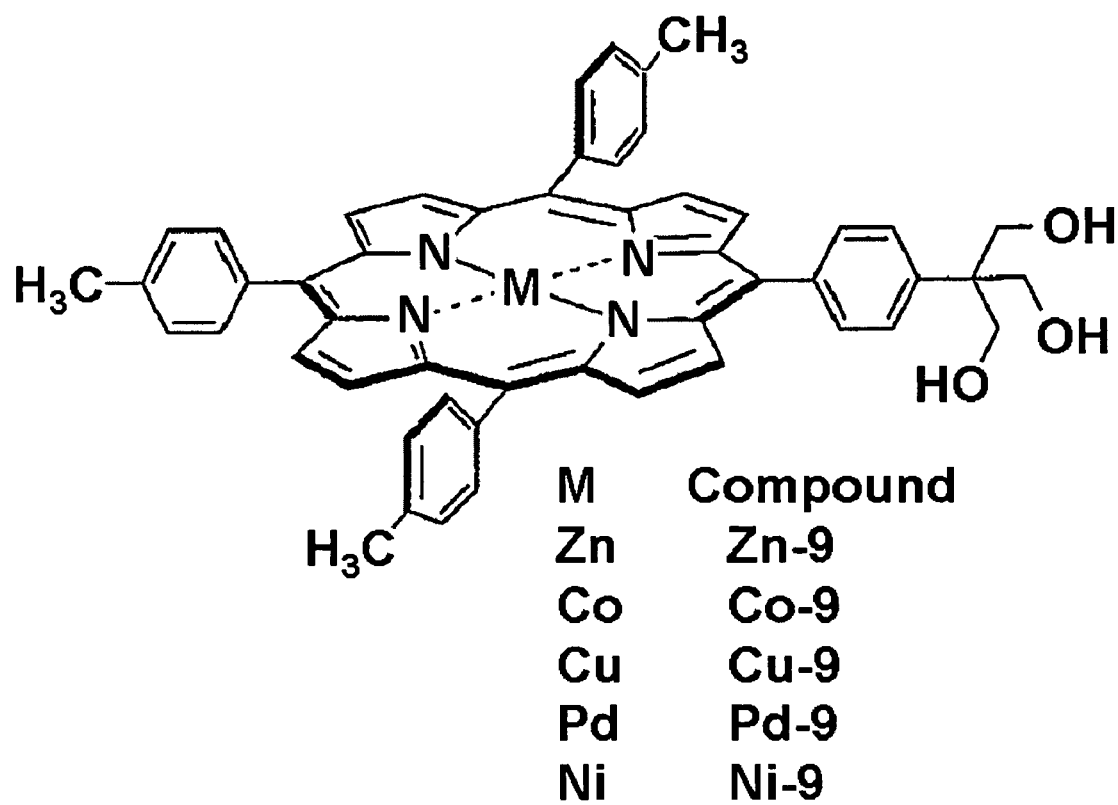
FIG. 10 shows some illustrative suitable porphyrins.

Our initial attempts to prepare the porphyrins shown in FIG. 10, relied on a Suzuki coupling reaction between a porphyrin bearing a meso-substituted boronic ester and a bromo-substituted compound bearing the requisite tripodal alcohol group. While preparing meso-substituted $A_3B$ porphyrins is well-known, compounds with tripodal alcoholic groups have been given less attention in the literature. However, several examples in the literature show the transformation of phenylacetaldehyde to $\alpha,\alpha,\alpha$-tris(hydroxymethyl) toluene using a Tollens' condensation. Following this general reaction, we sought to prepare 4-bromophenylacetaldehyde and subject this compound to the Tollens condensation. The resulting bromo-substituted building block can react in a Suzuki reaction with the porphyrin, affording the requisite synthetic targets needed to prepare the porphyrins shown in FIG. 10.

Synthesis of Zn-1.

Figure 16:
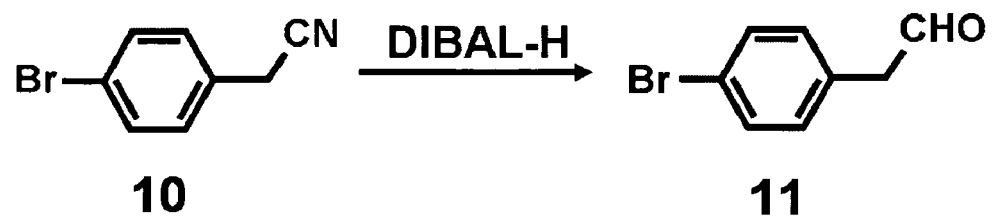
FIG. 16 illustrates the synthesis of a bromophenylacetaldehyde.

Our initial attempt to prepare 4-bromophenylacetaldehyde is shown in the equation in FIG. 16. Commercially available 4-bromophenylacetonitrile (10) was treated with DIBAL-H (1.0 M solution in hexanes). Aliquots were removed during the course of the reaction and analyzed by GC/MS. The GC/MS confirmed reduction to the aldehyde (11). After 5 h, the GC/MS trace showed no starting material, few byproducts and compound 11 (>90% by area). During the mild acidic workup, however, decomposition was found to occur, and no aldehyde was recovered. Several workup procedures were attempted, but each led to the same result; decomposition of the aldehyde and no isolation was achieved.

Figure 17:
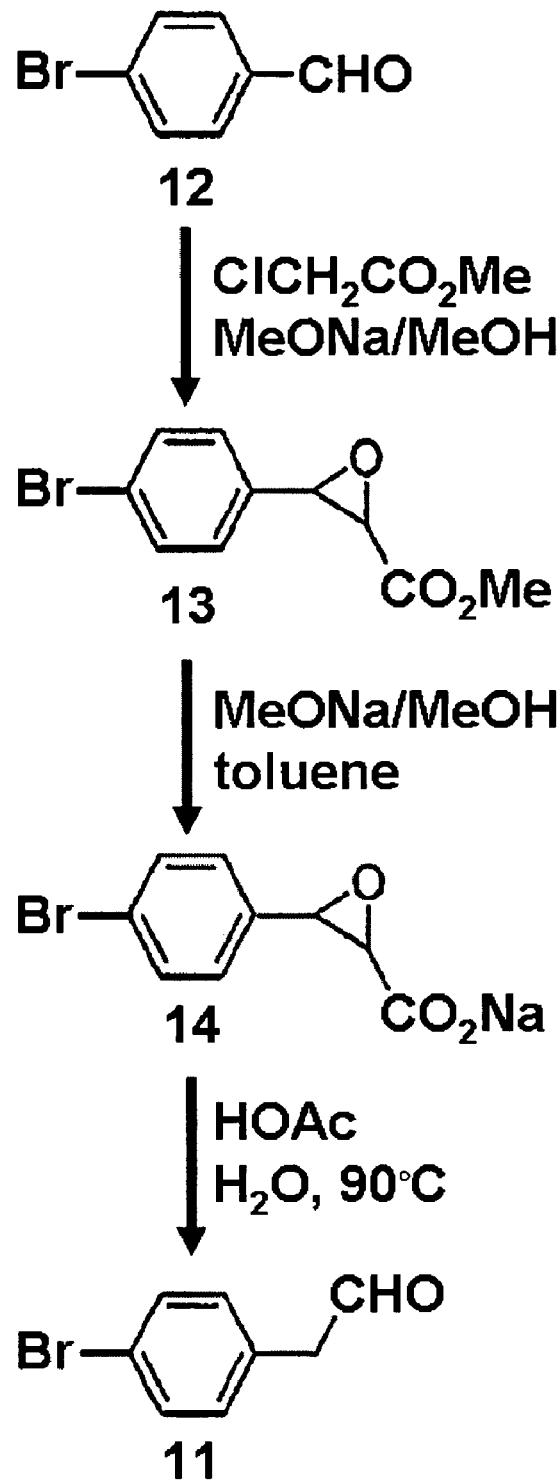
FIG. 17 illustrates synthesis Scheme 3.

Because we could not prepare aldehyde 11 using the path in the equation shown in FIG. 16, we chose an alternate route to this compound. Our second attempt to prepare 11 utilized the Darzens reaction (Scheme 3, FIG. 17). Commercially available 4-bromobenzaldehyde (12) and methyl chloroacetate in methanol were added to a solution of methanolic sodium methoxide. The resulting glycidic ester (13) was saponified with sodium methoxide in toluene, affording 14. Compound 14 was acidified and decarboxylated in one flask respectively, affording aldehyde 11 in 58% overall yield.

Figure 18:
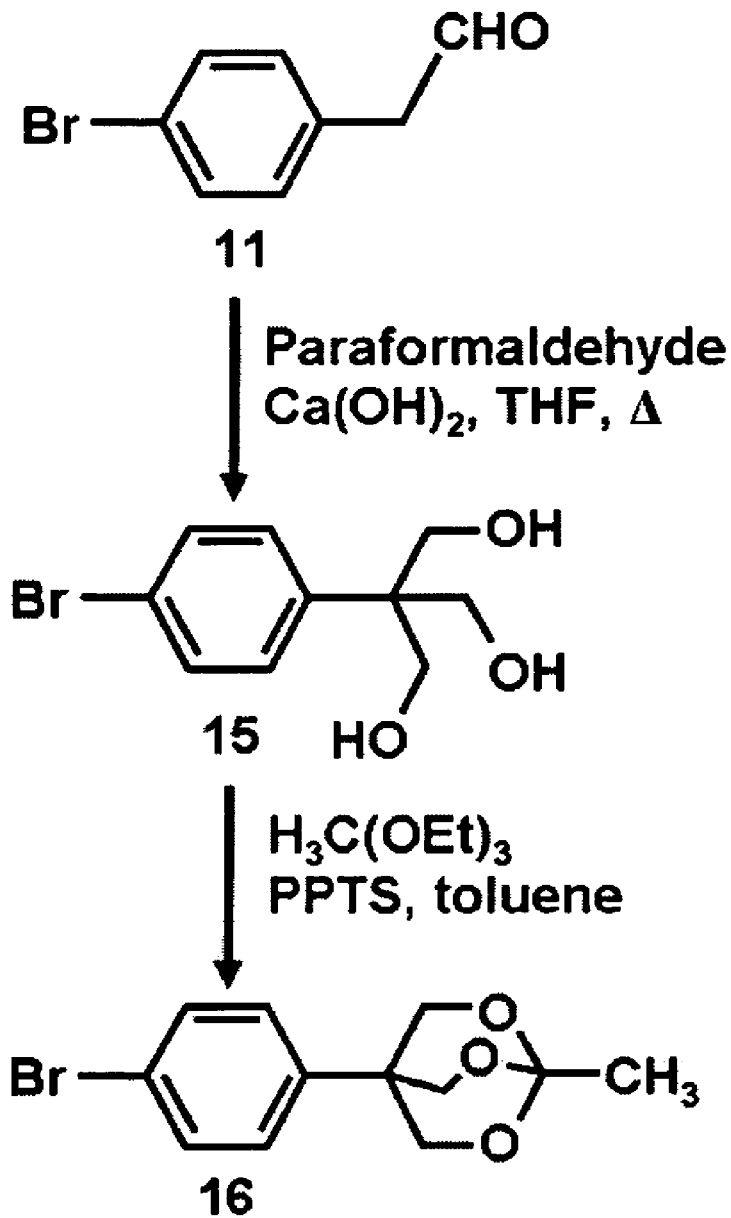
FIG. 18 illustrates synthesis Scheme 4.

With compound 11 in hand, a Tollens condensation to obtain trialcohol 15 was performed (Scheme 4, FIG. 18). Compound 11 was treated with excess paraformaldehyde (6.5 eq, and $Ca(OH)_2$ (0.8 eq) in THF (1.5 M) at 60-63° C. for 3 d. The resulting crude reaction mixture was filtered through Celite, and the filtrate was concentrated and chromatographed. In this manner, nearly pure 15 was obtained. We thought it advisable to protect trialcohol 15 as its ortho ester in subsequent reactions. Therefore, 15 was treated with triethyl orthoacetate (1.1 eq) and p-toluenesulfonic acid (0.5 mol %) in toluene to afford ortho ester 16 in 41% yield (from 11). Compound 16 serves as a Suzuki coupling partner to prepare Zn-9.

Figure 19:
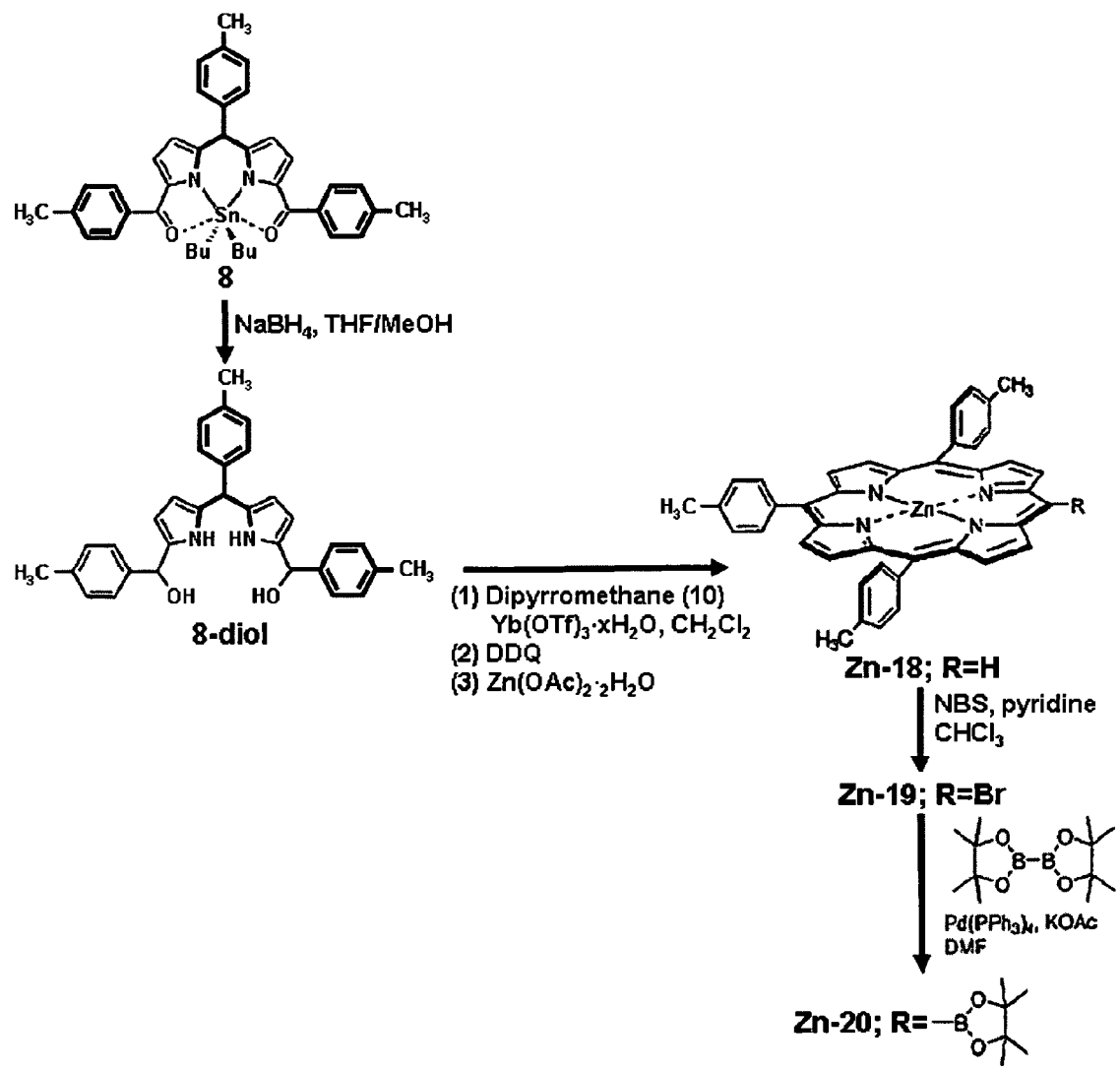
FIG. 19 illustrates synthesis Scheme 5.

The synthesis of the porphyrin Suzuki coupling partner is outlined in Scheme 5 (FIG. 19). Reduction of compound 8 was achieved with NaBH in THF/MeOH. The resulting dipyrromethane-dicarbinol (8-diol) was condensed with dipyrromethane (17) under $Yb(OTf)_3.xH_2O$ catalysis in $CH_2Cl_2$. After 15 min, the bulk was oxidized with DDQ. After 30 min, the crude porphyrin mixture was metalated with Zn $(OAc)_2.2H_2O$, affording Zn-18 in 16% yield. The crude reaction mixture did not contain any other porphyrins arising from acidolysis. Bromination of Zn-18 was readily achieved with NBS in $CHCl_3$ containing pyridine to afford Zn-19 in 92% yield. Last, Zn-19 was subjected to a Miyaura coupling with bis(pinacolato)diboron under Pd-mediated catalysis conditions. In this manner, porphyrin Zn-20 was prepared in 92% yield. For this reaction, an excess of the diboron species (10 eq) with respect to the porphyrin was employed to expedite coupling. Also, 10 mol % of $Pd(PPh_3)_4$ was employed in this reaction.

Figure 20:
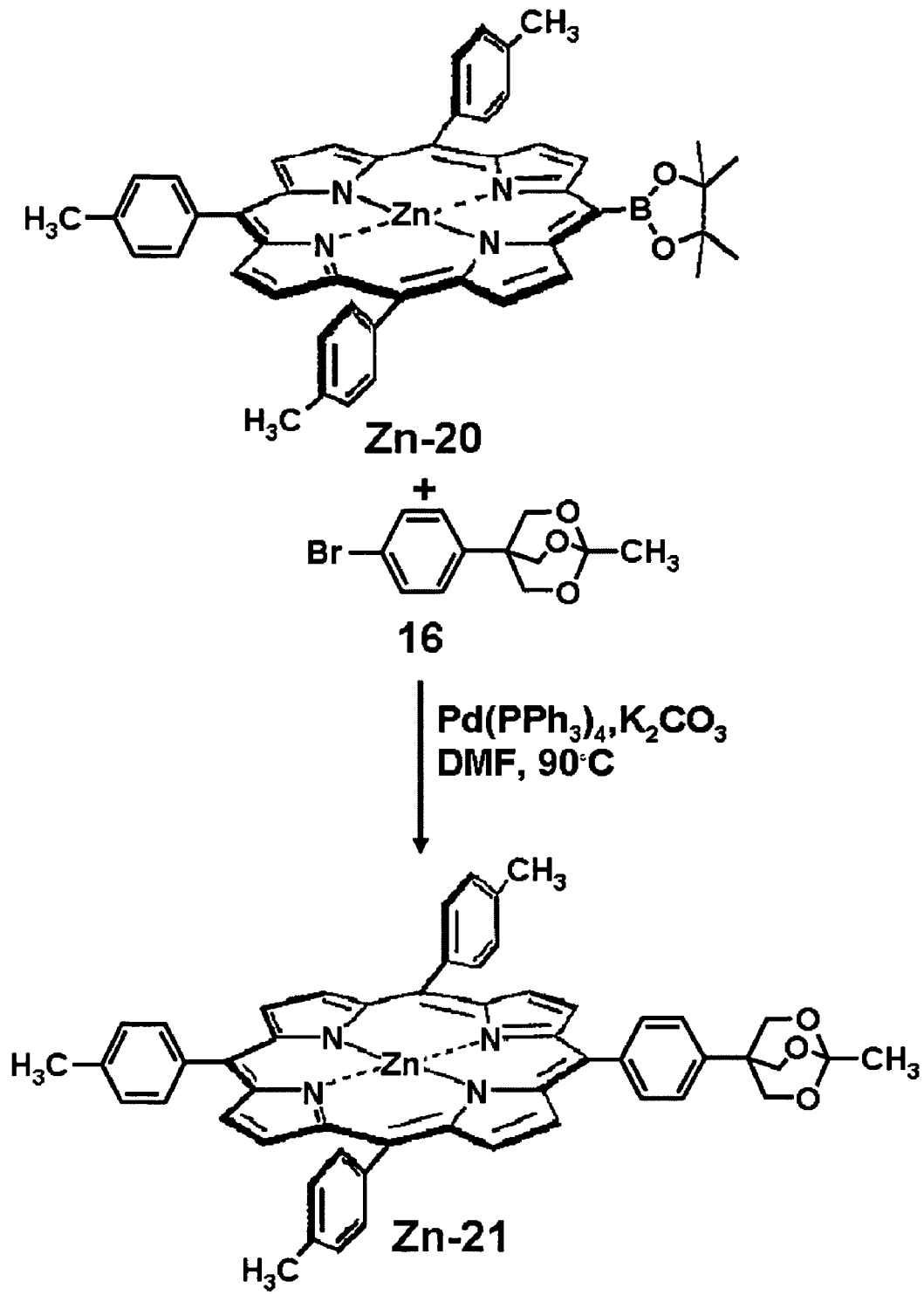
FIG. 20 illustrates synthesis Scheme 6.

With both Suzuki coupling partners in hand (16 and Zn-20), a Suzuki coupling reaction was performed (Scheme 6, FIG. 20). The progress of the reaction was followed by TLC and LD-MS. Both TLC and LD-MS confirmed the presence of the desired product, Zn-21. There were also small amounts of other porphyrin byproducts which were found to be a meso-meso linked dimer and an $A_3B$ porphyrin where A=p-tolyl and B=phenyl. The latter porphyrin byproduct was likely formed by a ligand transfer from the catalyst to the porphyrin. Such reactions are known. Nevertheless, these porphyrin impurities were readily separated from the desired product and porphyrin Zn-21 was obtained in 40% yield.

Figure 21:
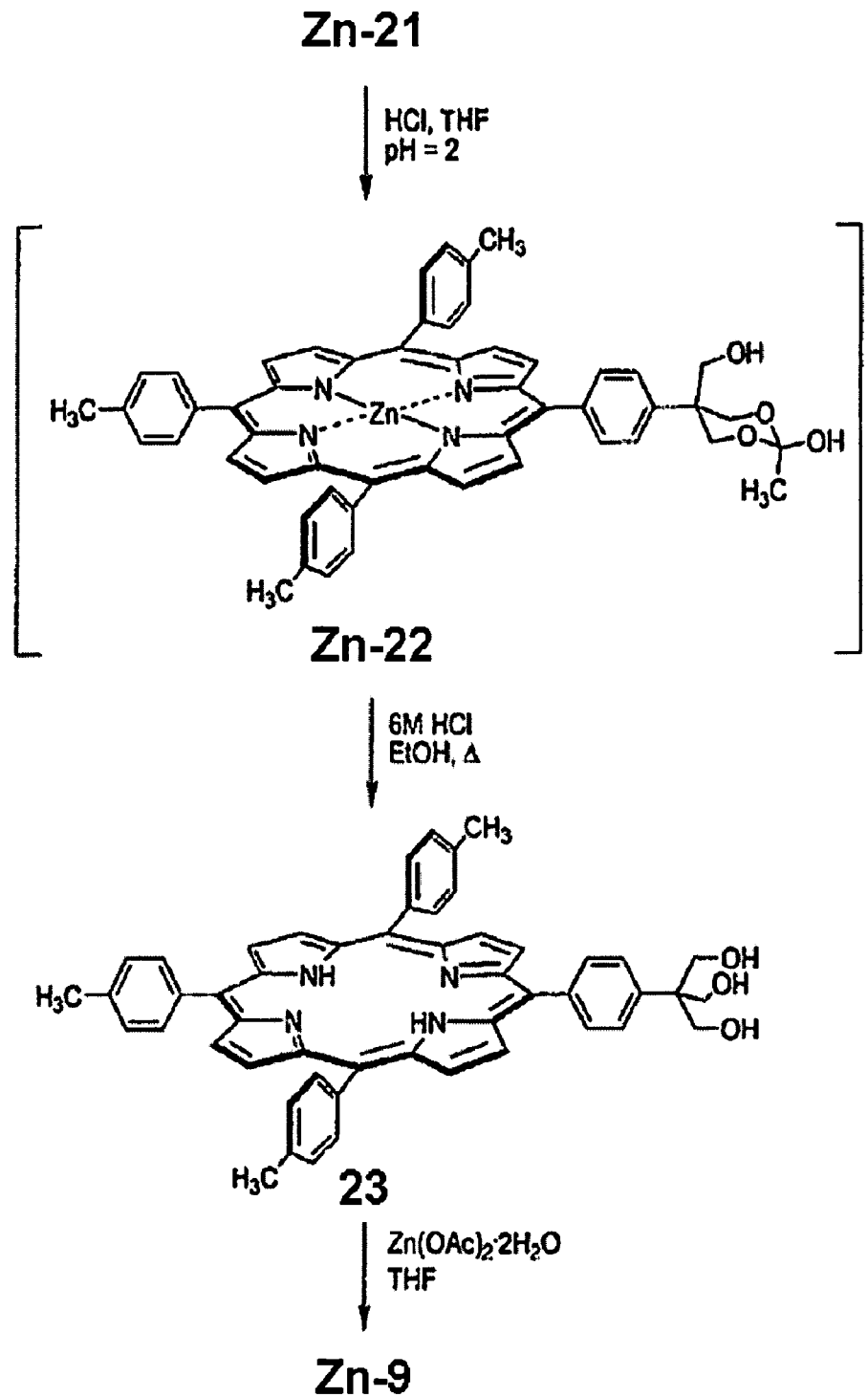
FIG. 21 illustrates synthesis Scheme 7.

Removal of the ortho ester protecting group is shown in Scheme 7 (FIG. 21). Treatment of Zn-21 with HCl (pH=2) in THF showed no starting material by TLC within minutes. The resulting porphyrin isolated was actually determined to be Zn-22, an intermediate byproduct formed during the deprotection. To achieve full deprotection, harsher conditions were required. Heating the porphyrin in 6M HCl in ethanol for 3 h, followed by neutralization and workup, afforded porphyrin 23 (the zinc porphyrin is readily demetalated under these conditions). Remetalation with $Zn(OAc).2H_2O$ in THF afforded target porphyrin Zn-9 in 68% yield. We have also attempted to prepare target porphyrin Zn-9 using alternate synthetic approaches. These approaches are outlined in detail in the Supporting Information.

Conclusions

We have prepared a zinc porphyrin bearing three alcohol groups in a tripodal architecture for attachment to electroactive surfaces. Such porphyrins are expected to yield highly stable, high charge-storage density SAMs.

Experimental Section

Non-Commercial Compounds.

Compounds 8, 8-diol, Zn-18, and Zn-19 were prepared as described in the literature.

Methyl 3-(4-bromophenyl)glycidate (13)

To a 1-L three-neck 24/40 round-bottomed, glass jacketed flask equipped with a water inlet/outlet, an overhead stirrer, a thermometer, an addition funnel, and $N_2$ inlet was added NaOMe (242 mL; 13% w/w solution in MeOH). To the addition funnel was added a solution of 4-bromobenzaldehyde (80.0 g, 432 mmol), methyl chloroacetate (57.0 mL, 649 mmol; 1.5 eq) in MeOH (240 mL). The reaction vessel was cooled to −8° C. To the flask was added the solution from the addition funnel dropwise keeping the temperature below −4°

C. After the addition was complete (~1 h), the solution was stirred at −5° C. for 2 h, then allowed to warm to room temperature and stirred overnight. Next morning, the cloudy white mixture was poured over 0.84 L of cold water containing AcOH (5 mL). A brown oil results. EtOAc (800 mL) was added and the mixture was transferred to a 4-L separatory funnel. The organic layer was separated, dried ($Na_2SO_4$), filtered and concentrated to a brown oil. The residue was dried further under a high vacuum for 1 h. The residue was found to be sufficiently pure by GC/MS and TLC to be used in the next reaction. Recovered 106 g.

Sodium salt of 3-(4-bromophenyl)glycidic acid (14)

To a 1-L three-neck 24/40 round-bottomed, glass jacketed flask equipped with a water inlet/outlet, an overhead stirrer, a thermometer, an addition funnel and $N_2$ inlet was added 100 g (388 mmol) of 13 and toluene (500 mL). The reaction vessel was cooled to 2° C. A solution of NaOMe (85 mL, 388 mmol) was added dropwise from an addition funnel, keeping the temperature below 3° C. After the addition, $H_2O$ (8.7 mL) was added and the reaction mixture quickly became thick with precipitate. The mixture was stirred for 2 h. The reaction mixture was filtered and washed with $Et_2O$ (1 L). The recovered solid was placed under high vacuum for 6 h. The recovered off white solid was used directly in the next step.

4-Bromophenylacetaldehyde (11)

To a 2-L three-neck 24/40 round-bottomed flask equipped with a reflex condenser, an overhead stirred, a thermometer, and $N_2$ inlet was added 100 g (377 mmol) of 14, water (1.0 L), and acetic acid (54.0 mL, 944 mmol). The reaction mixture was slowly heated to 90° C. and stirred at 90° C. for 2 h. The reaction mixture was cooled, and toluene (300 mL) was added. The organic layer was separated. The aqueous layer was washed with toluene (200 mL). The organic layers were combined, dried ($MgSO_4$), filtered, and concentrated. The residue was dried further under high vacuum for 2 h. Column chromatography (silica, $CH_2Cl_2$) affords an off-white solid. Recovered 49.7 g (58% yield from 4-bromobenzaldehyde). GC/MS shows only one peak.

2-(4-Bromophenyl)-1,3-dihydroxy-2-(hydroxymethyl)propane (15)

To a 50-mL three-neck 14/20 round-bottomed flask equipped with a stir bar, a reflex condenser, a thermometer, and N2 inlet was added samples of 11 (6.00 g, 30.1 mmol), paraformaldehyde (5.90 g, 196 mmol), $Ca(OH)_2$ (1.79 g, 24.2 mmol), and THF (22 mL). The cloudy white mixture was heated to 63° C. and stirred at this temperature for 3 d. The reaction mixture was then cooled and filtered through Celite. The filtrate was concentrated to a viscous, pale yellow oil. The residue was pumped on under high vacuum at 100° C. (to remove volatiles) for 1 h. Column chromatography (silica, EtOAc) afforded a pale yellow viscous oil which was mostly pure by TLC. This oil was used directly in the next step.

1-Methyl-4-(4-bromophen-1-yl)-2,6,7-trioxabicyclo[2.2.2]octane (16)

To a 250-mL single-neck 24/40 round-bottomed flask equipped with a stir bar and $N_2$ inlet was added 15 (5.7 g, not pure), triethyl orthoacetate (4.03 mL, 22.1 mmol) and toluene (42 mL). A biphasic mixture results. A sample of p-toluenesulfonic acid (21 mg, 0.11 mmol) was then added. After a few minutes, a clear, colorless solution is noted. After 1 h, the solution is concentrated to a yellow solid. Column chromatography (silica, $CH_2Cl_2$) affords 3.4 g (39% from 12) of a white solid. GC/MS shows only one peak.

Zn(II)-5,10,15-tri-p-tolyl-20-(pinacolboryl)porphyrin (Zn-20)

Samples of Zn-19 (300 mg, 0.415 mnol), $Pd(PPh_3)_4$ (48 mg, 0.042 mmol), bis(pinacolato)diboron (1.05 g, 4.15 mmol, 10 eq), and KOAc (407 mg, 4.15 mmol) in DMF (42 mL) were combined and heated to 80° C. under $N_2$. The mixture is stirred at this temperature overnight. The reaction mixture was concentrated. The residue was partitioned between water (100 mL) and $CHCl_3$ (100 mL). The organic layer was collected. The aqueous layer was washed with $CHCl_3$ (50 mL). The organic layers were combined, dried ($MgSO_4$), filtered, and concentrated. Column chromatography (silica, $CH_2Cl_2$/hexanes, 1:1, 4×20 cm) affords 288 mg (90% yield) of the title compound.

Zn(II)-5,10,15-tri-p-tolyl-20-[4-(1-methyl-2,6,7-trioxabicyclo[2.2.2]octan-4-yl)phenyl]porphyrin (Zn-21)

To samples of 16 (280 mg, 0.975 znmol), Zn-20 (150 mg, 0.195 mmol), $Pd(PPh_3)_4$ (23 mg, 0.020 mmol), and $K_2CO_3$ (135 mg, 0.975 mmol) in DMF (20 mL) were combined and heated to 90° C. under $N_2$. The mixture is stirred at this temperature overnight. The reaction mixture was concentrated. The residue was partitioned between THF (50 mL) and half-saturated aqueous $NH_4Cl$ (50 mL). The organic layer was separated and the aqueous layer was washed with additional THF (50 mL). The organic layers were collected, dried ($Na_2SO_4$), filtered, and concentrated. Column chromatography (silica, $CHCl_3$/hexanes, 1:1, then $CHCl_3$) affords nearly pure product. A second column (silica, $CHCl_3$/THF, 98:2) afforded 93 mg (40% yield) of the title porphyrin.

5,10,15-tri-p-tolyl-20-[4-(1,3-dihydroxy-2-hydroxymethylprop-2-yl)phenyl]porphyrin (23)

A sample of Zn-21 was dissolved in THF (11 mL). To this solution was added HCl (1 mL of a 2 M solution in $H_2O$). The solution was stirred at room temperature for 30 TLC showed no starting material. TEA (0.200 mL) was added and the mixture was concentrated. Analysis of the residue by LD-MS did not show the expected product but rather an intermediate porphyrin (Zn-22). To fully deprotect the porphyrin, the residue was partially suspended in EtOH/THF (15 mL, 10:1) and treated with 6 M HCl (2 mL). The green solution was heated to reflux for 2 h (LD-MS showed the presence of 23). The solution was cooled and saturated aqueous $K_2CO_3$ was slowly added to neutralize the solution. To the resulting magenta mixture was added THF (50 mL) followed by brine (50 mL). The organic layer was collected, dried ($MgSO_4$), filtered, and concentrated. Recovered 71 mg (90%) of a purple solid which was used directly in the next step.

Zn(II)-5,10,15-tri-p-tolyl-20-[4-(1,3-dihydroxy-2-hydroxymethylprop-2-yl)phenyl]porphyrin (Zn-9)

A sample of 23 was dissolved in THF (15 mL) and treated with a sample of $Zn(OAc)_2.2H_2O$ (102 mg, 0.467 μmol) and stirred at room temperature for 18 h. To the solution was added a half-saturated solution of aqueous $NH_4Cl$. The organic layer was collected, dried ($MgSO_4$), filtered, and concentrated. Column chromatography (silica, THF/$CH_2Cl_2$, 1:1) afforded the title porphyrin in 62% yield (48 mg) as a purple solid.

Supporting Information

Results and Discussion

Figure 22:
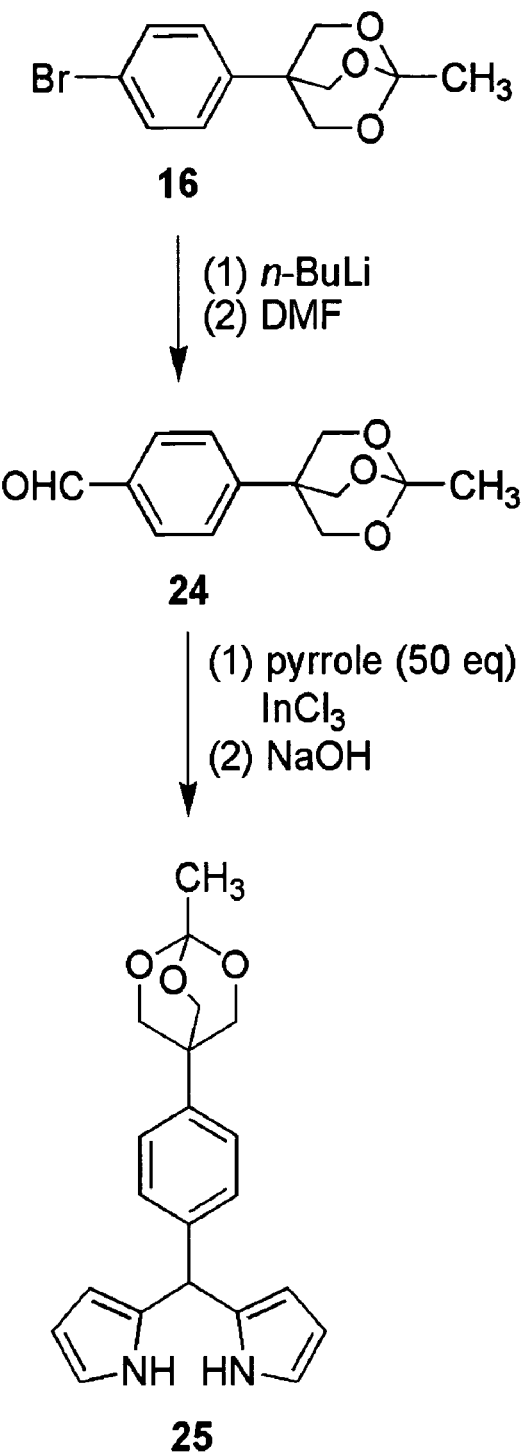
FIG. 22 illustrates synthesis Scheme 8.
Figure 23:
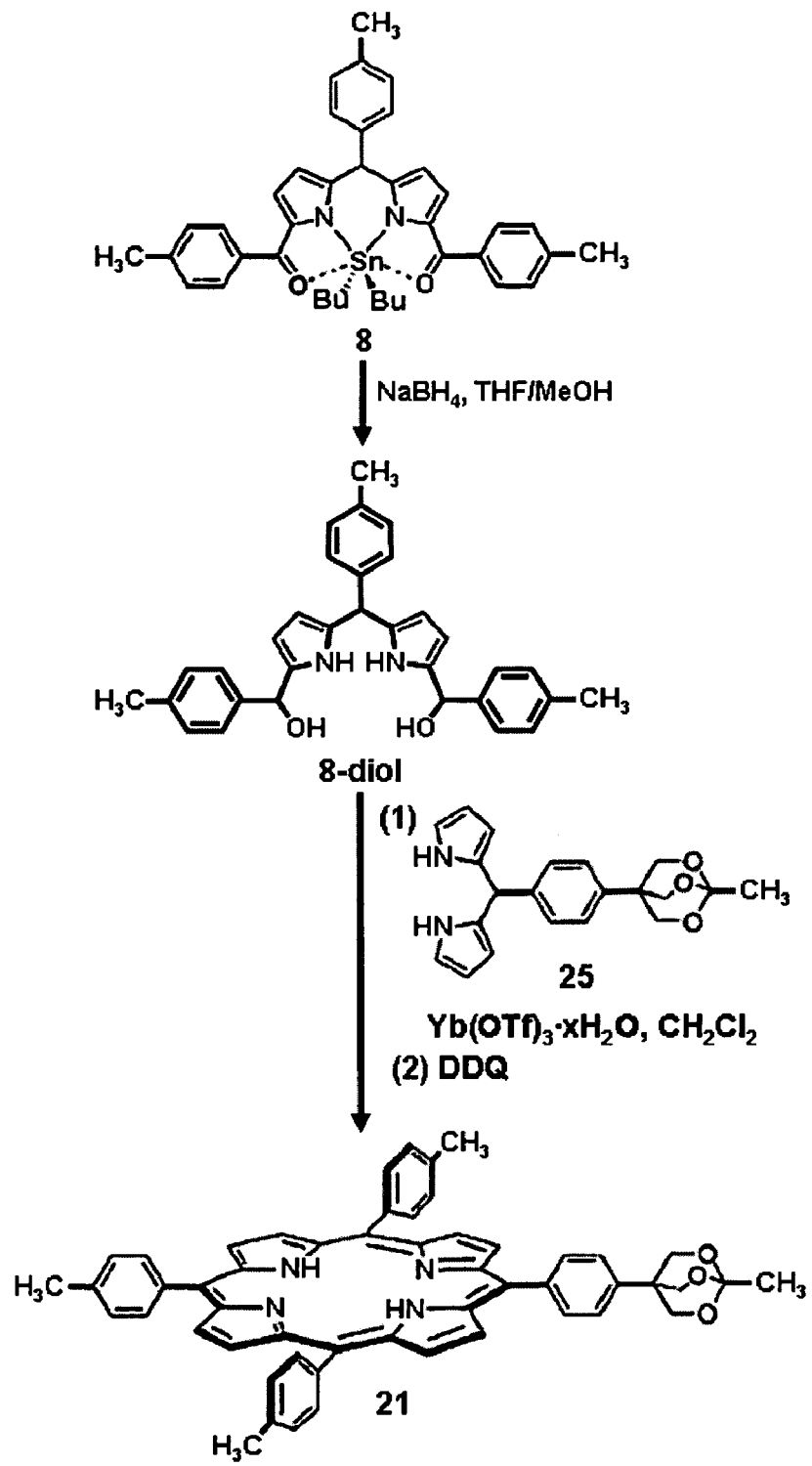
FIG. 23 illustrates synthesis Scheme 9.

In addition to the synthetic route described above to prepare Zn-9 we sought other synthetic methods to prepare Zn-9. We decided to prepare a dipyrromethane bearing an ortho ester group which could be directly condensed with a dipyrromethane-dicarbinol. The synthesis of this dipyrromethane (25) is shown in Scheme 8 (FIG. 22). Compound 16 was treated with n-BuLi in THF. The resulting carbanion was quenched with DMF affording aldehyde 24. The aldehyde was condensed with excess pyrrole under $InCl_3$ catalysis at room temperature for 1.5 h. After chromatographic workup, dipyrromethane 25 was isolated in 24% yield. This dipyrromethane was condensed with 8-diol (Scheme 9, FIG. 23)

under Yb(OTF$_3$.xH$_2$O) catalysis. Aliquots were removed at 2, 4, and 6 min, oxidized, and analyzed by UV/Vis spectroscopy. The spectroscopic yields were found to be 13%, 10% and 29%, respectively. However, after adding DDQ to the bulk solution, the spectroscopic yield reached essentially zero within a few minutes.

Figure 24:
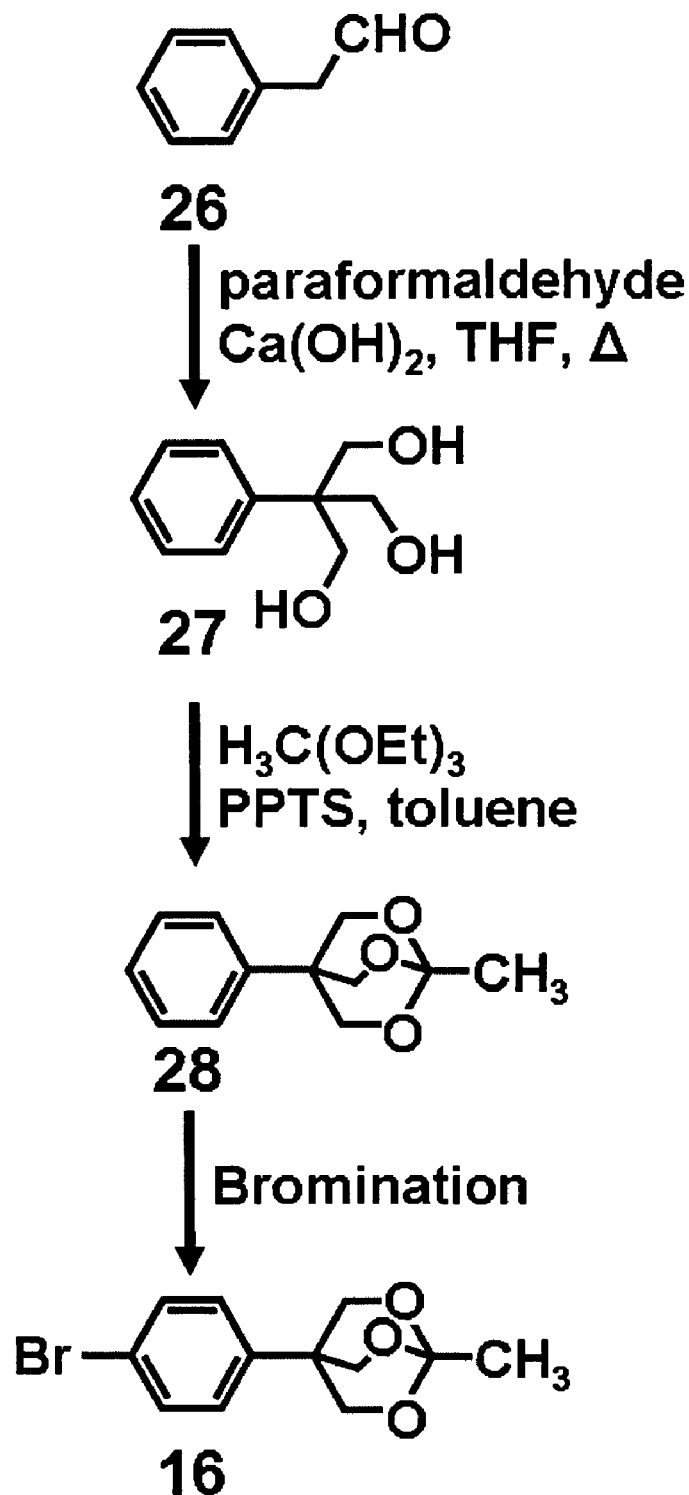
FIG. 24 illustrates synthesis Scheme 10.

Another synthetic route to prepare Zn-9 is shown in Scheme 10, FIG. 24. Commercially available phenylacetaldehyde (26) was subjected to a Tollens' reaction following a literature procedure. The known target, 27, was isolated in 43% yield. Protection of the trialcohol was achieved by treatment of 27 with triethyl orthoacetate in toluene with p-toluenesulfonic acid monohydrate as catalyst. In this manner, compound 28 was isolated in quantitative yield. The ortho ester group mimics a t-butyl group in its steric demand. Electronically, the ortho ester group activates the phenyl ring towards electrophilic substitution reactions a little more than a t-butyl group. Second, regioselective halogenations of t-butylbenzene are known in the literature. Following this precedent, we sought to prepare compound 16 directly from 28 via an electrophilic bromination reaction. We tried several reaction conditions [(1) NBS, TBF; (2) Br$_2$, CHCl$_3$; (3) Br$_2$, FeBr$_3$, K$_2$CO$_3$, CHCl$_3$; (4) Br$_2$, K$_2$CO$_3$, CHCl$_3$] and found none of the conditions tried gave any appreciable amount of 16. Therefore, we abandoned this synthetic route.

Experimental Section 1-(4-Formylphenyl)-4-methyl-2,6,7-trioxabicyclo[2.2.2]octane (24)

Compound 16 (3.00 g, 10.4 mmol) was dissolved in THF (50 mL). The solution was cooled to −5° C. To the solution was added n-BuLi (4.60 mL, 11.5 mmol, 2.5 M solution in hexanes), keeping the temperature below −2° C. After 1 h, DMF (1.60 mL, 20.8 mmol) was added. The mixture was stirred for 1 h, then saturated aqueous NH$_4$Cl (50 mL) was added. The organic layer was collected, dried (Na$_2$SO$_4$), filtered, and concentrated to a white solid. The solid was used directly in the next step.

5-[4-(1-methyl-2,6,7-trioxabicyclo[2.2.2]octan-4-yl)phenyl]dipyrromethane (25)

To a solution of 24 (2.50 g, 10.7 mmol) in pyrrole (37 mL, 534 mmol) was added InCl$_3$ (237 mg, 1.07 mmol). The mixture was stirred at room temperature for 1.5 h. Then, NaOH (1.28 g, 32.1 mmol) was added. The mixture was filtered and the filtrate was concentrated. Column chromatography (silica, CH$_2$Cl$_2$/EtOAc, 10:1) afforded a yellow solid (915 mg, 24% yield).

α,α,α-Tris(hydroxymethyl)toluene (27)

This compound was prepared according to a literature procedure in 43% yield (350 mmol scale).

1-Methyl-4-bromophenyl-2,6,7-trioxabicyclo[2.2.2]octane (28)

Compound 27 (20.0 g, 110 mmol), toluene (220 mL), and triethyl orthoacetate (22.0 mL, 120 mmol) were added to a round-bottomed flask. A biphasic mixture resulted. To the mixture was added p-toluenesulfonic acid monohydrate (105 mg). After a few minutes, a clear, colorless solution was obtained. After 2 h, the reaction mixture was concentrated to a white solid and further dried under high vacuum for 6 h. Recovered 22.9 g (100% yield) of a white solid.

Example 3

Preparation of Porphyrin Bipods Containing an Activating Group and Porphyrins Containing a Heteroatom-Based Bipodal Chain This example describes a synthesis methodology for the facile preparation of bipodal redox-active molecules (e.g., porphyrins) bearing an activating group at the key quaternary carbon atom. Judicious choice of activating group allows later removal of the same resulting in the preparation of otherwise unsubstituted bipodal linkers attached to redox-active molecules.

Alternative routes to such bipodal tethers are available that do not require an activating group at the key quaternary carbon. Such routes provide access to bipodal tethers where the non-linking carbon substituent can be H, alkyl, or aryl.

In certain embodiments, preparation of a novel class of porphyrin molecules, bearing a bipodal linker group, is accomplished by making use of an aryl-bonded activating group, such as cyano, carbalkoxy, alkyl- or aryl sulfonyl, etc., in such a way to facilitate the creation of the key arylalkyl quaternary carbon center that will serve as the anchoring point for the bipodal chains. Notice that the selected activating groups allow for the introduction of the bipodal linker chains in more than one way, namely, one can resort to the use of standard alkylation conditions, 1,4-addition reactions, and even phase transfer conditions.

Figure 25:
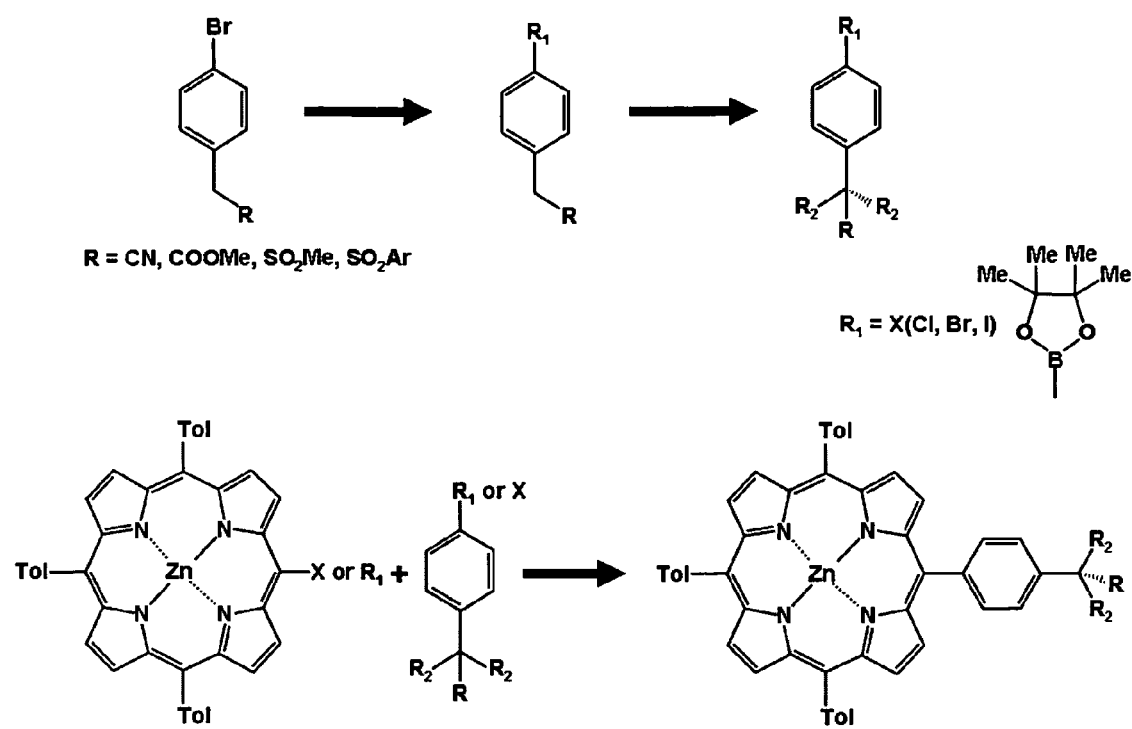
FIG. 25 illustrates the preparation of p-disubstituted aromatic compounds that bear the selected "activating" moiety as a benzylic substituent, thus doubly activating that center for the subsequent alkylation/addition reaction.

The preparation of p-disubstituted aromatic compounds that bear the selected "activating" moiety as a benzylic substituent, thus doubly activating that center for the subsequent alkylation/addition reaction is illustrated in FIG. 25. Notice that the para-substituent in such setup is used to either couple directly to the meso-substituted porphyrin molecule or as a precursor to the final coupling partner. This coupling reaction typically takes the form of a Pd-catalyzed Suzuki coupling (see, e.g., Chiellini, et al. (1978) *J. Organic Chem.*, 43(12): 2550-2551; Yu, L.; Lindsey (2001) *Tetrahedron*, 57: 9285, U.S. Pat. No. 4,035,376) and the like.

Alternatively, in certain embodiments, redox-active molecules (e.g., porphyrins) bearing a disubstituted heteratom—hence, leading also to the preparation of bipodal porphyrins—linked directly to the 4-position of the meso-aryl substituent may be obtained through the application of the well-known Pd-catalyzed amination of aryl halides or sulfonates in such a way as to introduce directly an aryl-linked heteroatom-supported bipodal chain.

Use of various substituted N,N-dialkenyl amines (e.g., N,N-diallyl amine) or the corresponding N,N-dialkanolamines (e.g., N,N-diethanolamine) leads to the ready preparation of a novel class of bipodal porphyrins.

Figure 26:
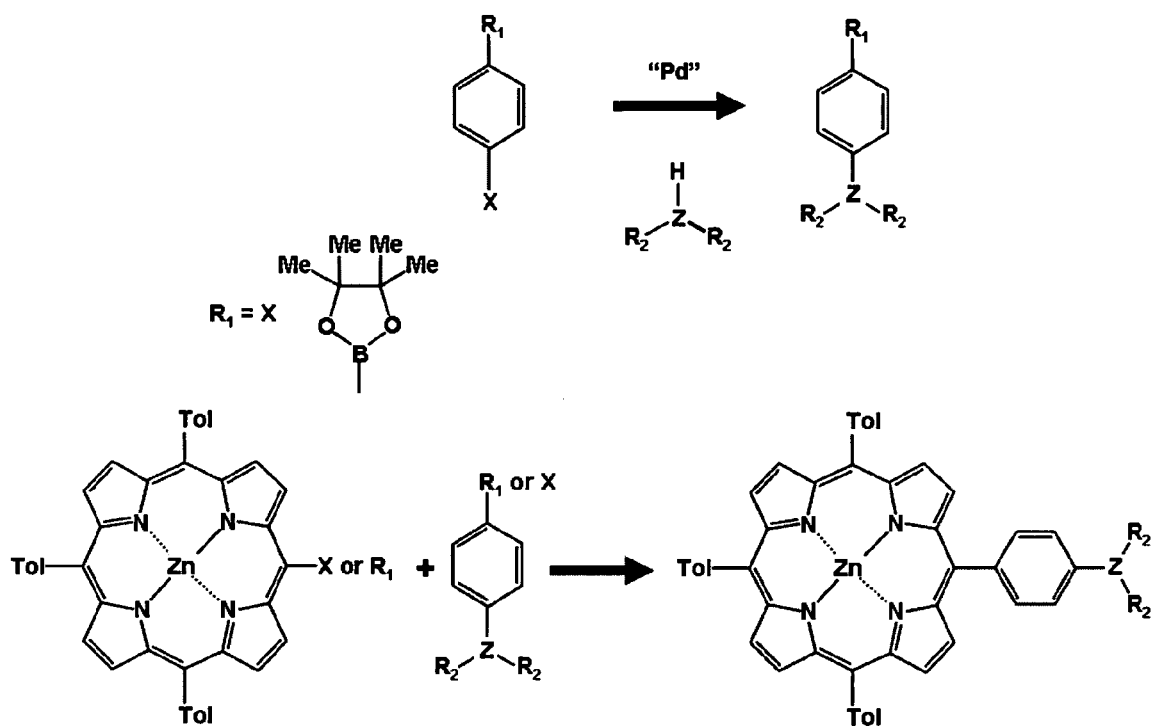
FIG. 26 illustrates the use of a Pd-catalyzed Suzuki amination reaction for the one-step introduction of an otherwise unsubstituted bipod series bearing a heteroatom (Z=N, P, B, other) at the cusp position.

The use of a Pd-catalyzed Suzuki amination reaction allows for the one-step introduction of an otherwise unsubstituted and totally novel bipod series bearing a heteroatom (Z=N, P, B, other) at the cusp position, as shown in FIG. 26.

The aromatic amination reaction is well-known (see, e.g., Hartwig (2002) *Palladium-catalyzed Amination of Aryl Halides and Sulfonates*, In: Modern Arene Chemistry, D. Astruc, Editor, Wiley-VCH Verlag GmbH and references cited therein; and Yang and Buchwald (1999) *J. Organometal. Chem.*, 576(1-2): 125-146 and references cited therein).

In addition, the described methodologies are simple enough to incorporate all kinds of substituents about the porphyrin ring (or in other redox-active moieties) as the linker/tether combination is introduced at a later stage in the synthesis. The Pd-catalyzed Suzuki coupling reaction has been used extensively in porphyrin synthesis and is known to be fully compatible with a plethora of substituents. For example Yu and Lindsey (2001) *Tetrahedron* 57: 9285-9298, describe the typical Pd-catalyzed coupling conditions, as follows: Catalyst: Pd(PPh$_3$)$_4$ (5-15 mol %), Base: K$_2$CO$_3$ (1-2 eqs. based on the boronic ester or boronic acid used), Solvent(s): Toluene, toluene/DMF (90:10), DMF, Concentration: 10 mM (perhaps higher concentrations can be used), Temperature: 80-100° C., Time: 1 h to 24 h which provides good to moderate yields.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes and to the same extent as if each individual publication or patent application was specifically and individually indicated to be incorporated by reference.

What is claimed is:

1. A composition comprising an array of electrodes, a plurality of said electrodes each comprising a redox-active molecule selected from the group consisting of a porphyrinic macrocycle, a sandwich compound of the formula $L^1$-M-$L^2$ or the formula $L^1$-$M^1$-$L^2$-$M^2$-$L^3$ where M, $M^1$, and $M^2$ are independently selected metals and $L^1$, $L^2$, and $L^3$ are independently selected porphyrins or porphyrinic macrocycles, and a metallocene, wherein said redox-active molecule is attached to the electrode by a polypodal tether wherein said polypodal tether is a 2-podal, 3-podal, 4-podal, or 5-podal tether, the legs of said tether do not contain a benzene and each leg of said tether contains at least one carbon and not more than 10 carbons.

2. The composition of claim 1, wherein said composition comprises a tripod tether and excludes tethers having the formula:

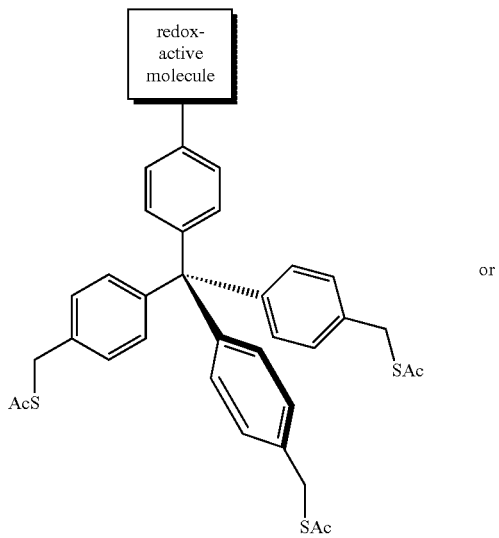

or

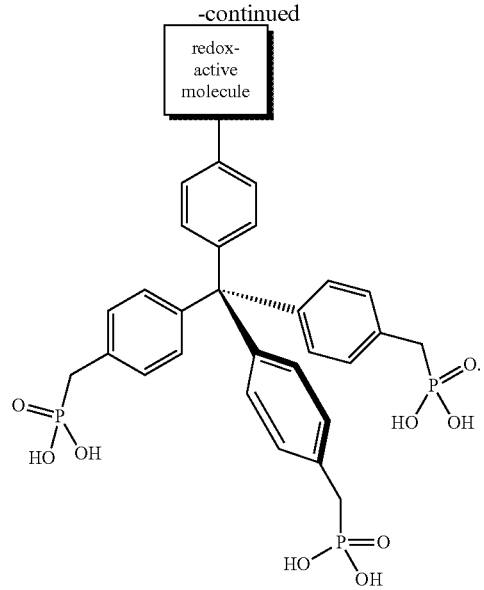

3. The composition of claim 2, wherein the redox-active molecule attached to a tripod tether has the formula:

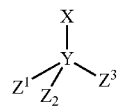

wherein:

X is said redox-active molecule;

Y is selected from the group consisting of a heteroatom, a carbon, a straight chain substituted or unsubstituted hydrocarbon, a branched hydrocarbon, and a cyclic hydrocarbon;

$Z^1$, $Z^2$, and $Z^3$ are independently selected from the group consisting of alkyl, aryl, heterocycle, vinylalkyl, ethynylalkyl, hydroxyalkyl, and carboxyalkyl.

4. The composition of claim 3, wherein, when Y is not a carbon or a heteroatom, at least two of $Z^1$, $Z^2$, and $Z^3$ are attached to different atoms.

5. The composition of claim 3, wherein X is a porphyrin.

6. The composition of claim 2, wherein Y is selected from the group consisting of, a two carbon alkyl, a 3 carbon alkyl, and a 4 carbon alkyl, and a cyclic hydrocarbon.

7. The composition of claim 6, wherein Y is a cyclic hydrocarbon selected from the group consisting of carboranyl ($C_2B_{10}H_{12}$), carboranyl ($C_2B_8H_{10}$), staffane, cubanediyl, bicyclo[2.2.2]octanediyl, cyclohexyl, cyclopentyl, and adamantyl.

8. The composition of claim 2, wherein Y is carbon.

9. The composition of claim 2, wherein Y is a heteroatom.

10. The composition of claim 2, wherein at least one of the legs of said tripod tether is selected from the group consisting of an alcohol, a hydroxyalkyl, an alkyl, an allyl, an allyl-terminated hydrocarbon, an alkyne, an alkyne-terminated hydrocarbon, and an ethyleneoxy unit (—CH$_2$CH$_2$—O—).

11. The composition of claim 10, wherein all three legs of said tripod tether are selected from the group consisting of an alcohol, a hydroxyalkyl, an alkyl, an allyl, an allyl-terminated hydrocarbon, an alkyne, an alkyne-terminated hydrocarbon, and an ethyleneoxy unit (—CH$_2$CH$_2$—O—).

12. The composition of claim 10, wherein all three legs of said tripod tether are identical.

13. The composition of claim 10, wherein said alkyl is a substituted alkyl.

14. The composition of claim 13, wherein said substituted alkyl is an alkylallyl.

15. The composition of claim 14, wherein said redox-active molecule attached to the tether has the formula:

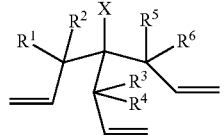

wherein:
X is said redox-active molecule;
$R^1$, $R^2$, $R^3$, $R^4$, $R^5$, and $R^6$ are independently selected from the group consisting of H, OH, and alkyl; and
when $R^1$ and $R^2$ are the same they are both OH, and when $R^3$ and $R^4$ are the same they are both H or methyl, and when $R^5$ and $R^6$ are the same they are both H or methyl.

16. The composition of claim 15, wherein $R^1$, $R^2$, $R^3$, $R^4$, $R^5$, and $R^6$ are all H.

17. The composition of claim 13, wherein said substituted alkyl is a hydroxyalkyl.

18. The composition of claim 17, wherein said redox-active molecule attached to a tether has the formula:

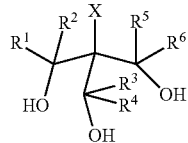

wherein
$R^1$, $R^2$, $R^3$, $R^4$, $R^5$, and $R^6$ are independently selected from the group consisting of H, OH, and alkyl; and
when $R^1$ and $R^2$ are the same they are both H or methyl, when $R^3$ and $R^4$ are the same they are both H or methyl, and when $R^5$ and $R^6$ are the same they are both H or methyl.

19. The composition of claim 18, wherein $R^1$, $R^2$, $R^3$, $R^4$, $R^5$, and $R^6$ are all H.

20. The composition of claim 2, wherein at least one of the legs of said tripod tether is an aryl.

21. The composition of claim 20, wherein said aryl is a substituted aryl.

22. The composition of claim 21, wherein said substituted aryl has a substituent selected from the group consisting of S-acetylthioalkyl, phosphonoalkyl, vinyl, allyl, ethynyl, propargyl, hydroxy, carboxy, cyano, amino, formyl, bromo, iodo, chloro, mercapto, selenyl, telluryl, phosphono, S-acetylthio, Se-acetylseleno, and Te-acetyltelluro.

23. The composition of claim 2, wherein the redox-active molecule is attached to a tripod tether selected from the group consisting of 3-vinylpenta-1,4-dien-3-yl,4-(3-vinylpenta-1,4-dien-3-yl)phenyl, 4-(3-vinylpenta-1,4-dien-3-yl)biphen-4'-yl, 4-allylhepta-1,6-dien-4-yl, 4-(4-allylhepta-1,6-dien-4-yl)phenyl, 4-(4-allylhepta-1,6-dien-4-yl)biphen-4'-yl, 5-(1-buten-4-yl)nona-1,8-dien-5-yl, 4-[5-(1-buten-4-yl)nona-1,8-dien-5-yl]phenyl, 4-[5-(1-buten-4-yl)nona-1,8-dien-5-yl]biphen-4'-yl, 3-ethynylpenta-1,4-diyn-3-yl, 4-(3-ethynylpenta-1,4-diyn-3-yl)phenyl, 4-(3-ethynylpenta-1,4-diyn-3-yl)biphen-4'-yl, 4-propargylhepta-1,6-diyn-4-yl, 4-(4-propargylhepta-1,6-diyn-4-yl)phenyl, 4-(4-propargylhepta-1,6-diyn-4-yl)biphen-4'-yl, 5-(1-butyn-4-yl)nona-1,8-diyn-5-yl, 4-[5-(1-butyn-4-yl)nona-1,8-diyn-5-yl]phenyl, 4-[5-(1-butyn-4-yl)nona-1,8-diyn-5-yl]biphen-4'-yl, 2-(hydroxymethyl)-1,3-dihydroxyprop-2-yl, 4-[2-(hydroxymethyl)-1,3-dihydroxyprop-2-yl]phenyl, 4-[2-(hydroxymethyl)-1,3-dihydroxyprop-2-yl]biphen-4'-yl, 3-(2-hydroxyethyl)-1,5-dihydroxypent-3-yl, 4-[3-(2-hydroxyethyl)-1,5-dihydroxypent-3-yl]phenyl, 4[-3-(2-hydroxyethyl)-1,5-dihydroxypent-3-yl,]biphen-4'-yl, 4-(3-hydroxypropyl)-1,7-dihydroxyhept-4-yl, 4-[4-(3-hydroxypropyl)-1,7-dihydroxyhept-4-yl]phenyl, 4-[4-(3-hydroxypropyl)-1,7-dihydroxyhept-4-yl]biphen-4'-yl, 2-(mercaptomethyl)-1,3-dimercaptoprop-2-yl, 4[2-(mercaptomethyl)-1,3-dimercaptoprop-2-yl]phenyl, 4-[2-(mercaptomethyl)-1,3-dimercaptoprop-2-yl]biphen-4'-yl, 3-(2-mercaptoethyl)-1,5-dimercaptopent-3-yl, 4-[3-(2-mercaptoethyl)-1,5-dimercaptopent-3-yl]phenyl, 4[3-(2-mercaptoethyl) -1,5-dimercaptopent-3-yl]biphen-4'-yl, 4-(3-mercaptopropyl)-1,7-dimercaptohept-4-yl, 4-[4-(3-mercaptopropyl)-1,7-dimercaptohept-4-yl]phenyl, 4-[4-(3-mercaptopropyl)-1,7-dimercaptohept-4-yl]biphen-4'-yl, 2-(selenylmethyl)-1,3-diselenylprop-2-yl, 4[2-(selenylmethyl)-1,3-diselenylprop-2-yl]phenyl, 4-[2-(mercaptomethyl)-1,3-dimercaptoprop-2-yl]biphen-4'-yl, 3-(2-selenylethyl)-1,5-diselenylpent-3-yl, 4-[3-(2-selenylethyl)-1,5-diselenylpent-3-yl]phenyl, 4-[3-(2-selenylethyl)-1,5-diselenylpent-3-yl]biphen-4'-yl, 4-(3-selenylpropyl)-1,7-diselenylhept-4-yl, 4-[4-(3-selenylpropyl)-1,7-diselenylhept-4-yl]phenyl, 4-[4-(3-selenylpropyl)-1,7-diselenylhept-4-yl]biphen-4'-yl, 2-(phosphonomethyl)-1,3-diphosphonoprop-2-yl, 4-[2-(phosphonomethyl)-1,3-diphosphonoprop-2-yl]phenyl, 4-[2-(phosphonomethyl)-1,3-diphosphonoprop-2-yl]biphen-4'-yl, 3-(2-phosphonoethyl) -1,5-diphosphonopent-3-yl, 4-[3-(2-phosphonoethyl)-1,5-diphosphonopent-3-yl]phenyl, 4-[3(2-phosphonoethyl)-1,5-diphosphonopent-3-yl]biphen-4'-yl, 4-(3-phosphonopropyl)-1,7-diphosphonohept-4-yl, 4-[4-(3-phosphonopropyl)-1,7-diphosphonohept-4-yl]phenyl, 4-[4-(3-phosphonopropyl)-1,7-diphosphonohept-4-yl]biphen-4'-yl, 2-(carboxymethyl)-1,3-dicarboxyprop-2-yl, 4-[2-(carboxymethyl)-1,3-dicarboxyprop-2-yl]phenyl, 4-[2-(carboxymethyl)-1,3-dicarboxyprop-2-yl]biphen-4'-yl, 3-(2-carboxyethyl)-1,5-dicarboxypent-3-yl, 4[3-(2-carboxyethyl)-1,5-dicarboxypent-3-yl]phenyl, 4-[3-(2-carboxyethyl)-1,5-dicarboxypent-3-yl]biphen-4'-yl, 4-(3-carboxypropyl)-1,7-dicarboxyhept-4-yl, 4-[4-(3-carboxypropyl)-1,7-dicarboxyhept-4-yl]phenyl, and 4-[4-(3-carboxypropyl)-1,7-dicarboxyhept-4-yl]biphen-4'-yl.

24. The composition of claim 2, wherein the redox-active molecule attached to a tripodal tether has the formula:

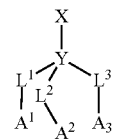

wherein:
X is said redox-active molecule;
Y is selected from the group consisting of a heteroatom, a carbon, a straight chain substituted or unsubstituted hydrocarbon, a branched hydrocarbon, and a cyclic hydrocarbon $L^1$, $L^2$, and $L^3$ are independently selected from the group consisting of a C, a two carbon alkyl, a 3 carbon alkyl, and a 4 carbon alkyl, and an ethyleneoxy; and $A^1$, $A^2$, and $A^3$ are surface attachment groups independently selected from the group consisting of bromo, iodo, hydroxy, formyl, vinyl, allyl, thiol, selenyl, S-acetylthio, S-acetylthio, mercapto, phosphono, carboxy, amino, cyano, and ethyne.

25. The composition of claim 24, wherein the redox-active molecule attached to a tripodal tether has the formula:

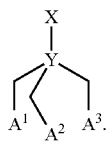

26. The composition of claim 24, wherein the redox-active molecule attached to a tripodal tether has the formula:

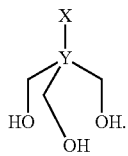

27. The composition of claim 24, wherein the redox-active molecule attached to a tether has the formula:

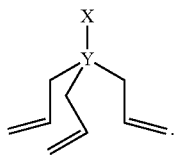

28. The composition of claim 1, wherein said composition comprises a bipod tether.

29. The composition of claim 28, wherein said composition comprises a redox-active molecule attached to a bipod tether, said redox-active molecule attached to a bipod tether having the formula:

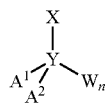

wherein:
X is said redox-active molecule;
Y is selected from the group consisting of a heteroatom, a carbon, a straight chain substituted or unsubstituted hydrocarbon, a branched hydrocarbon, and a cyclic hydrocarbon;
n is zero or one;
W, when present, is selected from the group consisting of H, alkyl, aryl, cyano, alkyl-sulfonyl, acyl, carboxyl, carboxy alkly, carboxaryl, arylsulfonyl, and aldehyde; and
$A^1$ and $A^2$ are independently selected from the group consisting of bromo, iodo, hydroxy, hydroxymethyl, formyl, bromomethyl, vinyl, allyl, thiol, selenyl, S-acetylthio, S-acetylthio, mercapto, mercaptomethyl, phosphono, carboxy, amino, cyano, and ethyne.

30. The composition of claim 29, wherein n is 1 and W is selected from the group consisting of cyano, alkyl-sulfonyl, acyl, carboxyl, carboxy alkly, carboxaryl, arylsulfonyl, aldehyde, alkyl, and aryl.

31. The composition of claim 29, wherein W is absent and said redox-active molecule attached to a bipod tether has the formula:

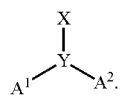

32. The composition of claim 31, wherein Y is selected from the group consisting of N, P, B, As, CH, C-alkyl, C-aryl, and C-heterocyclic.

33. The composition of any one of claims 1, 2, 4, 5, 29, and 30-32, wherein X is a porphyrinic macrocycle.

34. The composition of any one of claims 1, 2, 4, 5, 29, and 30-32, wherein X is a porphyrinic macrocycle having at least two different and distinguishable non-zero oxidation states.

35. The composition of any one of claims 1, 2, 4, 5, 29, and 30-32, wherein X is a porphyrin sandwich compound.

36. The composition of any one of claims 1, 2, 4, 5, 29, and 30-32, wherein X is a porphyrin dyad.

37. The composition of any one of claims 1, 2, 4, 5, 29, and 30-32, wherein X has the formula:

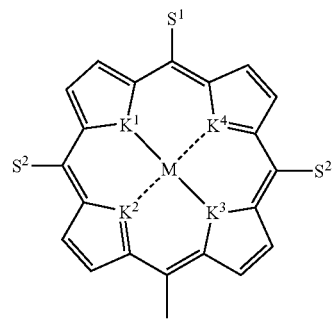

wherein:
M is present or absent and when present is selected from the group consisting of a metal, and a metalloid;
$K^1$, $K^2$, $K^3$, and $K^4$ are independently selected from the group consisting of a group IV element, a group V element, a group VI element, and CH;
$S^1$, $S^2$, and $S^3$ are substituents independently selected from the group consisting of aryl, phenyl, cycloalkyl, alkyl, halogen, alkoxy, alkylthio, perfluoroalkyl, alkenyl, alkynyl, perfluoroaryl, pyridyl, cyano, thiocyanato, nitro, amino, alkylamino, acyl, sulfoxyl, sulfonyl, imido, amido, imidazolyl, and carbamoyl, wherein said substituents provide a redox potential range of less than about 2 volts.

38. The composition of claim 37, wherein $K^1$, $K^2$, $K^3$, and $K^4$ are independently selected from the group consisting of N, O, S, Se, Te, and CH.

39. The composition of claim 37, wherein M is present and is selected from the group consisting of Zn, Mg, Cd, Hg, Cu, Ag, Au, Ni, Pd, Pt, Co, Rh, Ir, Mn, B, Al, Ga, Pb, and Sn.

40. The composition of claim 37, wherein M is selected from the group consisting of Zn, Mg, and Ni.

41. The composition of claim 37, wherein $S^1$, $S^2$, and $S^3$ are all the same.

42. The composition of claim 37, wherein $K^1$, $K^2$, $K^3$, and $K^4$ are all the same.

43. The composition of claim 37, wherein $K^1$, $K^2$, $K^3$, and $K^4$ are all N.

44. The composition of claim 37, wherein X ha the formula:

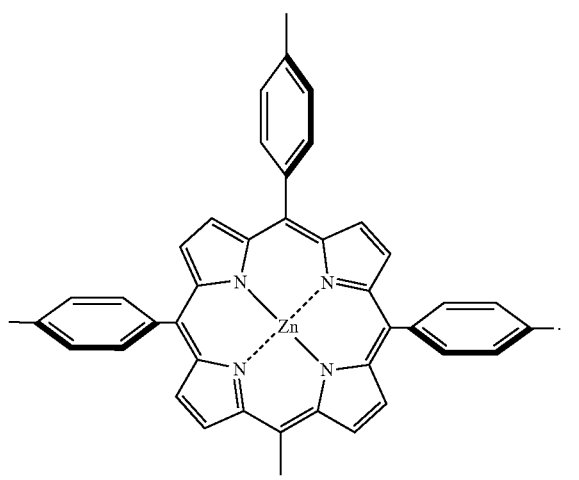

45. The composition of claim 1, wherein the multi-podal tether is attached to an electrode through at least one leg of the tether.

46. The composition of claim 45, wherein said tether is attached to a substrate comprising a material selected from the group consisting of titanium (Ti), zirconium (Zr), hafnium (Hf), rutherfordium (Rf), vanadium (V), niobium (Nb), tantalum (Ta) and dubnium (Db), chromium (Cr), molybdenum (Mo), tungsten (W), and seaborgium (Sg), and a metal.

47. The composition of claim 45, wherein said tether is attached to a substrate comprising a material selected from the group consisting of silicon, germanium, silver, gold, copper, titanium, tantalum, tungsten, a doped silicon, a doped germanium, a silicon oxide, a germanium oxide, a silver oxide, a copper oxide, a titanium oxide, a tantalum oxide, a tungsten oxide, a silicon nitride, a germanium nitride, a silver nitride, a copper nitride, a titanium nitride, a tantalum nitride, and a tungsten nitride.

48. The composition of claim 45, wherein said tether is attached to an electrode comprising Si(100).

49. The composition of claim 2, wherein the redox-active molecule attached to a tripod tether has the formula:

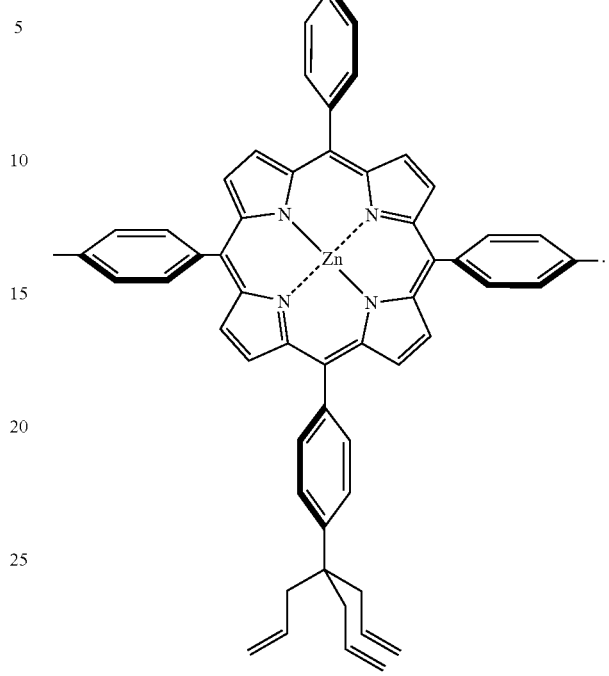

50. The composition of claim 2, wherein the redox-active molecule attached to a tripod tether has the formula:

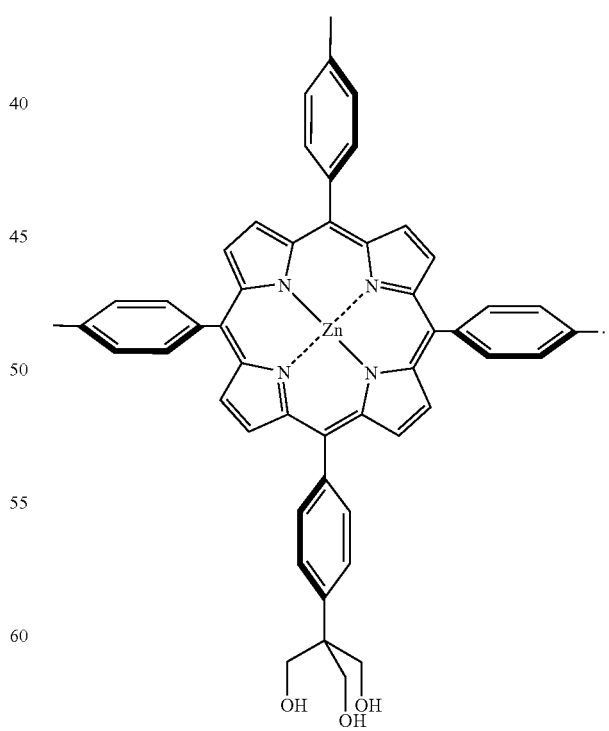

51. The composition of claim 28, wherein the redox-active molecule attached to a bipod tether has the formula:

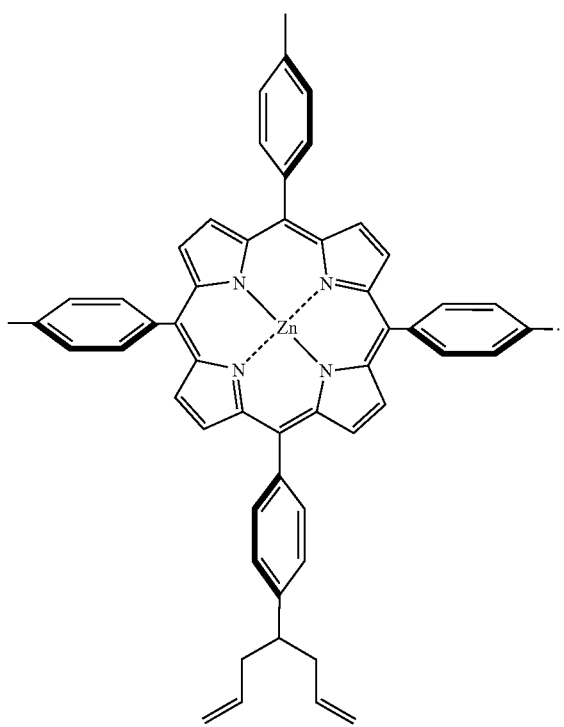

52. The composition of claim 29, wherein the redox-active molecule attached to a bipod tether has the formula:

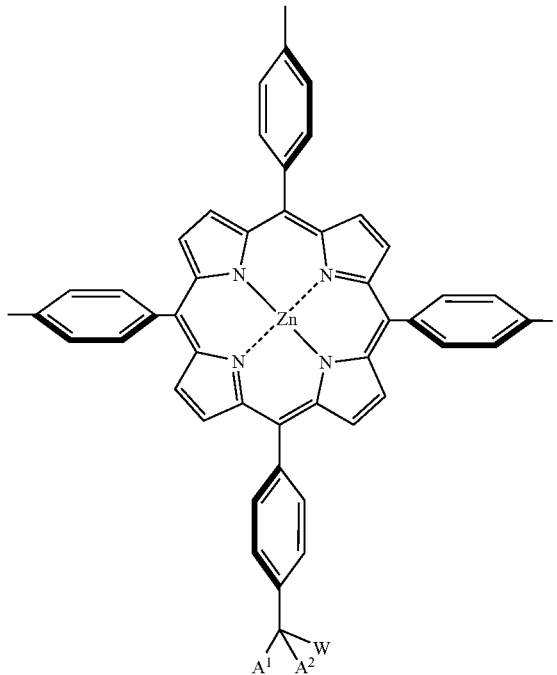

wherein $A^1$ and $A^2$ are independently selected from the group consisting of bromo, iodo, hydroxy, hydroxymethyl, formyl, bromomethyl, vinyl, allyl, thiol, selenyl, S-acetylthio, S-acetylthio, mercapto, mercaptomethyl, and ethyne.

53. The composition of claim 52, wherein W is selected from the group consisting of H, cyano, alkyl-sulfonyl, acyl, carboxyl, carboxy alkyl, carboxaryl, arylsulfonyl, aldehyde, alkyl, and aryl.

54. The composition of claim 1, wherein said plurality of electrodes each comprising a redox-active molecule attached to the electrode is disposed such that the oxidation state of the redox-active molecules can be independently set or read at least $10^6$ different locations in said array.

55. The composition of claim 1, wherein said plurality of electrodes are encapsulated.

56. The composition of claim 1, wherein said plurality of electrodes are disposed within an electrolyte.

57. A composition comprising a redox-active molecule selected from the group consisting of a porphyrinic macrocycle, a sandwich compound of the formula $L^1$-M-$L^2$ or formula $L^1$-$M^1$-$L^2$-$M^2$-$L^3$ where M, $M^1$, and $M^2$ are independently selected metals and $L^1$, $L^2$, and $L^3$ are independently selected porphyrins or porphyrinic macrocycles, and a metallocene, wherein said redox-active molecule is attached to a polypodal tether wherein said polypodal tether is a 2-podal, 3-podal, 4-podal, or 5-podal tether, the legs of said tether do not contain a benzene and each leg of said tether contains at least one carbon and not more than 10 carbons.

58. The composition of claim 57, wherein said composition comprises a tripod tether and excludes tethers having the formula:

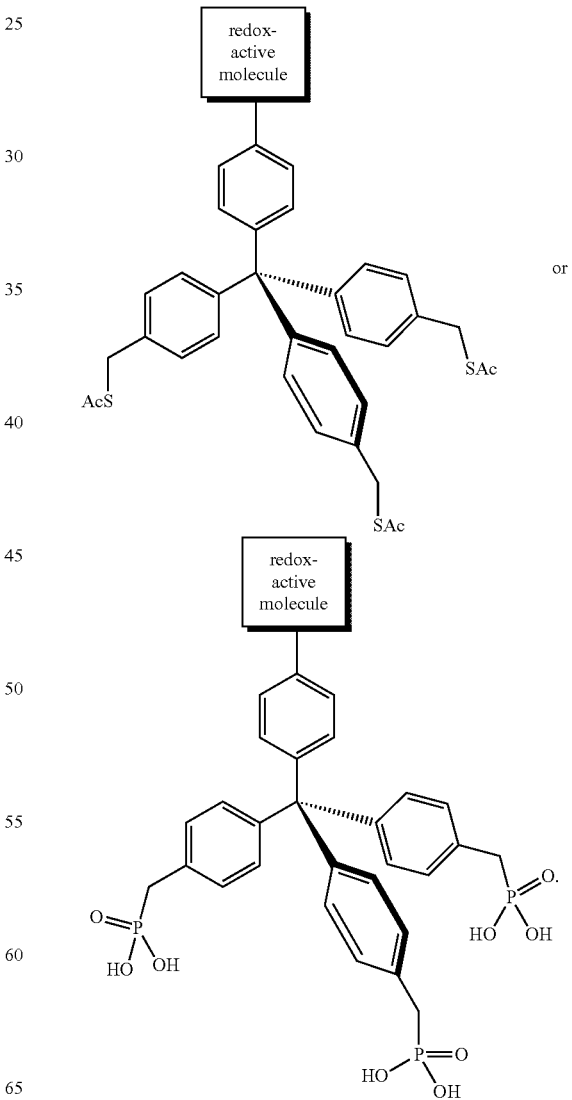

59. The composition of claim 58, wherein the redox-active molecule attached to a tripod tether has the formula:

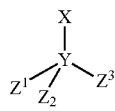

wherein:
X is said redox-active molecule;
Y is selected from the group consisting of a heteroatom, a carbon, a straight chain substituted or unsubstituted hydrocarbon, a branched hydrocarbon, and a cyclic hydrocarbon;
$Z^1$, $Z^2$, and $Z^3$ are independently selected from the group consisting of alkyl, aryl, heterocycle, vinylalkyl, ethynylalkyl, hydroxyalkyl, and carboxyalkyl.

60. The composition of claim 59, wherein, when Y is not a carbon or a heteroatom, at least two of $Z^1$, $Z^2$, and $Z^3$ are attached to different atoms.

61. The composition of claim 59, wherein X is a porphyrin.

62. The composition of claim 58, wherein Y is selected from the group consisting of, a two carbon alkyl, a 3 carbon alkyl, and a 4 carbon alkyl, and a cyclic hydrocarbon.

63. The composition of claim 62, wherein Y is a cyclic hydrocarbon selected from the group consisting of carboranyl ($C_2B_{10}H_{12}$) carboranyl ($C_2B_8H_{10}$), staffane, cubanediyl, bicyclo[2.2.2]octanediyl, cyclohexyl, cyclopentyl, and adamantyl.

64. The composition of claim 58, wherein Y is carbon.

65. The composition of claim 58, wherein Y is a heteroatom.

66. The composition of claim 58, wherein at least one of the legs of said tripod tether is selected from the group consisting of an alcohol, a hydroxyalkyl, an alkyl, an allyl, an allyl-terminated hydrocarbon, an alkyne, an alkyne-terminated hydrocarbon, and an ethyleneoxy unit (—$CH_2CH_2$—O—).

67. The composition of claim 66, wherein all three legs of said tripod tether are selected from the group consisting of an alcohol, a hydroxyalkyl, an alkyl, an allyl, an allyl-terminated hydrocarbon, an alkyne, an alkyne-terminated hydrocarbon, and an ethyleneoxy unit (—$CH_2CH_2$—O—).

68. The composition of claim 66, wherein all three legs of said tripod tether are identical.

69. The composition of claim 66, wherein said alkyl is a substituted alkyl.

70. The composition of claim 69, wherein said substituted alkyl is an alkylallyl.

71. The composition of claim 70, wherein said redox-active molecule attached to a tripod tether has the formula:

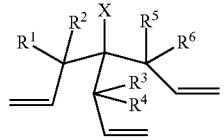

wherein
X is said redox-active molecule;
$R^1$, $R^2$, $R^3$, $R^4$, $R^5$, and $R^6$ are independently selected from the group consisting of H, OH, and alkyl; and
when $R^1$ and $R^2$ are the same they are both H or methyl, and when $R^3$ and $R^4$ are the same they are both H or methyl, and when $R^5$ and $R^6$ are the same they are both H or methyl.

72. The composition of claim 71, wherein $R^1$, $R^2$, $R^3$, $R^4$, $R^5$, and $R^6$ are all H.

73. The composition of claim 69, wherein said substituted alkyl is a hydroxyalkyl.

74. The composition of claim 73, wherein said redox-active molecule attached to a tether has the formula:

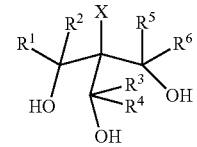

wherein
X is said redox-active molecule;
$R^1$, $R^2$, $R^3$, $R^4$, $R^5$, and $R^6$ are independently selected from the group consisting of H, OH, and alkyl; and
when $R^1$ and $R^2$ are the same they are both H or methyl, and when $R^3$ and $R^4$ are the same they are both H or methyl, and when $R^5$ and $R^6$ are the same they are both H or methyl.

75. The composition of claim 74, wherein $R^1$, $R_2$, $R^3$, $R^4$, $R^5$, and $R^6$ are all H.

76. The composition of claim 58, wherein at least one of the legs of said tripod tether is an aryl.

77. The composition of claim 76, wherein said aryl is a substituted aryl.

78. The composition of claim 77, wherein said substituted aryl has a substituent selected from the group consisting of S-acetylthioalkyl, phosphonoalkyl, vinyl, allyl, ethynyl, propargyl, hydroxy, carboxy, cyano, amino, formyl, bromo, iodo, chloro, mercapto, selenyl, telluryl, phosphono, S-acetylthio, Se-acetylseleno, and Te-acetyltelluro.

79. The composition of claim 58, wherein the redox-active molecule attached to a tripodal tether has the formula:

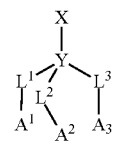

wherein
X is said redox-active molecule;
$L^1$, $L^2$, and $L^3$ are independently selected from the group consisting of a C, a two carbon alkyl, a 3 carbon alkyl, and a 4 carbon alkyl, and an ethyleneoxy; and
$A^1$, $A^2$, and $A^3$ are surface attachment groups independently selected from the group consisting of bromo, iodo, hydroxy, hydroxymethyl, formyl, bromomethyl, vinyl, allyl, thiol, selenyl, S-acetylthio, S-acetylthio, mercapto, mercaptomethyl, phosphono, carboxy, amino, cyano, and ethyne.

80. The composition of claim 79, wherein the redox-active molecule attached to a tripodal tether has the formula:

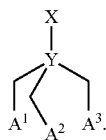

81. The composition of claim 79, wherein the redox-active molecule attached to a tripodal tether has the formula:

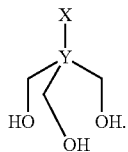

82. The composition of claim 79, wherein the redox-active molecule attached to a tether has the formula:

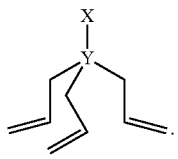

83. The composition of claim 57, wherein said composition comprises a bipod tether.

84. The composition of claim 83, wherein said composition comprises a redox-active molecule attached to a bipod tether, said redox-active molecule attached to a bipod tether having the formula:

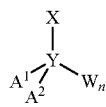

wherein:
X is said redox-active molecule;
Y is selected from the group consisting of a heteroatom, a carbon, a straight chain substituted or unsubstituted hydrocarbon, a branched hydrocarbon, and a cyclic hydrocarbon;
n is zero or one;
W, when present, is selected from the group consisting of H, alkyl, aryl, cyano, alkyl-sulfonyl, acyl, carboxyl, carboxy alkly, carboxaryl, arylsulfonyl, and aldehyde; and
$A^1$ and $A^2$ are independently selected from the group consisting of bromo, iodo, hydroxy, hydroxymethyl, formyl, bromomethyl, vinyl, allyl, thiol, selenyl, S-acetylthio, S-acetylthio, mercapto, mercaptomethyl, phosphono, carboxy, amino, cyano, and ethyne.

85. The composition of claim 84, wherein W is absent and said redox-active molecule attached to a bipod tether has the formula:

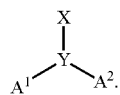

86. The composition of claim 85, wherein Y is selected from the group consisting of N, P, B, As, CH, C-alkyl, C-aryl, and C-heterocyclic.

87. The composition of any one of claims 57, 58-60, 61-84, 85, and 86, wherein X is selected from the group consisting of an aromatic group, a heterocycle, an aryl, an alkyl, a linear aliphatic, a branched aliphatic, a cyclic aliphatic, a coordination compound, a polycyclic aliphatic, and a heteroaromatic.

88. The composition of any one of claims 57, 58-60, 61-84, 85, and 86, wherein X is a p-phenylene.

89. The composition of any one of claims 57, 58-60, 61-84, 85, and 86, wherein X is a porphyrinic macrocycle.

90. The composition of any one of claims 57, 58-60, 61-84, 85, and 86, wherein X is a porphyrinic macrocycle having at least two different and distinguishable non-zero oxidation states.

91. The composition of any one of claims 57, 58-60, 61-84, 85, and 86, wherein X is a porphyrin sandwich compound.

92. The composition of any one of claims 57, 58-60, 61-84, 85, and 86, wherein X is a porphyrin dyad.

93. The composition of any one of claims 57, 58-60, 61-84, 85, and 86, wherein X has the formula:

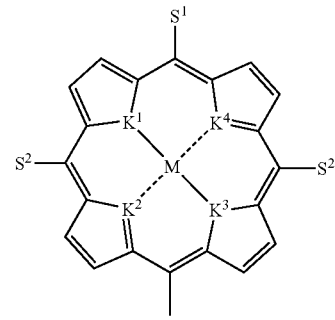

wherein:
M is present or absent and when present is selected from the group consisting of a metal, and a metalloid;
$K^1$, $K^2$, $K^3$, and $K^4$ are independently selected from the group consisting of a group IV element, a group V element, a group VI element, and CH;
$S^1$, $S^2$, and $S^3$ are substituents independently selected from the group consisting of aryl, phenyl, cycloalkyl, alkyl, halogen, alkoxy, alkylthio, perfluoroalkyl, alkenyl, alkynyl, perfluoroaryl, pyridyl, cyano, thiocyanato, nitro, amino, alkylamino, acyl, sulfoxyl, sulfonyl, imido, amido, imidazolyl, and carbamoyl, wherein said substituents provide a redox potential range of less than about 2 volts.

94. The composition of claim 93, wherein $K^1$, $K^2$, $K^3$, and $K^4$ are independently selected from the group consisting of N, O, S, Se, Te, and CH.

95. The composition of claim 93, wherein M is present and is selected from the group consisting of Zn, Mg, Cd, Hg, Cu, Ag, Au, Ni, Pd, Pt, Co, Rh, Ir, Mn, B, Al, Ga, Pb, and Sn.

96. The composition of claim 93, wherein M is selected from the group consisting of Zn, Mg, and Ni.

97. The composition of claim 93, wherein $S^1$, $S^2$, and $S^3$ are all the same.

98. The composition of claim 93, wherein $K^1$, $K^2$, $K^3$, and $K^4$ are all the same.

99. The composition of claim 93, wherein $K^1$, $K^2$, $K^3$, and $K^4$ are all N.

100. The composition of claim 93, wherein X has the formula:

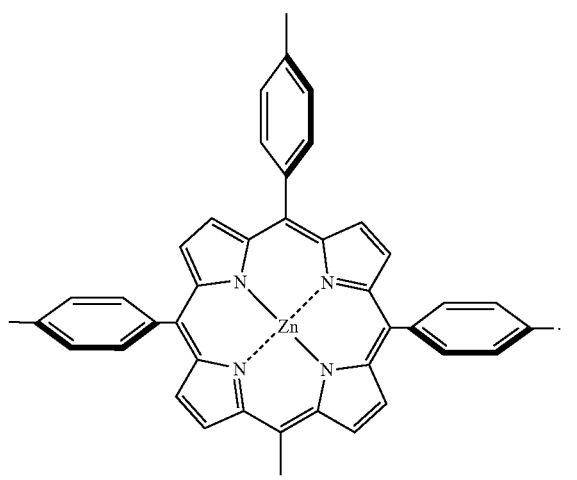

101. The composition of claim 57, wherein the multi-podal tether is attached to an electrode through at least one leg of the tether.

102. The composition of claim 101, wherein said tether is attached to a substrate comprising a material selected from the group consisting of titanium (Ti), zirconium (Zr), hafnium (Hf), rutherfordium (Rf), vanadium (V), niobium (Nb), tantalum (Ta) and dubnium (Db), chromium (Cr), molybdenum (Mo), tungsten (W), and seaborgium (Sg), and a metal.

103. The composition of claim 101, wherein said tether is attached to a substrate comprising a material selected from the group consisting of silicon, germanium, silver, gold, copper, titanium, tantalum, tungsten, a doped silicon, a doped germanium, a silicon oxide, a germanium oxide, a silver oxide, a copper oxide, a titanium oxide, a tantalum oxide, a tungsten oxide, a silicon nitride, a germanium nitride, a silver nitride, a copper nitride, a titanium nitride, a tantalum nitride, and a tungsten nitride.

104. The composition of claim 101, wherein said tether is attached to and electrode comprising Si(100).

105. The composition of claim 58, wherein the redox-active molecule attached to a tripod tether has the formula:

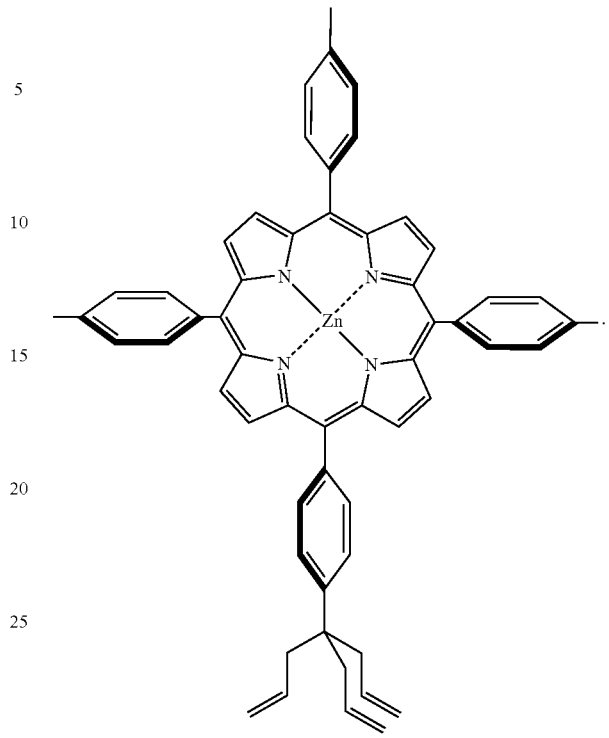

106. The composition of claim 58, wherein the redox-active molecule attached to a tripod tether has the formula:

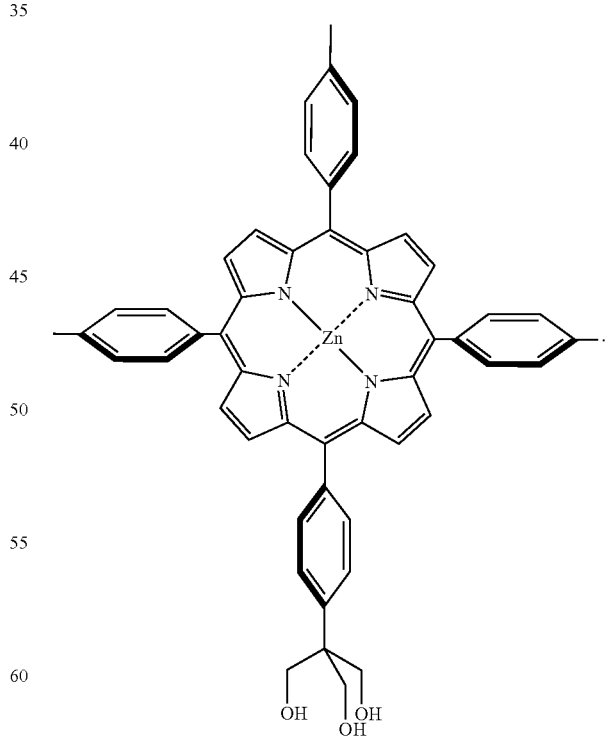

107. The composition of claim 84, wherein the redox-active molecule attached to a bipod tether has the formula:

108. The composition of claim 84, wherein the redox-active molecule attached to a bipod tether has the formula:
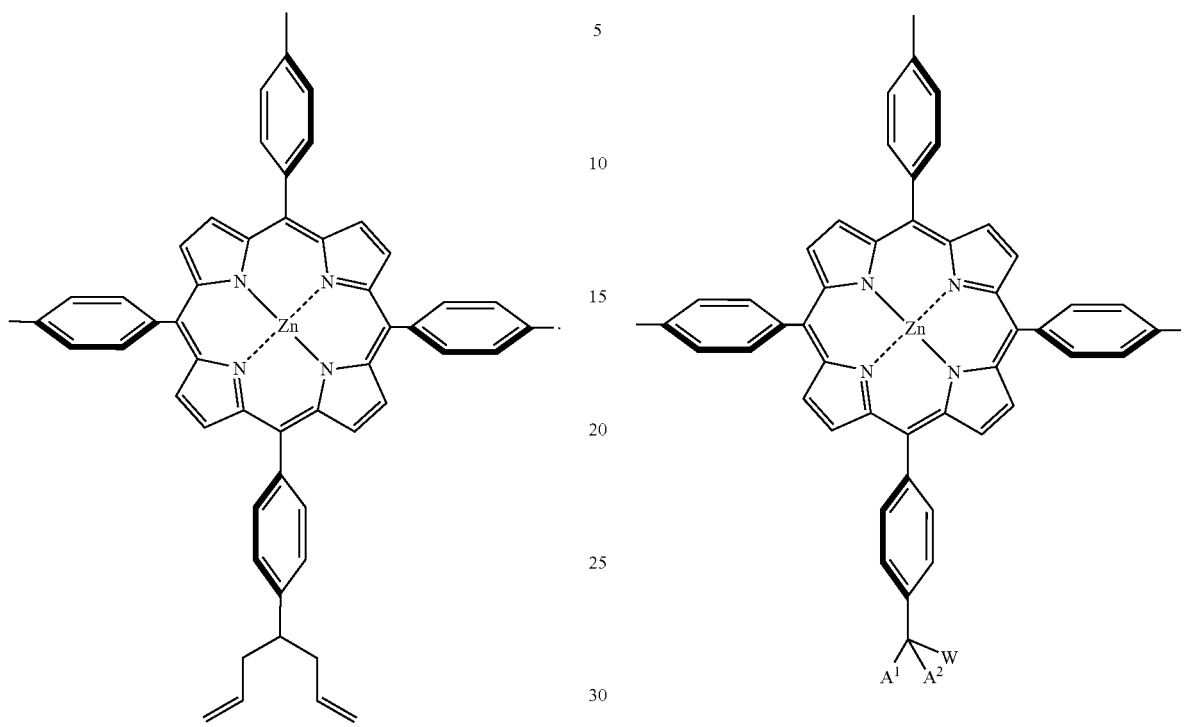
wherein $A^1$ and $A^2$ are independently selected from the group consisting of bromo, iodo, hydroxy, hydroxymethyl, formyl, bromomethyl, vinyl, allyl, thiol, selenyl, S-acetylthio, S-acetylthio, mercapto, mercaptomethyl, propargyl, and ethyne.
* * * * *